US010563213B2

(12) United States Patent
D'Aoust et al.

(10) Patent No.: US 10,563,213 B2
(45) Date of Patent: Feb. 18, 2020

(54) MODIFIED CPMV ENHANCER ELEMENTS

(71) Applicant: Medicago Inc., Quebec (CA)

(72) Inventors: Marc-Andre D'Aoust, Quebec (CA); Pierre-Olivier Lavoie, Quebec (CA)

(73) Assignee: Medicago Inc., Quebec (CA)

( * ) Notice: Subject to any disclaimer, the term of this patent is extended or adjusted under 35 U.S.C. 154(b) by 0 days.

(21) Appl. No.: 15/129,269

(22) PCT Filed: Mar. 27, 2015

(86) PCT No.: PCT/CA2015/050240
§ 371 (c)(1),
(2) Date: Sep. 26, 2016

(87) PCT Pub. No.: WO2015/143567
PCT Pub. Date: Oct. 1, 2015

(65) Prior Publication Data

US 2018/0119158 A1 May 3, 2018

Related U.S. Application Data

(63) Continuation-in-part of application No. PCT/CA2014/050326, filed on Mar. 28, 2014.

(60) Provisional application No. 61/971,274, filed on Mar. 27, 2014.

(51) Int. Cl.
*C12N 15/82* (2006.01)
*C07K 14/11* (2006.01)

(52) U.S. Cl.
CPC .......... *C12N 15/8216* (2013.01); *C07K 14/11* (2013.01)

(58) Field of Classification Search
None
See application file for complete search history.

(56) References Cited

U.S. PATENT DOCUMENTS

| | | | | |
|---|---|---|---|---|
| 4,692,028 | A | 9/1987 | Schave | |
| 4,945,050 | A | 7/1990 | Sanford et al. | |
| 4,962,028 | A | 10/1990 | Bedbrook et al. | |
| 5,036,006 | A | 7/1991 | Sanford et al. | |
| 5,100,792 | A | 3/1992 | Sanford | |
| 5,428,147 | A | 6/1995 | Barker et al. | |
| 5,625,136 | A | 4/1997 | Koziel et al. | |
| 6,403,865 | B1 | 6/2002 | Koziel et al. | |
| 7,125,978 | B1 | 10/2006 | Vezina et al. | |
| 7,618,815 | B2 | 11/2009 | Ghabrial et al. | |
| 8,519,113 | B2 | 8/2013 | Lomonossoff et al. | |
| 8,674,084 | B2 * | 3/2014 | Sainsbury .......... | C12N 15/8203 536/23.72 |
| 9,056,901 | B2 | 6/2015 | Song et al. | |
| 2005/0091706 | A1 | 4/2005 | Klimyuk et al. | |
| 2012/0207786 | A1 | 8/2012 | Smith et al. | |
| 2012/0208876 | A1 | 8/2012 | Kong et al. | |

FOREIGN PATENT DOCUMENTS

| | | | |
|---|---|---|---|
| EP | 0175966 | 4/1986 | |
| EP | 0290395 | 11/1988 | |
| EP | 0331083 | 9/1989 | |
| EP | 3122883 | 2/2017 | |
| JP | 2003518377 A | 6/2003 | |
| JP | 2012157367 | 8/2012 | |
| JP | 2012530499 | 12/2012 | |
| WO | 01987006614 | 11/1987 | |
| WO | 199209696 | 6/1992 | |
| WO | 199400583 | 1/1994 | |
| WO | 2000063400 | 10/2000 | |
| WO | 2000037663 | 11/2000 | |
| WO | 2001/048145 A2 | 7/2001 | |
| WO | 2007/047831 A2 | 4/2007 | |
| WO | 2007135480 | 11/2007 | |
| WO | 2008148104 | 1/2009 | |
| WO | 2009009876 | 1/2009 | |
| WO | 2009076778 | 6/2009 | |
| WO | 2009087391 | 7/2009 | |
| WO | 2010003225 | 1/2010 | |
| WO | 2010148511 | 12/2010 | |
| WO | 2011/028914 A1 | 3/2011 | |
| WO | 2012058762 | 5/2012 | |
| WO | WO-2012058762 A1 * | 5/2012 | ......... C12N 15/8203 |
| WO | 2012126123 | 9/2012 | |
| WO | 2012083445 | 10/2012 | |
| WO | 2012171104 | 12/2012 | |
| WO | 2013044390 | 4/2013 | |
| WO | 2013068593 | 5/2013 | |

(Continued)

OTHER PUBLICATIONS

Sainsbury et al, 2009, Plant Biotechnology Journal, 7:682-693.*
Kanagarajan et al, 2012, PLoS One, 7: 1-10.*
Rangan et al, 2008, Mol Biotechnol, 39:207-213.*
Alamillo, J. et al., Use of virus vectors for the expression in plants of active full-length and single chain anti-coronavirus antibodies, Biotechnol. J., 2006, vol. 1, 1103-1111.
Bianchi, E., et al. Universal Influenza B Vaccine Based on the Maturational Cleavage Site of the Hemagglutinin Precursor. Journal of Virology, 2005, pp. 7380-7388.
Canizares, M., et al. A bipartite system for the constitutive an inducible expression of high levels of foreign proteins in plants. Plant Biotechnology Journal (2006), vol. 4, pp. 183-193.

(Continued)

*Primary Examiner* — Jason Deveau Rosen
(74) *Attorney, Agent, or Firm* — Quarles & Brady LLP

(57) ABSTRACT

An expression enhancer comprising, in series, a CPMV 5'UTR nucleotide sequence comprising nucleotides 1-160 of SEQ ID NO:1, or comprising a nucleotide sequence comprising from about with 80% to 100% sequence similarity with SEQ ID NO:1, and a stuffer fragment is provided. The stuffer fragment comprises a nucleotide sequence encoding an incomplete M protein and one or more kozak sequence active in a plant. Plants and plant matter comprising the expression enhancer and methods using the expression enhancer are also described.

21 Claims, 36 Drawing Sheets

Specification includes a Sequence Listing.

(56) References Cited

FOREIGN PATENT DOCUMENTS

| | | |
|---|---|---|
| WO | 2013043067 | 11/2013 |
| WO | 2014153674 | 10/2014 |

OTHER PUBLICATIONS

Chen, J. et al. Structure of the Hemagglutinin Precursor Cleavage Site, a Determinant of Influenza Pathogenicity and the Origin of the Labile Conformation. Cell, vol. 95, pp. 409-417, 1998.
D'Aoust, et al. The production of hemagglutinin-based virus-like particles in plants: a rapid, efficient and safe response to pandemic influenza. Plant Biotech. J. (2010) 8:607-619.
D'Aoust, et al. Influenza virus-like particles produced by transient expression in Nicotiana benthamiana induce a protective immune response against a lethal viral challenge in mice. Plant Biotechnology Journal (2008) vol. 6, pp. 930-940.
Extended European Search Report, EP 2978848 dated Oct. 18, 2016.
Extended European Search Report, EP3092309 dated May 26, 2017.
GenBank Accession AGX20074.1.
GenBank Accession GQ497237.1.
Gleba, et al. Engineering viral expression vectors for plant: the full virus and the deconstructed virus strategies (2004). Curr. Opin. In Plant Biol. 7:182-188.
Gopinath, K, et al. Engineering Cowpea Mosaic Virus RNA-2 into a vector to express Heterologous proteins in plants. Virology, 2000, vol. 267(2), pp. 159-173.
Gutierrez, R., et al. Current perspectives on mRNA stability in plants: multiple levels and mechanisms of control. Trends in Plant Science, vol. 4:11, 1999, pp. 429-438.
Hoffmann, E., et al. Eight-plasmid system for rapid generation of influenza virus vaccines. Vaccine, vol. 20, pp. 3165-3170. 2002.
Holness, C.L., et al. Identification o the initiation codons for translation of Cowpea Mosaic Virus middle component RNA using site-directed mutagenesis of an infectious cDNA Clone. Viroloty, 1989, vol. 172(1), pp. 311-320.
Horimoto, T., et al. The development and characterization of H5 influenza virus vaccines derived from a 2003 human isolate. Vaccine (2006) vol. 24, pp. 3669-3676.
International Search Report and Written Opinion, PCT/CA 2015/050240, dated Jun. 25, 2015, 11 pages.
International Search Report, PCT/CA2014/050326, dated Jul. 16, 2014, 5 pages.
International Search Report, PCT/CA2015/050009, dated Apr. 17, 2015, 16 pages.
Kanagarajan, et al., Transient expression of hemagglutinin antigen from low pathogenic avian influenza A (H7N7) in Nicotiana benthamiana. PLoS One 7/3:1-10, Mar. 2012.
Kawaguchi, R. and Bailey-Serres, J. Regulation of translational initiation in plants. Curent Opinion in Plant Biology (2002). vol. 5:5, pp. 460-465.
Kozak, M. At least six nucleotides preceding the AUG initiator codon enhance translation in mammalian cells. J. Mol. Biol., 1987, vol. 196(4), pp. 947-950.
Landry, Nathalie, et al. Preclinical and clinical development of plant-made virus-like particle vaccine against avian H5N1 influenza. PLOS One, vol. 5:12, pp. e15559, 2010.
Liu, L., and Lomonossoff, G., Agroinfection as a rapid method for propagating Cowpea mosaic virus-based constructs. Journal of Virological Methods. (2002) vol. 105, pp. 343-348.
Liu, L., et al. Cowpea mosaic virus-based systems for the production of antigens and antibodies in plants. Vaccine 23 (2005) pp. 1788-1792.
Lomonossoff, et al. Cowpea mosaic virus as a versatile system for the expression of foreign peptides and proteins in legumes. Molecular Farming. Proceedings of the OECD workshop, La Grande Motte, France, Sep. 3-6, 2000 (2001) pp. 151-160.
Mechtcheriakova et al: "The use of viral vectors to produce hepatitis B virus core particles in plants" Journal of Virological Methods, Amsterdam, NL, vol. 131, No. 1, Jan. 2006 (Jan. 2006), pp. 10-15.
Monger, Wendy, et al. An antibody derivative expressed from viral vectors passively immunizes pigs against transmissible gastroenteritis virus infection when supplied orally in crude plant extracts. Plant Biotechnology Journal, 2006, vol. 4, pp. 623-631.
Mortimer, E., et al. Setting up a platform for plant-based influenza virus vaccine production in South Africa. BMC Biotechnology 2012, 12:14, pp. 1-10.
Rangan, L., et al. Analysis of Context Sequence Surrounding Translation Initiation Site from Complete Genome of Model Plants. Mol. Biotechnol., 2008, vol. 39, pp. 207-213.
Rohll, J., et al. 3'-Terminal nucleotide sequences important for the accumulation of Cowpea Mosaic Virus M-RNA. Virology, 1993, vol. 193, pp. 672-679.
Sainsbury, et al., Extremely high-level and rapid transient protein production in plants without the use of viral replication. Plant Physiology. (2008) vol. 148, 1212-1218.
Sainsbury, et al., Cowpea mosaic virus: the plant virus-based biotechnology workhorse. Annu. Rev. Phytopathol. 48:437-455, Mar. 2010.
Sainsbury, et al., Cowpea mosaic virus-based expression vectors. (2007) In K Hefferon, ed, Virus Expression Vectors. Transworld Research Network, Kerala, India, pp. 339-355.
Sainsbury, et al., pEAQ: versatile expression vectors for easy and quick transient expression of heterologous proteins in plants. Plant Biotechnology Journal (2009), 7, pp. 682-693.
Sainsbury, et al., Recombinant Proteins From Plants, 2009, Methods in Molecular Biology, vol. 483: 25-39.
Sainsbury, F., et al. Expression of multiple proteins using full-length and deleted versions of cowpea mosaic virus RNA-2. Plant Biotechnology Journal, vol. 6, 2008, pp. 82-92.
Shoji, Y., et al. A plant-produced H1N1 trimeric hemagglutinin protects mice from a lethal influenza virus challenge. Human Vaccines and Immunotherapeutics, vol. 9, 2013, pp. 553-560.
Song, J., et al. Protective Immunity against H5N1 Influenza virus by a single dose vaccination with virus-like particles. Virology, 2010, vol. 405(1), 165-175.
Van Bokhoven, H., et al. Cis- and trans-acting elements in cowpea mosaic virus RNA replication. Virology, 1993, 195, 377-386.
Verch, T, Yusibov, V. & Koprowski, H. Expression and assembly of a full-length monoclonal antibody in plants using a plant virus vector. J. Immunol. Methods 220, 69-75 (1998).
Verver, J., et al. Studies on movement of Cowpea Mosaic Virus using the jellyfish green fluorescent protein. Virology 242, 22-27, 1998.
Wang, K., et al. Viral proteins function as ion channels. Biochimica et Biophysica Acta. vol. 1808:2, Feb. 2011, pp. 510-515.
Wellink, J., et al. Mutational analysis of AUG codons of cowpea mosaic virus M RNA. Biochimie, vol. 75:8, 1993, pp. 741-747.
Written Opinion and Search Report from SG 11201509280Q dated Dec. 15, 2016, 14 pages.
Yusibov, V., et al. Antigens produced in plants by infection with chimeric viruses immunize against rabies virus and HIB-1. Proc. Nat'l. Acad. Sci. USA vol. 94, pp. 5784-5788, 1997.
Serizawa, R., et al. Technical Advance. Custom-Designed MLPA Using Multiple Short Synthetic Probes. Application to Methylation Analysis of Five Promoter CpG Islands in Tymor and Urine Specimens from Patients with Bladder Cancer. J of Molecular Diagnostics, vol. 12:4, 2010, pp. 402-408.
OA dated Dec. 15, 2011 re CA 2,651,907.
RR re U.S. Appl. No. 12/300,922, filed Apr. 21, 2011.
OA re U.S. Appl. No. 12/300,922, filed Jul. 20, 2011.
OA re U.S. Appl. No. 12/300,922, filed Feb. 16, 2012.
OA re U.S. Appl. No. 12/300,922, filed Nov. 15, 2012.
NOA Jun. 11, 2013 re U.S. Appl. No. 12/300,922.
EESR Nov. 7, 2016 re EP 14773061.8.
Office Action dated Nov. 4, 2016 re U.S. Appl. No. 14/779,423.
Office Action dated Jul. 19, 2017 re U.S. Appl. No. 14/779,423.
EESR Oct. 30, 2017 re EP 15769248.4.
Office Action dated Jan. 29, 2018 re U.S. Appl. No. 15/110,696.
Office Action re CN 201480029001.7 dated Jul. 24, 2017 (associate's translation).

(56) References Cited

OTHER PUBLICATIONS

OA Jan. 8, 2018 re EP 14773061.8.
Office Action dated Jan. 18, 2018 re JP 2016-504431 (associate's translation).
Inv. To Respond to Written Opinion dated Jan. 15, 2018 re SG 11201507928Q.
Fischetti, V., "Streptococcal M Protein: Molecular Design and Biological Behavior," Clinical Microbiology Reviews, 1989, pp. 285-314.
GenBank ACU12738.1, Influenza B virus, Aug. 24, 2017; 2 pages.
GenBank Accession AFD32428.2, Influenza A virus, Apr. 16, 2012, 2 pages.
Joshi, C.P., "An inspection of the domain between putative TATA box and translation start site in 79 plant genes," Nucleic Acids Research. vol. 15:16, 1987, pp. 6643-6653.
Lu, Xishan, et al., "Insights into Avian influenza virus pathogenicity: the hemagglutinin precursor HA0 of subtype H16 has an alpha-Helix structure in its cleavage site with inefficient HA1/HA2 cleavage," Journal of Virology, 2012, vol. 86:23, pp. 12861-12870.

* cited by examiner

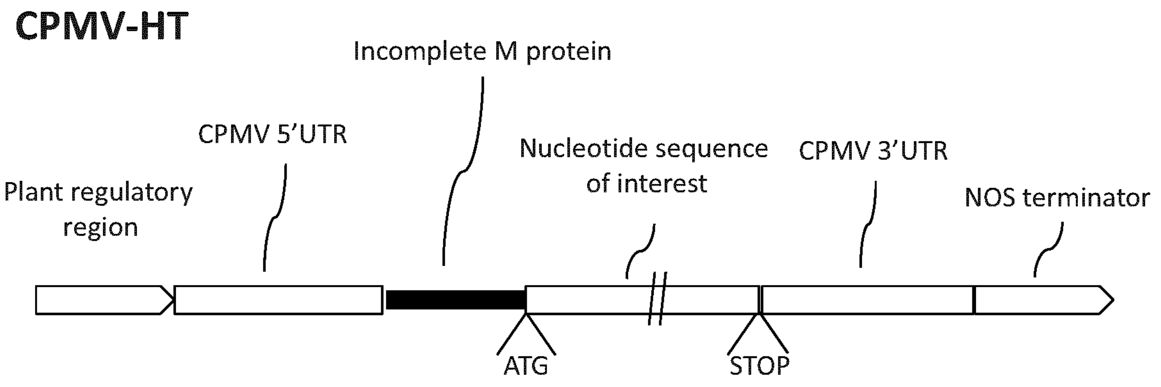
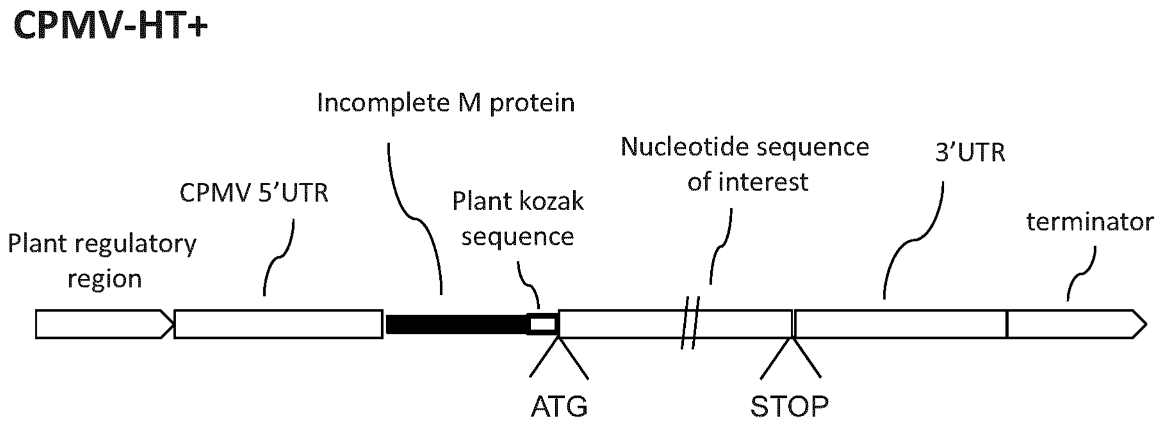
Figure 1a

- CPMV HT
  - 2X35S…TTCATTTGGAGAGGTATTAAAA…(CPMV HT 5'UTR)… ACCAGTACA(ACG)TTTT …M protein (incomplete)… AAATTTG*TCGGGCCC*ATG…(GOI)

- CPMV HT+
  - 2X35S…TTCATTTGGAGAGGTATTAAAA…(CPMV HT 5'UTR)…ACCAGTACA(ACG)TTTT …M protein (incomplete)…AAATTTG*TCGGGCCCAATACCGCGG*AGAAAATG…(GOI)

Figure 1b

Figure 5 A-2X35S/CPMV-HT/ PDISP/H3 Victoria/ NOS (Construct number 1391)

Figure 5A

IF-PDI.S1+3c (SEQ ID NO:18)

AAATTTGTCGGGCCCATGGCGAAAAACGTTGCGATTTTCGGCTTATTG

Figure 5B

IF-H3V36111.s1-4r (SEQ ID NO:19)

ACTAAAGAAAATAGGCCTTCAAATGCAAATGTTGCACCTAATGTTGCCCTT

Figure 5C

Nucleotide sequence of PDISP/H3 Victoria. (SEQ ID NO: 20)

ATGGCGAAAAACGTTGCGATTTTCGGCTTATTGTTTTCTCTTCTTGTGTTGGTTCCTTCTCAGATCTTCGCCCAAAAAC
TTCCTGGAAATGACAACAGCACGGCAACGCTGTGCCTTGGGCACCATGCAGTACCAAACGGAACGATAGTGAAAACAAT
CACGAATGACCAAATTGAAGTTACTAATGCTACTGAGCTGGTTCAGAATTCCTCAATAGGTGAAATATGCGACAGTCCT
CATCAGATCCTTGATGGAGAAAACTGCACACTAATAGATGCTCTATTGGGAGACCCTCAGTGTGATGGCTTCCAAAATA
AGAAATGGGACCTTTTTGTTGAACGAAGCAAAGCCTACAGCAACTGTTACCCTTATGATGTGCCGGATTATGCCTCCCT
TAGGTCACTAGTTGCCTCATCCGGCACACTGGAGTTTAACAATGAAAGCTTCAATTGGACTGGAGTCACTCAAAACGGA
ACAAGTTCTGCTTGCATAAGGAGATCTAATAATAGTTTCTTTAGTAGATTAAATTGGTTGACCCACTTAAACTTCAAAT
ACCCAGCATTGAACGTGACTATGCCAAACAATGAACAATTTGACAAATTGTACATTTGGGGGGTTCACCACCCGGGTAC
GGACAAGGACCAAATCTTCCTGTATGCTCAATCATCAGGAAGAATCACAGTATCTACCAAAAGAAGCCAACAAGCTGTA
ATCCCGAATATCGGATCTAGACCCAGAATAAGGAATATCCCTAGCAGAATAAGCATCTATTGGACAATAGTAAAACCGG
GAGACATACTTTTGATTAACAGCACAGGGAATCTAATTGCTCCTAGGGGTTACTTCAAAATACGAAGTGGGAAAAGCTC
AATAATGAGATCAGATGCACCCATTGGCAAATGCAATTCTGAATGCATCACTCCAAATGGAAGCATTCCCAATGACAAA
CCATTCCAAAATGTAAACAGGATCACATACGGGGCCTGTCCCAGATATGTTAAGCAAAGCACTCTGAAATTGGCAACAG
GAATGCGAAATGTACCAGAGAAACAAACTAGAGGCATATTTGGCGCAATAGCGGGTTTCATAGAAAATGGTTGGGAGGG
AATGGTGGATGGTTGGTACGGTTTCAGGCATCAAAATTCTGAGGGAAGAGGACAAGCAGCAGATCTCAAAAGCACTCAA
GCAGCAATCGATCAAATCAATGGGAAGCTGAATCGATTGATCGGGAAAACCAACGAGAAATTCCATCAGATTGAAAAAG
AATTCTCAGAAGTCGAAGGGAGAATTCAGGACCTTGAGAAATATGTTGAGGACACTAAAATAGATCTCTGGTCATACAA
CGCGGAGCTTCTTGTTGCCCTGGAGAACCAACATACAATTGATCTAACTGACTCAGAAATGAACAAACTGTTTGAAAAA
ACAAAGAAGCAACTAAGGGAAAATGCTGAGGATATGGGCAATGGTTGTTTCAAAATATACCACAAATGTGACAATGCCT
GCATAGGATCAATCAGAAATGGAACTTATGACCACGATGTATACAGAGATGAAGCATTAAACAACCGGTTCCAGATCAA
GGGAGTTGAGCTGAAGTCAGGGTACAAAGATTGGATCCTATGGATTTCCTTTGCCATATCATGTTTTTTGCTTTGTGTT
GCTTTGTTGGGGTTCATCATGTGGGCCTGCCAAAAGGGCAACATTAGGTGCAACATTTGCATTTGA

Schematic representation of construct 1191. SacII and StuI restriction enzyme sites used for plasmid linearization are annotated on the representation.

FIG. 5E

Construct 1191 from left to right t-DNA borders (underlined). 2X35S/CPMV-HT/NOS with Plastocyanine-P19-Plastocyanine silencing inhibitor expression cassette (SEQ ID NO: 21)

TGGCAGGATATATTGTGGTGTAAACAAATTGACGCTTAGACAACTTAATAACACATTGCGGACGTTTTTAATGTACTGA
ATTAACGCCGAATCCCGGGCTGGTATATTTATATGTTGTCAAATAACTCAAAAACCATAAAAGTTTAAGTTAGCAAGTG
TGTACATTTTTACTTGAACAAAAATATTCACCTACTACTGTTATAAATCATTATTAAACATTAGAGTAAAGAAATATGG
ATGATAAGAACAAGAGTAGTGATATTTTGACAACAATTTTGTTGCAACATTTGAGAAAATTTTGTTGTTCTCTCTTTTC
ATTGGTCAAAAACAATAGAGAGAGAAAAAGGAAGAGGGAGAATAAAAACATAATGTGAGTATGAGAGAGAAAGTTGTAC
AAAAGTTGTACCAAAATAGTTGTACAAATATCATTGAGGAATTTGACAAAAGCTACACAAATAAGGGTTAATTGCTGTA
AATAAATAAGGATGACGCATTAGAGAGATGTACCATTAGAGAATTTTTGGCAAGTCATTAAAAAGAAAGAATAAATTAT
TTTTAAAATTAAAAGTTGAGTCATTTGATTAAACATGTGATTATTTAATGAATTGATGAAAGAGTTGGATTAAAGTTGT
ATTAGTAATTAGAATTTGGTGTCAAATTTAATTTGACATTTGATCTTTTCCTATATATTGCCCCATAGAGTCAGTTAAC
TCATTTTTATATTTCATAGATCAAATAAGAGAAATAACGGTATATTAATCCCTCCAAAAAAAAAAAACGGTATATTTAC
TAAAAAATCTAAGCCACGTAGGAGGATAACAGGATCCCCGTAGGAGGATAACATCCAATCCAACCAATCACAACAATCC
TGATGAGATAACCCACTTTAAGCCCACGCATCTGTGGCACATCTACATTATCTAAATCACACATTCTTCCACACATCTG
AGCCACACAAAAACCAATCCACATCTTTATCACCCATTCTATAAAAAATCACACTTTGTGAGTCTACACTTTGATTCCC
TTCAAACACATACAAAGAGAAGAGACTAATTAATTAATTAATCATCTTGAGAGAAAATGGAACGAGCTATACAAGGAAA
CGACGCTAGGGAACAAGCTAACAGTGAACGTTGGGATGGAGGATCAGGAGGTACCACTTCTCCCTTCAAACTTCCTGAC
GAAAGTCCGAGTTGGACTGAGTGGCGGCTACATAACGATGAGACGAATTCGAATCAAGATAATCCCCTTGGTTTCAAGG
AAAGCTGGGGTTTCGGGAAAGTTGTATTTAAGAGATATCTCAGATACGACAGGACGGAAGCTTCACTGCACAGAGTCCT
TGGATCTTGGACGGGAGATTCGGTTAACTATGCAGCATCTCGATTTTTCGGTTTCGACCAGATCGGATGTACCTATAGT
ATTCGGTTTCGAGGAGTTAGTATCACCGTTTCTGGAGGGTCGCGAACTCTTCAGCATCTCTGTGAGATGGCAATTCGGT
CTAAGCAAGAACTGCTACAGCTTGCCCCAATCGAAGTGGAAAGTAATGTATCAAGAGGATGCCCTGAAGGTACTCAAAC
CTTCGAAAAAGAAAGCGAGTAAGTTAAAATGCTTCTTCGTCTCCTATTTATAATATGGTTTGTTATTGTTAATTTTGTT
CTTGTAGAAGAGCTTAATTAATCGTTGTTGTTATGAAATACTATTTGTATGAGATGAACTGGTGTAATGTAATTCATTT
ACATAAGTGGAGTCAGAATCAGAATGTTTCCTCCATAACTAACTAGACATGAAGACCTGCCGCGTACAATTGTCTTATA
TTTGAACAACTAAAATTGAACATCTTTTGCCACAACTTTATAAGTGGTTAATATAGCTCAAATATATGGTCAAGTTCAA
TAGATTAATAATGGAAATATCAGTTATCGAAATTCATTAACAATCAACTTAACGTTATTAACTACTAATTTTATATCAT
CCCCTTTGATAAATGATAGTACACCAATTAGGAAGGAGCATGCTCGCCTAGGAGATTGTCGTTTCCCGCCTTCAGTTTG
CAAGCTGCTCTAGCCGTGTAGCCAATACGCAAACCGCCTCTCCCCGCGCGTTGGGAATTACTAGCGCGTGTCGACAAGC
TTGCATGCCGGTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCTGTCACTTTA
TTGTGAAGATAGTGGAAAAGGAAGGTGGCTCCTACAAATGCCATCATTGCGATAAAGGAAAGGCCATCGTTGAAGATGC
CTCTGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGTCT
CAGAAGACCAAAGGGCAATTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGCGATAAAGGAAAGGCCATC
GTTGAAGATGCCTCTGCCGACAGTGGTCCCAAAGATGGACCCCCACCCACGAGGAGCATCGTGGAAAAAGAAGACGTTC
CAACCACGTCTTCAAAGCAAGTGGATTGATGTGATATCTCCACTGACGTAAGGGATGACGCACAATCCCACTATCCTTC
GCAAGACCCTTCCTCTATATAAGGAAGTTCATTTCATTTGGAGAGGTATTAAAATCTTAATAGGTTTTGATAAAAGCGA
ACGTGGGGAAACCCGAACCAAACCTTCTTCTAAACTCTCTCTCATCTCTCTTAAAGCAAACTTCTCTCTTGTCTTTCTT
GCGTGAGCGATCTTCAACGTTGTCAGATCGTGCTTCGGCACCAGTACAACGTTTTCTTTCACTGAAGCGAAATCAAAGA
TCTCTTTGTGGACACGTAGTGCGGCGCCATTAAATAACGTGTACTTGTCCTATTCTTGTCGGTGTGGTCTTGGGAAAAG
AAAGCTTGCTGGAGGCTGCTGTTCAGCCCCATACATTACTTGTTACGATTCTGCTGACTTTCGGCGGGTGCAATATCTC
TACTTCTGCTTGACGAGGTATTGTTGCCTGTACTTCTTTCTTCTTCTTCTTGCTGATTGGTTCTATAAGAAATCTAGTA
TTTTCTTTGAAACAGAGTTTTCCCGTGGTTTTCGAACTTGGAGAAAGATTGTTAAGCTTCTGTATATTCTGCCCAAATT
TGTCGGGCCCGCGGATGGCGAAAAACGTTGCGATTTTCGGCTTATTGTTTTCTCTTCTTGTGTTGGTTCCTTCTCAGAT
CTTCGCCTGCAGGCTCCTCAGCCAAAACGACACCCCCATCTGTCTATCCACTGGCCCCTGGATCTGCTGCCCAAACTAA
CTCCATGGTGACCCTGGGATGCCTGGTCAAGGGCTATTTCCCTGAGCCAGTGACAGTGACCTGGAACTCTGGATCCCTG
TCCAGCGGTGTGCACACCTTCCCAGCTGTCCTGCAGTCTGACCTCTACACTCTGAGCAGCTCAGTGACTGTCCCCTCCA
GCACCTGGCCCAGCGAGACCGTCACCTGCAACGTTGCCCACCCGGCCAGCAGCACCAAGGTGGACAAGAAAATTGTGCC
CAGGGATTGTGGTTGTAAGCCTTGCATATGTACAGTCCCAGAAGTATCATCTGTCTTCATCTTCCCCCCAAAGCCCAAG

FIG. 5E (cont.)

GATGTGCTCACCATTACTCTGACTCCTAAGGTCACGTGTGTTGTGGTAGACATCAGCAAGGATGATCCCGAGGTCCAGT
TCAGCTGGTTTGTAGATGATGTGGAGGTGCACACAGCTCAGACGCAACCCCGGGAGGAGCAGTTCAACAGCACTTTCCG
CTCAGTCAGTGAACTTCCCATCATGCACCAGGACTGGCTCAATGGCAAGGAGCGATCGCTCACCATCACCATCACCATC
ACCATCACCATTAAAGGCCTATTTTCTTTAGTTTGAATTTACTGTTATTCGGTGTGCATTTCTATGTTTGGTGAGCGGT
TTTCTGTGCTCAGAGTGTGTTTATTTTATGTAATTTAATTTCTTTGTGAGCTCCTGTTTAGCAGGTCGTCCCTTCAGCA
AGGACACAAAAAGATTTTAATTTTATTAAAAAAAAAAAAAAAAAAGACCGGGAATTCGATATCAAGCTTATCGACCTGC
AGATCGTTCAAACATTTGGCAATAAAGTTTCTTAAGATTGAATCCTGTTGCCGGTCTTGCGATGATTATCATATAATTT
CTGTTGAATTACGTTAAGCATGTAATAATTAACATGTAATGCATGACGTTATTTATGAGATGGGTTTTTATGATTAGAG
TCCCGCAATTATACATTTAATACGCGATAGAAAACAAAATATAGCGCGCAAACTAGGATAAATTATCGCGCGCGGTGTC
ATCTATGTTACTAGATCTCTAGAGTCTCAAGCTTGGCGCGCCCACGTGACTAGTGGCACTGGCCGTCGTTTTACAACGT
CGTGACTGGGAAAACCCTGGCGTTACCCAACTTAATCGCCTTGCAGCACATCCCCCTTTCGCCAGCTGGCGTAATAGCG
AAGAGGCCCGCACCGATCGCCCTTCCCAACAGTTGCGCAGCCTGAATGGCGAATGCTAGAGCAGCTTGAGCTTGGATCA
GATTGTCGTTTCCCGCCTTCAGTTTAAACTATCAGTGTTTGACAGGATATATTGGCGGGTAAACCTAAGAGAAAAGAGC
GTTTA

FIG. 5F

Expression cassette number 1391 from 2X35S promoter to NOS terminator. PDISP/H3 Victoria nucleotide sequence is underlined. (SEQ ID NO: 22)

GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA
TCTTCAACGTTGTCAGATCGTGCTTCGGCACCAGTACAACGTTTTCTTTCACTGAAGCGAAATCAAAGATCTCTTTGTG
GACACGTAGTGCGGCGCCATTAAATAACGTGTACTTGTCCTATTCTTGTCGGTGTGGTCTTGGGAAAAGAAAGCTTGCT
GGAGGCTGCTGTTCAGCCCCATACATTACTTGTTACGATTCTGCTGACTTTCGGCGGGTGCAATATCTCTACTTCTGCT
TGACGAGGTATTGTTGCCTGTACTTCTTTCTTCTTCTTCTTGCTGATTGGTTCTATAAGAAATCTAGTATTTTCTTTGA
AACAGAGTTTTCCCGTGGTTTTCGAACTTGGAGAAAGATTGTTAAGCTTCTGTATATTCTGCCCAAATTTGTCGGGCCC
ATGGCGAAAAACGTTGCGATTTTCGGCTTATTGTTTTCTCTTCTTGTGTTGGTTCCTTCTCAGATCTTCGCCCAAAAAC
TTCCTGGAAATGACAACAGCACGGCAACGCTGTGCCTTGGGCACCATGCAGTACCAAACGGAACGATAGTGAAAACAAT
CACGAATGACCAAATTGAAGTTACTAATGCTACTGAGCTGGTTCAGAATTCCTCAATAGGTGAAATATGCGACAGTCCT
CATCAGATCCTTGATGGAGAAAACTGCACACTAATAGATGCTCTATTGGGAGACCCTCAGTGTGATGGCTTCCAAAATA
AGAAATGGGACCTTTTTGTTGAACGAAGCAAAGCCTACAGCAACTGTTACCCTTATGATGTGCCGGATTATGCCTCCCT
TAGGTCACTAGTTGCCTCATCCGGCACACTGGAGTTTAACAATGAAAGCTTCAATTGGACTGGAGTCACTCAAAACGGA
ACAAGTTCTGCTTGCATAAGGAGATCTAATAATAGTTTCTTTAGTAGATTAAATTGGTTGACCCACTTAAACTTCAAAT
ACCCAGCATTGAACGTGACTATGCCAAACAATGAACAATTTGACAAATTGTACATTTGGGGGGTTCACCACCCGGGTAC
GGACAAGGACCAAATCTTCCTGTATGCTCAATCATCAGGAAGAATCACAGTATCTACCAAAAGAAGCCAACAAGCTGTA
ATCCCGAATATCGGATCTAGACCCAGAATAAGGAATATCCCTAGCAGAATAAGCATCTATTGGACAATAGTAAAACCGG
GAGACATACTTTTGATTAACAGCACAGGGAATCTAATTGCTCCTAGGGGTTACTTCAAAATACGAAGTGGGAAAAGCTC
AATAATGAGATCAGATGCACCCATTGGCAAATGCAATTCTGAATGCATCACTCCAAATGGAAGCATTCCCAATGACAAA
CCATTCCAAAATGTAAACAGGATCACATACGGGGCCTGTCCCAGATATGTTAAGCAAAGCACTCTGAAATTGGCAACAG
GAATGCGAAATGTACCAGAGAAACAAACTAGAGGCATATTTGGCGCAATAGCGGGTTTCATAGAAAATGGTTGGGAGGG
AATGGTGGATGGTTGGTACGGTTTCAGGCATCAAAATTCTGAGGGAAGAGGACAAGCAGCAGATCTCAAAAGCACTCAA
GCAGCAATCGATCAAATCAATGGGAAGCTGAATCGATTGATCGGGAAAACCAACGAGAAATTCCATCAGATTGAAAAAG
AATTCTCAGAAGTCGAAGGGAGAATTCAGGACCTTGAGAAATATGTTGAGGACACTAAAATAGATCTCTGGTCATACAA
CGCGGAGCTTCTTGTTGCCCTGGAGAACCAACATACAATTGATCTAACTGACTCAGAAATGAACAAACTGTTTGAAAAA

FIG. 5F (cont.)

ACAAAGAAGCAACTAAGGGAAAATGCTGAGGATATGGGCAATGGTTGTTTCAAAATATACCACAAATGTGACAATGCCT
GCATAGGATCAATCAGAAATGGAACTTATGACCACGATGTATACAGAGATGAAGCATTAAACAACCGGTTCCAGATCAA
GGGAGTTGAGCTGAAGTCAGGGTACAAAGATTGGATCCTATGGATTTCCTTTGCCATATCATGTTTTTGCTTTGTGTT
GCTTTGTTGGGGTTCATCATGTGGGCCTGCCAAAAGGGCAACATTAGGTGCAACATTTGCATTTGAAGGCCTATTTTCT
TTAGTTTGAATTTACTGTTATTCGGTGTGCATTTCTATGTTTGGTGAGCGGTTTTCTGTGCTCAGAGTGTGTTTATTTT
ATGTAATTTAATTTCTTTGTGAGCTCCTGTTTAGCAGGTCGTCCCTTCAGCAAGGACACAAAAAGATTTTAATTTTATT
AAAAAAAAAAAAAAAAAAGACCGGGAATTCGATATCAAGCTTATCGACCTGCAGATCGTTCAAACATTTGGCAATAAAG
TTTCTTAAGATTGAATCCTGTTGCCGGTCTTGCGATGATTATCATATAATTTCTGTTGAATTACGTTAAGCATGTAATA
ATTAACATGTAATGCATGACGTTATTTATGAGATGGGTTTTTATGATTAGAGTCCCGCAATTATACATTTAATACGCGA
TAGAAAACAAAATATAGCGCGCAAACTAGGATAAATTATCGCGCGCGGTGTCATCTATGTTACTAGAT

FIG. 5G

Amino acid sequence of PDISP/H3 Victoria (SEQ ID NO: 23)

MAKNVAIFGLLFSLLVLVPSQIFAQKLPGNDNSTATLCLGHHAVPNGTIVKTITNDQIEVTNATELVQNSSIGEICDSP
HQILDGENCTLIDALLGDPQCDGFQNKKWDLFVERSKAYSNCYPYDVPDYASLRSLVASSGTLEFNNESFNWTGVTQNG
TSSACIRRSNNSFFSRLNWLTHLNFKYPALNVTMPNNEQFDKLYIWGVHHPGTDKDQIFLYAQSSGRITVSTKRSQQAV
IPNIGSRPRIRNIPSRISIYWTIVKPGDILLINSTGNLIAPRGYFKIRSGKSSIMRSDAPIGKCNSECITPNGSIPNDK
PFQNVNRITYGACPRYVKQSTLKLATGMRNVPEKQTRGIFGAIAGFIENGWEGMVDGWYGFRHQNSEGRGQAADLKSTQ
AAIDQINGKLNRLIGKTNEKFHQIEKEFSEVEGRIQDLEKYVEDTKIDLWSYNAELLVALENQHTIDLTDSEMNKLFEK
TKKQLRENAEDMGNGCFKIYHKCDNACIGSIRNGTYDHDVYRDEALNNRFQIKGVELKSGYKDWILWISFAISCFLLCV
ALLGFIMWACQKGNIRCNICI*

FIG. 6: B-2X35S/CPMV-HT+/ PDISP/H3 Victoria/ NOS (Construct number 1819)

FIG. 6A

IF(SacII)-Kozac_PDI.c (SEQ ID NO:24)

GTCGGGCCCAATACCGCGGAGAAAATGGCGAAAAACGTTGCGATTTTC

FIG. 6B

Schematic representation of construct 2181. SacII and StuI restriction enzyme sites used for plasmid linearization are annotated on the representation.

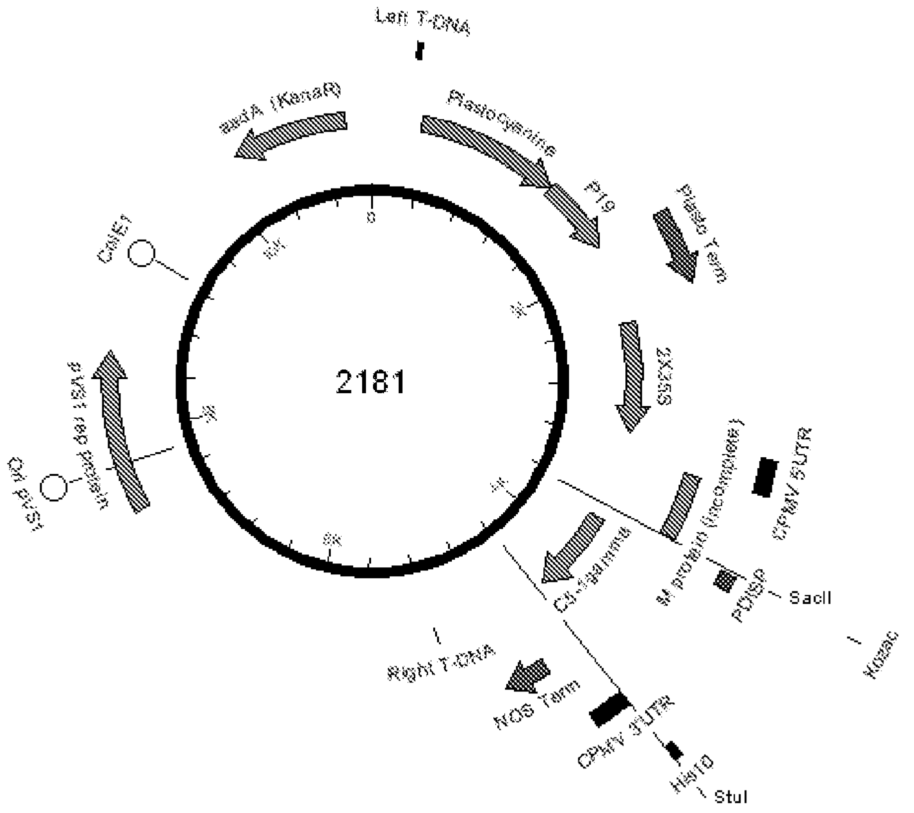

FIG. 6C,

Construct 2181 from left to right t-DNA borders (underlined). 2X35S/CPMV-HT+/NOS with Plastocyanine-P19-Plastocyanine silencing inhibitor expression cassette (SEQ ID NO: 25)

TGGCAGGATATATTGTGGTGTAAACAAATTGACGCTTAGACAACTTAATAACACATTGCGGACGTTTTTAATGTACTGA
ATTAACGCCGAATCCCGGGCTGGTATATTTATATGTTGTCAAATAACTCAAAAACCATAAAAGTTTAAGTTAGCAAGTG
TGTACATTTTTACTTGAACAAAAATATTCACCTACTACTGTTATAAATCATTATTAAACATTAGAGTAAAGAAATATGG
ATGATAAGAACAAGAGTAGTGATATTTTGACAACAATTTTGTTGCAACATTTGAGAAAATTTTGTTGTTCTCTCTTTTC
ATTGGTCAAAAACAATAGAGAGAGAAAAAGGAAGAGGGAGAATAAAAACATAATGTGAGTATGAGAGAGAAAGTTGTAC

FIG. 6C (cont.)

AAAAGTTGTACCAAAATAGTTGTACAAATATCATTGAGGAATTTGACAAAAGCTACACAAATAAGGGTTAATTGCTGTA
AATAAATAAGGATGACGCATTAGAGAGATGTACCATTAGAGAATTTTTGGCAAGTCATTAAAAAGAAAGAATAAATTAT
TTTTAAAATTAAAAGTTGAGTCATTTGATTAAACATGTGATTATTTAATGAATTGATGAAAGAGTTGGATTAAAGTTGT
ATTAGTAATTAGAATTTGGTGTCAAATTTAATTTGACATTTGATCTTTTCCTATATATTGCCCCATAGAGTCAGTTAAC
TCATTTTTATATTTCATAGATCAAATAAGAGAAATAACGGTATATTAATCCCTCCAAAAAAAAAAAACGGTATATTTAC
TAAAAAATCTAAGCCACGTAGGAGGATAACAGGATCCCCGTAGGAGGATAACATCCAATCCAACCAATCACAACAATCC
TGATGAGATAACCCACTTTAAGCCCACGCATCTGTGGCACATCTACATTATCTAAATCACACATTCTTCCACACATCTG
AGCCACACAAAAACCAATCCACATCTTTATCACCCATTCTATAAAAAATCACACTTTGTGAGTCTACACTTTGATTCCC
TTCAAACACATACAAAGAGAAGAGACTAATTAATTAATTAATCATCTTGAGAGAAAATGGAACGAGCTATACAAGGAAA
CGACGCTAGGGAACAAGCTAACAGTGAACGTTGGGATGGAGGATCAGGAGGTACCACTTCTCCCTTCAAACTTCCTGAC
GAAAGTCCGAGTTGGACTGAGTGGCGGCTACATAACGATGAGACGAATTCGAATCAAGATAATCCCCTTGGTTTCAAGG
AAAGCTGGGGTTTCGGGAAAGTTGTATTTAAGAGATATCTCAGATACGACAGGACGGAAGCTTCACTGCACAGAGTCCT
TGGATCTTGGACGGGAGATTCGGTTAACTATGCAGCATCTCGATTTTTCGGTTTCGACCAGATCGGATGTACCTATAGT
ATTCGGTTTCGAGGAGTTAGTATCACCGTTTCTGGAGGGTCGCGAACTCTTCAGCATCTCTGTGAGATGGCAATTCGGT
CTAAGCAAGAACTGCTACAGCTTGCCCCAATCGAAGTGGAAAGTAATGTATCAAGAGGATGCCCTGAAGGTACTCAAAC
CTTCGAAAAAGAAAGCGAGTAAGTTAAAATGCTTCTTCGTCTCCTATTTATAATATGGTTTGTTATTGTTAATTTTGTT
CTTGTAGAAGAGCTTAATTAATCGTTGTTGTTATGAAATACTATTTGTATGAGATGAACTGGTGTAATGTAATTCATTT
ACATAAGTGGAGTCAGAATCAGAATGTTTCCTCCATAACTAACTAGACATGAAGACCTGCCGCGTACAATTGTCTTATA
TTTGAACAACTAAAATTGAACATCTTTTGCCACAACTTTATAAGTGGTTAATATAGCTCAAATATATGGTCAAGTTCAA
TAGATTAATAATGGAAATATCAGTTATCGAAATTCATTAACAATCAACTTAACGTTATTAACTACTAATTTTATATCAT
CCCCTTTGATAAATGATAGTACACCAATTAGGAAGGAGCATGCTCGCCTAGGAGATTGTCGTTTCCCGCCTTCAGTTTG
CAAGCTGCTCTAGCCGTGTAGCCAATACGCAAACCGCCTCTCCCCGCGCGTTGGGAATTACTAGCGCGTGTCGACAAGC
TTGCATGCCGGTCAACATGGTGGAGCACGACACACTTGTCTACTCCAAAAATATCAAAGATACAGTCTCAGAAGACCAA
AGGGCAATTGAGACTTTTCAACAAAGGGTAATATCCGGAAACCTCCTCGGATTCCATTGCCCAGCTATCTGTCACTTTA
TTGTGAAGATAGTGGAAAAGGAAGGTGGCTCCTACAAATGCCATCATTGCGATAAAGGAAAGGCCATCGTTGAAGATGC
CTCTGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGTCT
CAGAAGACCAAAGGGCAATTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGCGATAAAGGAAAGGCCATC
GTTGAAGATGCCTCTGCCGACAGTGGTCCCAAAGATGGACCCCCACCCACGAGGAGCATCGTGGAAAAAGAAGACGTTC
CAACCACGTCTTCAAAGCAAGTGGATTGATGTGATATCTCCACTGACGTAAGGGATGACGCACAATCCCACTATCCTTC
GCAAGACCCTTCCTCTATATAAGGAAGTTCATTTCATTTGGAGAGGTATTAAAATCTTAATAGGTTTTGATAAAAGCGA
ACGTGGGGAAACCCGAACCAAACCTTCTTCTAAACTCTCTCTCATCTCTCTTAAAGCAAACTTCTCTCTTGTCTTTCTT
GCGTGAGCGATCTTCAACGTTGTCAGATCGTGCTTCGGCACCAGTACAACGTTTTCTTTCACTGAAGCGAAATCAAAGA
TCTCTTTGTGGACACGTAGTGCGGCGCCATTAAATAACGTGTACTTGTCCTATTCTTGTCGGTGTGGTCTTGGGAAAAG
AAAGCTTGCTGGAGGCTGCTGTTCAGCCCCATACATTACTTGTTACGATTCTGCTGACTTTCGGCGGGTGCAATATCTC
TACTTCTGCTTGACGAGGTATTGTTGCCTGTACTTCTTTCTTCTTCTTCTTGCTGATTGGTTCTATAAGAAATCTAGTA
TTTTCTTTGAAACAGAGTTTTCCCGTGGTTTTCGAACTTGGAGAAAGATTGTTAAGCTTCTGTATATTCTGCCCAAATT
TGTCGGGCCCAATACCGCGGAGAAAATGGCGAAAAACGTTGCGATTTTCGGCTTATTGTTTTCTCTTCTTGTGTTGGTT
CCTTCTCAGATCTTCGCGACGTCACTCCTCAGCCAAAACGACACCCCCATCTGTCTATCCACTGGCCCCTGGATCTGCT
GCCCAAACTAACTCCATGGTGACCCTGGGATGCCTGGTCAAGGGCTATTTCCCTGAGCCAGTGACAGTGACCTGGAACT
CTGGATCCCTGTCCAGCGGTGTGCACACCTTCCCAGCTGTCCTGCAGTCTGACCTCTACACTCTGAGCAGCTCAGTGAC
TGTCCCCTCCAGCACCTGGCCCAGCGAGACCGTCACCTGCAACGTTGCCCACCCGGCCAGCAGCACCAAGGTGGACAAG
AAAATTGTGCCCAGGGATTGTGGTTGTAAGCCTTGCATATGTACAGTCCCAGAAGTATCATCTGTCTTCATCTTCCCCC
CAAAGCCCAAGGATGTGCTCACCATTACTCTGACTCCTAAGGTCACGTGTGTTGTGGTAGACATCAGCAAGGATGATCC
CGAGGTCCAGTTCAGCTGGTTTGTAGATGATGTGGAGGTGCACACAGCTCAGACGCAACCCCGGGAGGAGCAGTTCAAC
AGCACTTTCCGCTCAGTCAGTGAACTTCCCATCATGCACCAGGACTGGCTCAATGGCAAGGAGCGATCGCTCACCATCA
CCATCACCATCACCATCACCATTAAAGGCCTATTTTCTTTAGTTTGAATTTACTGTTATTCGGTGTGCATTTCTATGTT
TGGTGAGCGGTTTTCTGTGCTCAGAGTGTGTTTATTTTATGTAATTTAATTTCTTTGTGAGCTCCTGTTTAGCAGGTCG
TCCCTTCAGCAAGGACACAAAAAGATTTTAATTTTATTAAAAAAAAAAAAAAAAAAAGACCGGGAATTCGATATCAAGCT
TATCGACCTGCAGATCGTTCAAACATTTGGCAATAAAGTTTCTTAAGATTGAATCCTGTTGCCGGTCTTGCGATGATTA
TCATATAATTTCTGTTGAATTACGTTAAGCATGTAATAATTAACATGTAATGCATGACGTTATTTATGAGATGGGTTTT
TATGATTAGAGTCCCGCAATTATACATTTAATACGCGATAGAAAACAAAATATAGCGCGCAAACTAGGATAAATTATCG
CGCGCGGTGTCATCTATGTTACTAGATCTCTAGAGTCTCAAGCTTGGCGCGCCCACGTGACTAGTGGCACTGGCCGTCG
TTTTACAACGTCGTGACTGGGAAAACCCTGGCGTTACCCAACTTAATCGCCTTGCAGCACATCCCCCTTTCGCCAGCTG

FIG. 6C (cont.)

GCGTAATAGCGAAGAGGCCCGCACCGATCGCCCTTCCCAACAGTTGCGCAGCCTGAATGGCGAATGCTAGAGCAGCTTG
AGCTTGGATCAGATTGTCGTTTCCCGCCTTCAGTTTAAACTATCAGTGTTTGACAGGATATATTGGCGGGTAAACCTAA
GAGAAAAGAGCGTTTA

FIG. 6D

Expression cassette number 1819 from 2X35S promoter to NOS terminator. PDISP/H3 Victoria nucleotide sequence is underlined. (SEQ ID NO: 26)

GTCAACATGGTGGAGCACGACACACTTGTCTACTCCAAAAATATCAAAGATACAGTCTCAGAAGACCAAAGGGCAATTG
AGACTTTTCAACAAAGGGTAATATCCGGAAACCTCCTCGGATTCCATTGCCCAGCTATCTGTCACTTTATTGTGAAGAT
AGTGGAAAAGGAAGGTGGCTCCTACAAATGCCATCATTGCGATAAAGGAAAGGCCATCGTTGAAGATGCCTCTGCCGAC
AGTGGTCCCAAAGATGGACCCCCACCCACGAGGAGCATCGTGGAAAAAGAAGACGTTCCAACCACGTCTTCAAAGCAAG
TGGATTGATGTGATAACATGGTGGAGCACGACACACTTGTCTACTCCAAAAATATCAAAGATACAGTCTCAGAAGACCA
AAGGGCAATTGAGACTTTTCAACAAAGGGTAATATCCGGAAACCTCCTCGGATTCCATTGCCCAGCTATCTGTCACTTT
ATTGTGAAGATAGTGGAAAAGGAAGGTGGCTCCTACAAATGCCATCATTGCGATAAAGGAAAGGCCATCGTTGAAGATG
CCTCTGCCGACAGTGGTCCCAAAGATGGACCCCCACCCACGAGGAGCATCGTGGAAAAAGAAGACGTTCCAACCACGTC
TTCAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGAA
ACCCGAACCAAACCTTCTTCTAAACTCTCTCTCATCTCTCTTAAAGCAAACTTCTCTCTTGTCTTTCTTGCGTGAGCGA
TCTTCAACGTTGTCAGATCGTGCTTCGGCACCAGTACAACGTTTTCTTTCACTGAAGCGAAATCAAAGATCTCTTTGTG
GACACGTAGTGCGGCGCCATTAAATAACGTGTACTTGTCCTATTCTTGTCGGTGTGGTCTTGGGAAAAGAAAGCTTGCT
GGAGGCTGCTGTTCAGCCCCATACATTACTTGTTACGATTCTGCTGACTTTCGGCGGGTGCAATATCTCTACTTCTGCT
TGACGAGGTATTGTTGCCTGTACTTCTTTCTTCTTCTTCTTGCTGATTGGTTCTATAAGAAATCTAGTATTTTCTTTGA
AACAGAGTTTTCCCGTGGTTTTCGAACTTGGAGAAAGATTGTTAAGCTTCTGTATATTCTGCCCAAATTTGTCGGGCCC
AATACCGCGGAGAAAATGGCGAAAAACGTTGCGATTTTCGGCTTATTGTTTTCTCTTCTTGTGTTGGTTCCTTCTCAGA
TCTTCGCCCAAAAACTTCCTGGAAATGACAACAGCACGGCAACGCTGTGCCTTGGGCACCATGCAGTACCAAACGGAAC
GATAGTGAAAACAATCACGAATGACCAAATTGAAGTTACTAATGCTACTGAGCTGGTTCAGAATTCCTCAATAGGTGAA
ATATGCGACAGTCCTCATCAGATCCTTGATGGAGAAAACTGCACACTAATAGATGCTCTATTGGGAGACCCTCAGTGTG
ATGGCTTCCAAAATAAGAAATGGGACCTTTTTGTTGAACGAAGCAAAGCCTACAGCAACTGTTACCCTTATGATGTGCC
GGATTATGCCTCCCTTAGGTCACTAGTTGCCTCATCCGGCACACTGGAGTTTAACAATGAAAGCTTCAATTGGACTGGA
GTCACTCAAAACGGAACAAGTTCTGCTTGCATAAGGAGATCTAATAATAGTTTCTTTAGTAGATTAAATTGGTTGACCC
ACTTAAACTTCAAATACCCAGCATTGAACGTGACTATGCCAAACAATGAACAATTTGACAAATTGTACATTTGGGGGGT
TCACCACCCGGGTACGGACAAGGACCAAATCTTCCTGTATGCTCAATCATCAGGAAGAATCACAGTATCTACCAAAAGA
AGCCAACAAGCTGTAATCCCGAATATCGGATCTAGACCCAGAATAAGGAATATCCCTAGCAGAATAAGCATCTATTGGA
CAATAGTAAAACCGGGAGACATACTTTTGATTAACAGCACAGGGAATCTAATTGCTCCTAGGGGTTACTTCAAAATACG
AAGTGGGAAAAGCTCAATAATGAGATCAGATGCACCCATTGGCAAATGCAATTCTGAATGCATCACTCCAAATGGAAGC
ATTCCCAATGACAAACCATTCCAAAATGTAAACAGGATCACATACGGGGCCTGTCCCAGATATGTTAAGCAAAGCACTC
TGAAATTGGCAACAGGAATGCGAAATGTACCAGAGAAACAAACTAGAGGCATATTTGGCGCAATAGCGGGTTTCATAGA
AAATGGTTGGGAGGGAATGGTGGATGGTTGGTACGGTTTCAGGCATCAAAATTCTGAGGGAAGAGGACAAGCAGCAGAT
CTCAAAAGCACTCAAGCAGCAATCGATCAAATCAATGGGAAGCTGAATCGATTGATCGGGAAAACCAACGAGAAATTCC
ATCAGATTGAAAAAGAATTCTCAGAAGTCGAAGGGAGAATTCAGGACCTTGAGAAATATGTTGAGGACACTAAAATAGA
TCTCTGGTCATACAACGCGGAGCTTCTTGTTGCCCTGGAGAACCAACATACAATTGATCTAACTGACTCAGAAATGAAC
AAACTGTTTGAAAAAACAAAGAAGCAACTAAGGGAAAATGCTGAGGATATGGGCAATGGTTGTTTCAAAATATACCACA
AATGTGACAATGCCTGCATAGGATCAATCAGAAATGGAACTTATGACCACGATGTATACAGAGATGAAGCATTAAACAA
CCGGTTCCAGATCAAGGGAGTTGAGCTGAAGTCAGGGTACAAAGATTGGATCCTATGGATTTCCTTTGCCATATCATGT
TTTTTGCTTTGTGTTGCTTTGTTGGGGTTCATCATGTGGGCCTGCCAAAAGGGCAACATTAGGTGCAACATTTGCATTT
GAAGGCCTATTTTCTTTAGTTTGAATTTACTGTTATTCGGTGTGCATTTCTATGTTTGGTGAGCGGTTTTCTGTGCTCA
GAGTGTGTTTATTTTATGTAATTTAATTTCTTTGTGAGCTCCTGTTTAGCAGGTCGTCCCTTCAGCAAGGACACAAAAA
GATTTTAATTTTATTAAAAAAAAAAAAAAAAAAGACCGGGAATTCGATATCAAGCTTATCGACCTGCAGATCGTTCAAA
CATTTGGCAATAAAGTTTCTTAAGATTGAATCCTGTTGCCGGTCTTGCGATGATTATCATATAATTTCTGTTGAATTAC
GTTAAGCATGTAATAATTAACATGTAATGCATGACGTTATTTATGAGATGGGTTTTTATGATTAGAGTCCCGCAATTAT
ACATTTAATACGCGATAGAAAACAAAATATAGCGCGCAAACTAGGATAAATTATCGCGCGCGGTGTCATCTATGTTACT
AGAT

Schematic representation of construct number 1819

Figure 7: E-Variation of sequence between SacII restriction site and ATG of PDISP/H3 Victoria in 2X35S/CPMV HT+/NOS expression system

Figure 7A (SEQ ID NO:27) IF-HT1*-PDI.c (modified sequence from original 1819 construct underlined)

GTCGGGCCCAATACCGCGGAGACAATGGCGAAAAACGTTGCGATTTTCGGCT

Figure 7B (SEQ ID NO:28) IF-HT2*-PDI.c (modified sequence from original 1819 construct underlined)

GTCGGGCCCAATACCGCGGAGGAAATGGCGAAAAACGTTGCGATTTTCGGCT

Figure 7C (SEQ ID NO:29) IF-HT3*-PDI.c (modified sequence from original 1819 construct underlined)

GTCGGGCCCAATACCGCGGAAAAAATGGCGAAAAACGTTGCGATTTTCGGCT

Figure 7D (SEQ ID NO:30) IF-HT4*-PDI.c (modified sequence from original 1819 construct underlined)

GTCGGGCCCAATACCGCGGAAACAATGGCGAAAAACGTTGCGATTTTCGGCT

Figure 7E (SEQ ID NO:31) IF-HT5*-PDI.c (modified sequence from original 1819 construct underlined)

GTCGGGCCCAATACCGCGGAAGCAATGGCGAAAAACGTTGCGATTTTCGGCT

Figure 7F (SEQ ID NO:32) IF-HT6*-PDI.c (modified sequence from original 1819 construct underlined)

GTCGGGCCCAATACCGCGGAAGAAATGGCGAAAAACGTTGCGATTTTCGGCT

Figure 7G (SEQ ID NO:33) IF-HT7*-PDI.c (modified sequence from original 1819 construct underlined)

GTCGGGCCCAATACCGCGGAAAGAAATGGCGAAAAACGTTGCGATTTTCGGCT

Figure 7H (SEQ ID NO:34) IF-HT8*-PDI.c (modified sequence from original 1819 construct underlined)

GTCGGGCCCAATACCGCGGAAAAGAAATGGCGAAAAACGTTGCGATTTTCGGCT

Figure 7I Schematic representation of construct number 1952. Analogous features were used to prepare constructs 1953-1959..
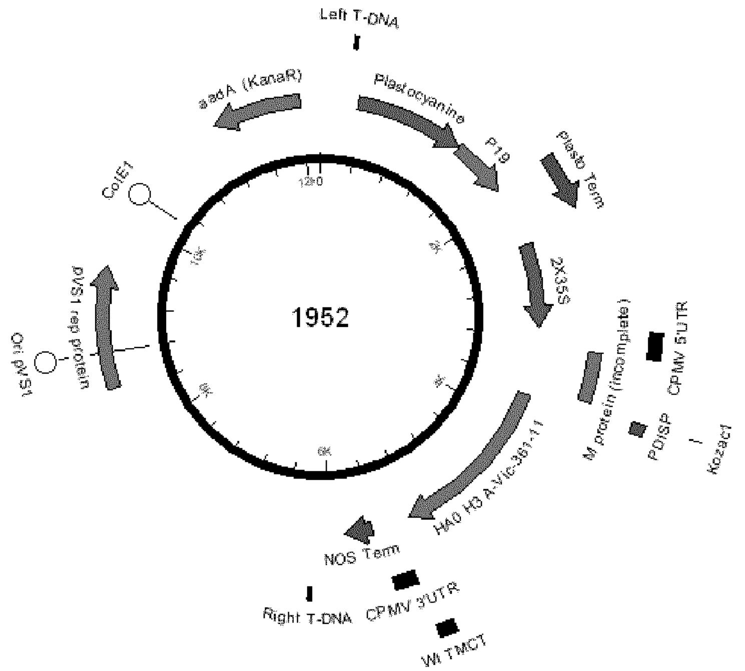

Figure 8: G- 2X35S/CPMV HT (construct no 484) and HT+ (construct no 1805) for PDISP/H1 California

Figure 8A (SEQ ID NO: 35)

Nucleotide sequence of PDISP/H1 California.

ATGGCGAAAAACGTTGCGATTTTCGGCTTATTGTTTTCTCTTCTTGTGTTGGTTCCTTCTCAGATCTTCGCTGACACATTATGTATAG
GTTATCATGCGAACAATTCAACAGACACTGTAGACACAGTACTAGAAAAGAATGTAACAGTAACACACTCTGTTAACCTTCTAGAA
GACAAGCATAACGGGAAACTATGCAAACTAAGAGGGGTAGCCCCATTGCATTTGGGTAAATGTAACATTGCTGGCTGGATCCTGG
GAAATCCAGAGTGTGAATCACTCTCCACAGCAAGCTCATGGTCCTACATTGTGGAAACACCTAGTTCAGACAATGGAACGTGTTAC
CCAGGAGATTTCATCGATTATGAGGAGCTAAGAGAGCAATTGAGCTCAGTGTCATCATTTGAAAGGTTTGAGATATTCCCCAAGA
CAAGTTCATGGCCCAATCATGACTCGAACAAAGGTGTAACGGCAGCATGTCCTCATGCTGGAGCAAAAAGCTTCTACAAAAATTT
AATATGGCTAGTTAAAAAAGGAAATTCATACCCAAAGCTCAGCAAATCCTACATTAATGATAAAGGGAAAGAAGTCCTCGTGCTA
TGGGGCATTCACCATCCATCTACTAGTGCTGACCAACAAAGTCTCTATCAGAATGCAGATGCATATGTTTTTGTGGGGTCATCAAG
ATACAGCAAGAAGTTCAAGCCGGAAATAGCAATAAGACCCAAAGTGAGGGATCAAGAAGGGAGAATGAACTATTACTGGACACT
AGTAGAGCCGGGAGACAAAATAACATTCGAAGCAACTGGAAATCTAGTGGTACCGAGATATGCATTCGCAATGGAAAGAAATGC
TGGATCTGGTATTATCATTTCAGATACACCAGTCCACGATTGCAATACAACTTGTCAAACACCCAAGGGTGCTATAAACACCAGCC
TCCCATTTCAGAATATACATCCGATCACAATTGGAAAATGTCCAAAATATGTAAAAAGCACAAAATTGAGACTGGCCACAGGATTG
AGGAATATCCCGTCTATTCAATCTAGAGGACTATTTGGGGCCATTGCCGGTTTCATTGAAGGGGGGTGGACAGGGATGGTAGAT
GGATGGTACGGTTATCACCATCAAAATGAGCAGGGGTCAGGATATGCAGCCGACCTGAAGAGCACACAGAATGCCATTGACGAG
ATTACTAACAAAGTAAATTCTGTTATTGAAAAGATGAATACACAGTTCACAGCAGTAGGTAAAGAGTTCAACCACCTGGAAAAAA
GAATAGAGAATTTAAATAAAAAAGTTGATGATGGTTTCCTGGACATTTGGACTTACAATGCCGAACTGTTGGTTCTATTGGAAAAT
GAAAGAACTTTGGACTACCACGATTCAAATGTGAAGAACTTATATGAAAAGGTAAGAAGCCAGCTAAAAAACAATGCCAAGGAA
ATTGGAAACGGCTGCTTTGAATTTTACCACAAATGCGATAACACGTGCATGGAAAGTGTCAAAAATGGGACTTATGACTACCCAA
AATACTCAGAGGAAGCAAAATTAAACAGAGAAGAAATAGATGGGGTAAAGCTGGAATCAACAAGGATTTACCAGATTTTGGCGA
TCTATTCAACTGTCGCCAGTTCATTGGTACTGGTAGTCTCCCTGGGGGCAATCAGTTTCTGGATGTGCTCTAATGGGTCTCTACAGT
GTAGAATATGTATTTAA

Figure 8B (SEQ ID NO :36)

Amino acid sequence of PDISP/H1 California.

MAKNVAIFGLLFSLLVLVPSQIFADTLCIGYHANNSTDTVDTVLEKNVTVTHSVNLLEDKHNGKLCKLRGVAPLHLGKCNIAGWILGNPE
CESLSTASSWSYIVETPSSDNGTCYPGDFIDYEELREQLSSVSSFERFEIFPKTSSWPNHDSNKGVTAACPHAGAKSFYKNLIWLVKKGNS
YPKLSKSYINDKGKEVLVLWGIHHPSTSADQQSLYQNADAYVFVGSSRYSKKFKPEIAIRPKVRDQEGRMNYYWTLVEPGDKITFEATGN
LVVPRYAFAMERNAGSGIIISDTPVHDCNTTCQTPKGAINTSLPFQNIHPITIGKCPKYVKSTKLRLATGLRNIPSIQSRGLFGAIAGFIEGG
WTGMVDGWYGYHHQNEQGSGYAADLKSTQNAIDEITNKVNSVIEKMNTQFTAVGKEFNHLEKRIENLNKKVDDGFLDIWTYNAELL
VLLENERTLDYHDSNVKNLYEKVRSQLKNNAKEIGNGCFEFYHKCDNTCMESVKNGTYDYPKYSEEAKLNREEIDGVKLESTRIYQILAIYS
TVASSLVLVVSLGAISFWMCSNGSLQCRICI*

Figure 8C Schematic representation of construct number 484 (2X35S/CPMV HT)
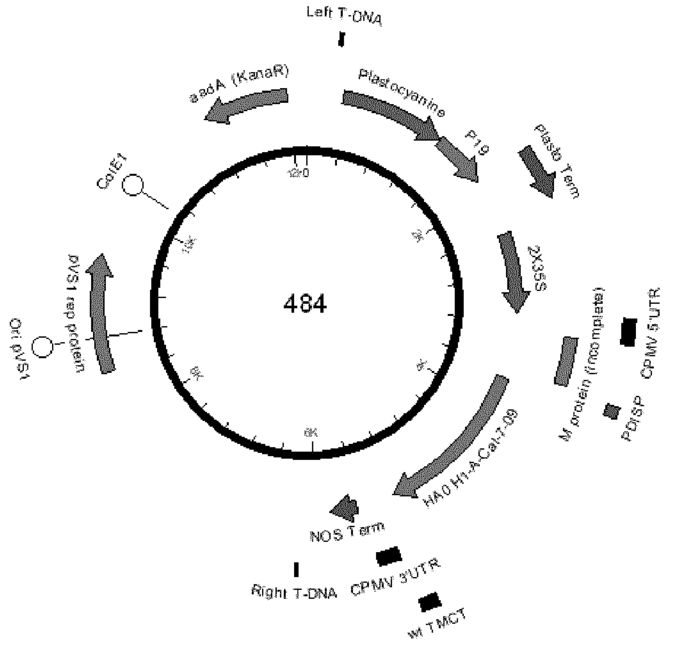
Figure 8D Schematic representation of construct number 1805 (2X35S/CPMV HT+)
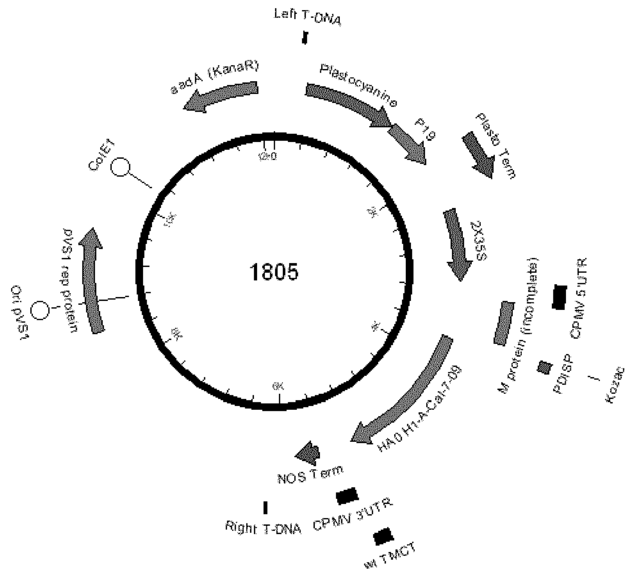

Figure 9: H - 2X35S/CPMV HT (construct no 409) and HT+ (construct no 2319) for H5

Indonesia

FIGURE 9A, (SEQ ID NO: 37)

Nucleotide sequence of PDISP/H5 Indonesia

ATGGCGAAAAACGTTGCGATTTTCGGCTTATTGTTTTCTCTTCTTGTGTTGGTTCCTTCTCAGATCTTCGCCGATCAGATTTGCATTG
GTTACCATGCAAACAATTCAACAGAGCAGGTTGACACAATCATGGAAAAGAACGTTACTGTTACACATGCCCAAGACATACTGGA
AAAGACACACAACGGGAAGCTCTGCGATCTAGATGGAGTGAAGCCTCTAATTTTAAGAGATTGTAGTGTAGCTGGATGGCTCCTC
GGGAACCCAATGTGTGACGAATTCATCAATGTACCGGAATGGTCTTACATAGTGGAGAAGGCCAATCCAACCAATGACCTCTGTT
ACCCAGGGAGTTTCAACGACTATGAAGAACTGAAACACCTATTGAGCAGAATAAACCATTTTGAGAAAATTCAAATCATCCCCAAA
AGTTCTTGGTCCGATCATGAAGCCTCATCAGGAGTTAGCTCAGCATGTCCATACCTGGGAAGTCCCTCCTTTTTTAGAAATGTGGT
ATGGCTTATCAAAAAGAACAGTACATACCCAACAATAAAGAAAAGCTACAATAATACCAACCAAGAGGATCTTTTGGTACTGTGG
GGAATTCACCATCCTAATGATGCGGCAGAGCAGACAAGGCTATATCAAAACCCAACCACCTATATTTCCATTGGGACATCAACACT
AAACCAGAGATTGGTACCAAAAATAGCTACTAGATCCAAAGTAAACGGGCAAAGTGGAAGGATGGAGTTCTTCTGGACAATTTTA
AAACCTAATGATGCAATCAACTTCGAGAGTAATGGAAATTTCATTGCTCCAGAATATGCATACAAAATTGTCAAGAAAGGGGACTC
AGCAATTATGAAAAGTGAATTGGAATATGGTAACTGCAACACCAAGTGTCAAACTCCAATGGGGGCGATAAACTCTAGTATGCCA
TTCCACAACATACACCCTCTCACCATCGGGGAATGCCCCAAATATGTGAAATCAAACAGATTAGTCCTTGCAACAGGGCTCAGAAA
TAGCCCTCAAAGAGAGAGCAGAAGAAAAAAGAGAGGACTATTTGGAGCTATAGCAGGTTTTATAGAGGGAGGATGGCAGGGAA
TGGTAGATGGTTGGTATGGGTACCACCATAGCAATGAGCAGGGGAGTGGGTACGCTGCAGACAAAGAATCCACTCAAAAGGCAA
TAGATGGAGTCACCAATAAGGTCAACTCAATCATTGACAAAATGAACACTCAGTTTGAGGCCGTTGGAAGGGAATTTAATAACTT
AGAAAGGAGAATAGAGAATTTAAACAAGAAGATGGAAGACGGGTTTCTAGATGTCTGGACTTATAATGCCGAACTTCTGGTTCTC
ATGGAAAATGAGAGAACTCTAGACTTTCATGACTCAAATGTTAAGAACCTCTACGACAAGGTCCGACTACAGCTTAGGGATAATG
CAAAGGAGCTGGGTAACGGTTGTTTCGAGTTCTATCACAAATGTGATAATGAATGTATGGAAAGTATAAGAAACGGAACGTACAA
CTATCCGCAGTATTCAGAAGAAGCAAGATTAAAAAGAGAGGAAATAAGTGGGGTAAAATTGGAATCAATAGGAACTTACCAAAT
ACTGTCAATTTATTCAACAGTGGCGAGTTCCCTAGCACTGGCAATCATGATGGCTGGTCTATCTTTATGGATGTGCTCCAATGGATC
GTTACAATGCAGAATTTGCATT

FIGURE 9B, (SEQ ID NO: 38)

Amino acid sequence of PDISP/H5 Indonesia

MAKNVAIFGLLFSLLVLVPSQIFADQICIGYHANNSTEQVDTIMEKNVTVTHAQDILEKTHNGKLCDLDGVKPLILRDCSVAGWLLGNP
MCDEFINVPEWSYIVEKANPTNDLCYPGSFNDYEELKHLLSRINHFEKIQIIPKSSWSDHEASSGVSSACPYLGSPSFFRNVVWLIKKNSTY
PTIKKSYNNTNQEDLLVLWGIHHPNDAAEQTRLYQNPTTYISIGTSTLNQRLVPKIATRSKVNGQSGRMEFFWTILKPNDAINFESNGNF
IAPEYAYKIVKKGDSAIMKSELEYGNCNTKCQTPMGAINSSMPFHNIHPLTIGECPKYVKSNRLVLATGLRNSPQRESRRKKRGLFGAIAG
FIEGGWQGMVDGWYGYHHSNEQGSGYAADKESTQKAIDGVTNKVNSIIDKMNTQFEAVGREFNNLERRIENLNKKMEDGFLDVWT
YNAELLVLMENERTLDFHDSNVKNLYDKVRLQLRDNAKELGNGCFEFYHKCDNECMESIRNGTYNYPQYSEEARLKREEISGVKLESIGT
YQILSIYSTVASSLALAIMMAGLSLWMCSNGSLQCRICI

Figure 9C Schematic representation of construct number 489 (2X35S/CPMV HT)
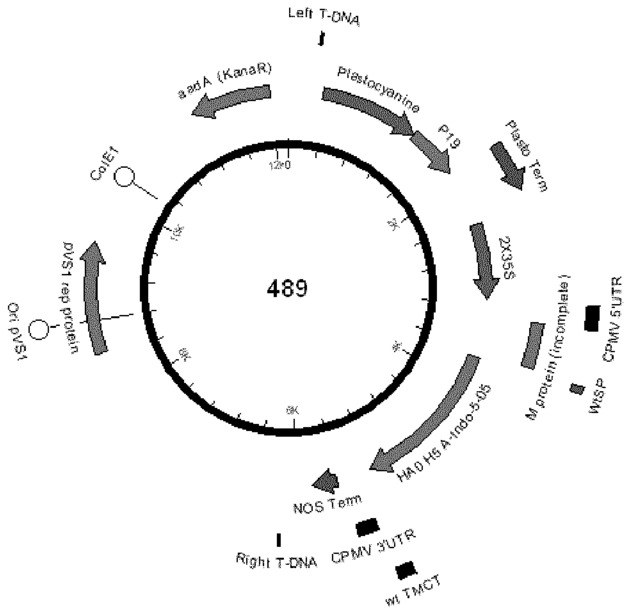
Figure 9D Schematic representation of construct number 1889 (2X35S/CPMV HT+)
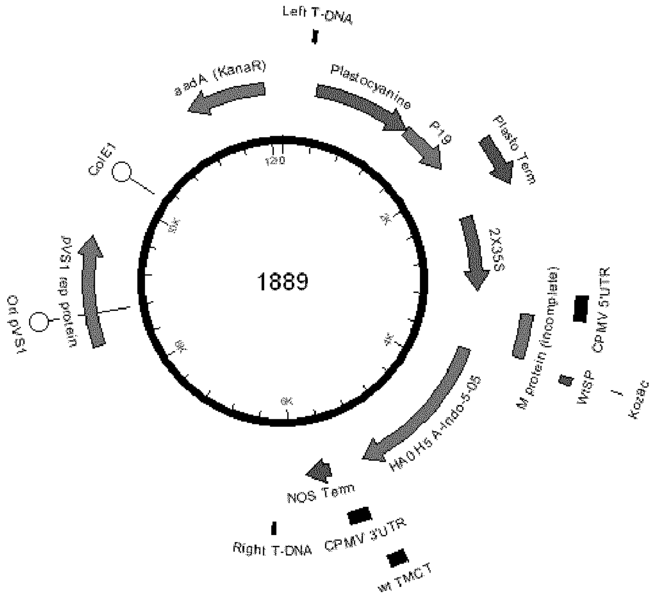

Figure 10: I- 2X35S/CPMV HT (construct no 2140) and HT+ (construct no 2142) for PDISP/H7 Hangzhou

Figure 10A (SEQ ID NO : 39)

Nucleotide sequence of PDISP/H7 Hangzhou.

ATGGCGAAAAACGTTGCGATTTTCGGCTTATTGTTTTCTCTTCTTGTGTTGGTTCCTTCTCAGATCTTCGCGGACAAAATCTGCCTCG
GACATCATGCCGTGTCAAACGGAACCAAAGTAAACACATTAACTGAAAGAGGAGTGGAAGTCGTCAATGCAACTGAAACAGTGG
AACGAACAAACATCCCCAGGATCTGCTCAAAAGGGAAAAGGACAGTTGACCTCGGTCAATGTGGACTCCTGGGGACAATCACTG
GACCACCTCAATGTGACCAATTCCTAGAATTTTCAGCCGATTTAATTATTGAGAGGCGAGAAGGAAGTGATGTCTGTTATCCTGGG
AAATTCGTGAATGAAGAAGCTCTGAGGCAAATTCTCAGAGAATCAGGCGGAATTGACAAGGAAGCAATGGGATTCACATACAGT
GGAATAAGAACTAATGGAGCAACCAGTGCATGTAGGAGATCAGGATCTTCATTCTATGCAGAAATGAAATGGCTCCTGTCAAACA
CAGATAATGCTGCATTCCCGCAGATGACTAAGTCATATAAAAATACAAGAAAAAGCCCAGCTCTAATAGTATGGGGGATCCATCA
TTCCGTATCAACTGCAGAGCAAACCAAGCTATATGGGAGTGGAAACAAACTGGTGACAGTTGGGAGTTCTAATTATCAACAATCT
TTTGTACCGAGTCCAGGAGCGAGACCACAAGTTAATGGTATATCTGGAAGAATTGACTTTCATTGGCTAATGCTAAATCCCAATGA
TACAGTCACTTTCAGTTTCAATGGGGCTTTCATAGCTCCAGACCGTGCAAGCTTCCTGAGAGGAAAATCTATGGGAATCCAGAGTG
GAGTACAGGTTGATGCCAATTGTGAAGGGGACTGCTATCATAGTGGAGGGACAATAATAAGTAACTTGCCATTTCAGAACATAGA
TAGCAGGGCAGTTGGAAAATGTCCGAGATATGTTAAGCAAAGGAGTCTGCTGCTAGCAACAGGGATGAAGAATGTTCCTGAGAT
TCCAAAGGGAAGAGGCCTATTTGGTGCTATAGCGGGTTTCATTGAAAATGGATGGGAAGGCCTAATTGATGGTTGGTATGGTTTC
AGACACCAGAATGCACAGGGAGAGGGAACTGCTGCAGATTACAAAAGCACTCAATCGGCAATTGATCAAATAACAGGAAAATTA
AACCGGCTTATAGAAAAAACCAACCAACAATTTGAGTTGATCGACAATGAATTCAATGAGGTAGAGAAGCAAATCGGTAATGTGA
TAAATTGGACCAGAGATTCTATAACAGAAGTGTGGTCATACAATGCTGAACTCTTGGTAGCAATGGAGAACCAGCATACAATTGA
TCTGGCTGATTCAGAAATGGACAAACTGTACGAACGAGTGAAAAGACAGCTGAGAGAGAATGCTGAAGAAGATGGCACTGGTTG
CTTTGAAATATTTCACAAGTGTGATGATGACTGTATGGCCAGTATTAGAAATAACACCTATGATCACAGCAAATACAGGGAAGAG
GCAATGCAAAATAGAATACAGATTGACCCAGTCAAACTAAGCAGCGGCTACAAAGATGTGATACTTTGGTTTAGCTTCGGGGCAT
CATGTTTCATACTTCTAGCCATTGTAATGGGCCTTGTCTTCATATGTGTAAAGAATGGAAACATGCGGTGCACTATTTGTATATAA

Figure 10B (SEQ ID NO :40)

Amino acid sequence of PDISP/H7 Hangzhou.

MAKNVAIFGLLFSLLVLVPSQIFADKICLGHHAVSNGTKVNTLTERGVEVVNATETVERTNIPRICSKGKRTVDLGQCGLLGTITGPPQCD
QFLEFSADLIIERREGSDVCYPGKFVNEEALRQILRESGGIDKEAMGFTYSGIRTNGATSACRRSGSSFYAEMKWLLSNTDNAAFPQMTK
SYKNTRKSPALIVWGIHHSVSTAEQTKLYGSGNKLVTVGSSNYQQSFVPSPGARPQVNGISGRIDFHWLMLNPNDTVTFSFNGAFIAPD
RASFLRGKSMGIQSGVQVDANCEGDCYHSGGTIISNLPFQNIDSRAVGKCPRYVKQRSLLLATGMKNVPEIPKGRGLFGAIAGFIENGW
EGLIDGWYGFRHQNAQGEGTAADYKSTQSAIDQITGKLNRLIEKTNQQFELIDNEFNEVEKQIGNVINWTRDSITEVWSYNAELLVAME
NQHTIDLADSEMDKLYERVKRQLRENAEEDGTGCFEIFHKCDDDCMASIRNNTYDHSKYREEAMQNRIQIDPVKLSSGYKDVILWFSFG
ASCFILLAIVMGLVFICVKNGNMRCTICI*

Figure 10C Schematic representation of construct number 2140 (2X35S/CPMV HT)
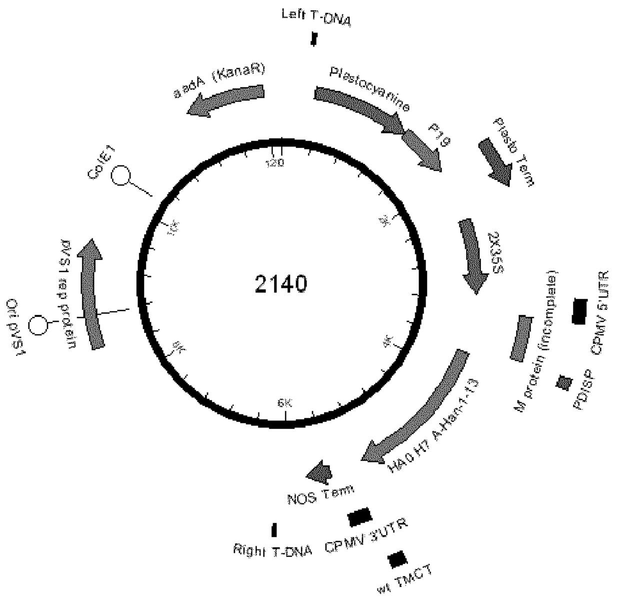
Figure 10D Schematic representation of construct number 2142 (2X35S/CPMV HT+)
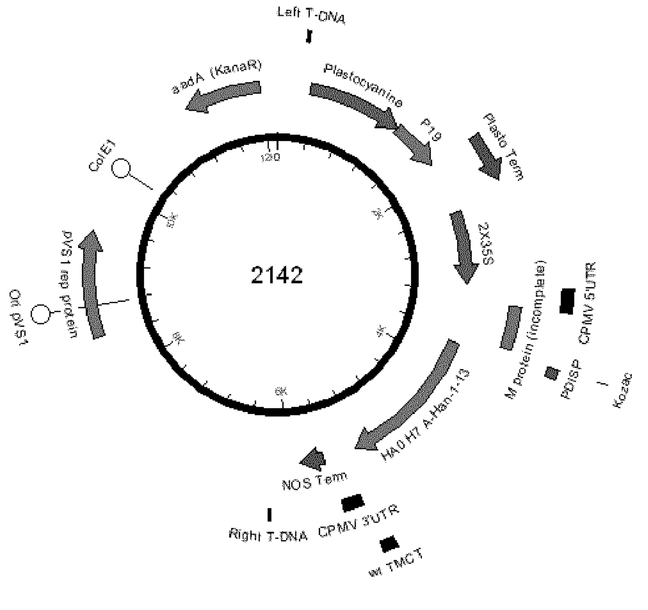

Figure 11: - 2X35S/CPMV HT (construct no 2130) and HT+ (construct no 2146) for PDISP/H7 Hangzhou+H5 Indonesia TMCT

Figure 11A (SEQ ID NO : 41)

Nucleotide sequence of PDISP/H7 Hangzhou+H5 Indonesia TMCT.

ATGGCGAAAAACGTTGCGATTTTCGGCTTATTGTTTTCTCTTCTTGTGTTGGTTCCTTCTCAGATCTTCGCGGACAAAATCTGCCTCG
GACATCATGCCGTGTCAAACGGAACCAAAGTAAACACATTAACTGAAAGAGGAGTGGAAGTCGTCAATGCAACTGAAACAGTGG
AACGAACAAACATCCCCAGGATCTGCTCAAAAGGGAAAAGGACAGTTGACCTCGGTCAATGTGGACTCCTGGGGACAATCACTG
GACCACCTCAATGTGACCAATTCCTAGAATTTTCAGCCGATTTAATTATTGAGAGGCGAGAAGGAAGTGATGTCTGTTATCCTGGG
AAATTCGTGAATGAAGAAGCTCTGAGGCAAATTCTCAGAGAATCAGGCGGAATTGACAAGGAAGCAATGGGATTCACATACAGT
GGAATAAGAACTAATGGAGCAACCAGTGCATGTAGGAGATCAGGATCTTCATTCTATGCAGAAATGAAATGGCTCCTGTCAAACA
CAGATAATGCTGCATTCCCGCAGATGACTAAGTCATATAAAAATACAAGAAAAAGCCCAGCTCTAATAGTATGGGGGATCCATCA
TTCCGTATCAACTGCAGAGCAAACCAAGCTATATGGGAGTGGAAACAAACTGGTGACAGTTGGGAGTTCTAATTATCAACAATCT
TTTGTACCGAGTCCAGGAGCGAGACCACAAGTTAATGGTATATCTGGAAGAATTGACTTTCATTGGCTAATGCTAAATCCCAATGA
TACAGTCACTTTCAGTTTCAATGGGGCTTTCATAGCTCCAGACCGTGCAAGCTTCCTGAGAGGAAAATCTATGGGAATCCAGAGTG
GAGTACAGGTTGATGCCAATTGTGAAGGGGACTGCTATCATAGTGGAGGGACAATAATAAGTAACTTGCCATTTCAGAACATAGA
TAGCAGGGCAGTTGGAAAATGTCCGAGATATGTTAAGCAAAGGAGTCTGCTGCTAGCAACAGGGATGAAGAATGTTCCTGAGAT
TCCAAAGGGAAGAGGCCTATTTGGTGCTATAGCGGGTTTCATTGAAAATGGATGGGAAGGCCTAATTGATGGTTGGTATGGTTTC
AGACACCAGAATGCACAGGGAGAGGGAACTGCTGCAGATTACAAAAGCACTCAATCGGCAATTGATCAAATAACAGGAAAATTA
AACCGGCTTATAGAAAAAACCAACCAACAATTTGAGTTGATCGACAATGAATTCAATGAGGTAGAGAAGCAAATCGGTAATGTGA
TAAATTGGACCAGAGATTCTATAACAGAAGTGTGGTCATACAATGCTGAACTCTTGGTAGCAATGGAGAACCAGCATACAATTGA
TCTGGCTGATTCAGAAATGGACAAACTGTACGAACGAGTGAAAAGACAGCTGAGAGAGAATGCTGAAGAAGATGGCACTGGTTG
CTTTGAAATATTTCACAAGTGTGATGATGACTGTATGGCCAGTATTAGAAATAACACCTATGATCACAGCAAATACAGGGAAGAG
GCAATGCAAAATAGAATACAGATTGACCCAGTCAAACTAAGCAGCGGCTACCAAATACTGTCAATTTATTCAACAGTGGCGAGTTC
CCTAGCACTGGCAATCATGATGGCTGGTCTATCTTTATGGATGTGCTCCAATGGATCGTTACAATGCAGAATTTGCATTTAA

Figure 11B (SEQ ID NO : 42)

Amino acid sequence of PDISP/H7 Hangzhou+H5 Indonesia TMCT.

MAKNVAIFGLLFSLLVLVPSQIFADKICLGHHAVSNGTKVNTLTERGVEVVNATETVERTNIPRICSKGKRTVDLGQCGLLGTITGPPQCD
QFLEFSADLIIERREGSDVCYPGKFVNEEALRQILRESGGIDKEAMGFTYSGIRTNGATSACRRSGSSFYAEMKWLLSNTDNAAFPQMTK
SYKNTRKSPALIVWGIHHSVSTAEQTKLYGSGNKLVTVGSSNYQQSFVPSPGARPQVNGISGRIDFHWLMLNPNDTVTFSFNGAFIAPD
RASFLRGKSMGIQSGVQVDANCEGDCYHSGGTIISNLPFQNIDSRAVGKCPRYVKQRSLLLATGMKNVPEIPKGRGLFGAIAGFIENGW
EGLIDGWYGFRHQNAQGEGTAADYKSTQSAIDQITGKLNRLIEKTNQQFELIDNEFNEVEKQIGNVINWTRDSITEVWSYNAELLVAME
NQHTIDLADSEMDKLYERVKRQLRENAEEDGTGCFEIFHKCDDDCMASIRNNTYDHSKYREEAMQNRIQIDPVKLSSGYQILSIYSTVAS
SLALAIMMAGLSLWMCSNGSLQCRICI*

Figure 11C Schematic representation of construct number 2130 (2X35S/CPMV HT)
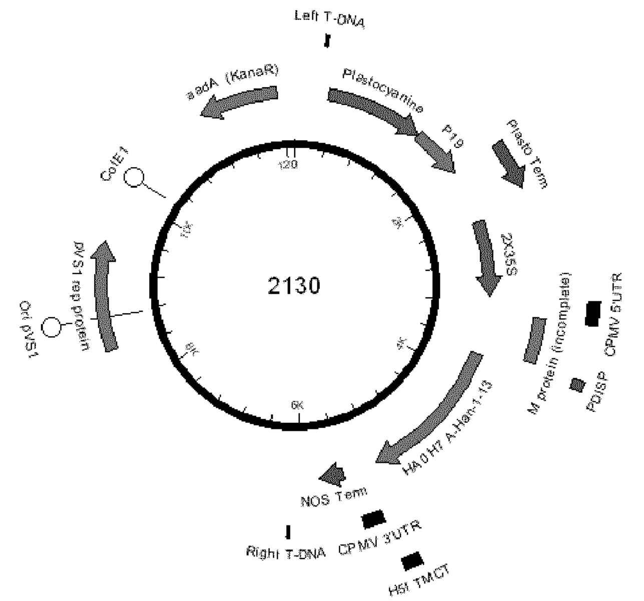
Figure 11D Schematic representation of construct number 2146 (2X35S/CPMV HT+)
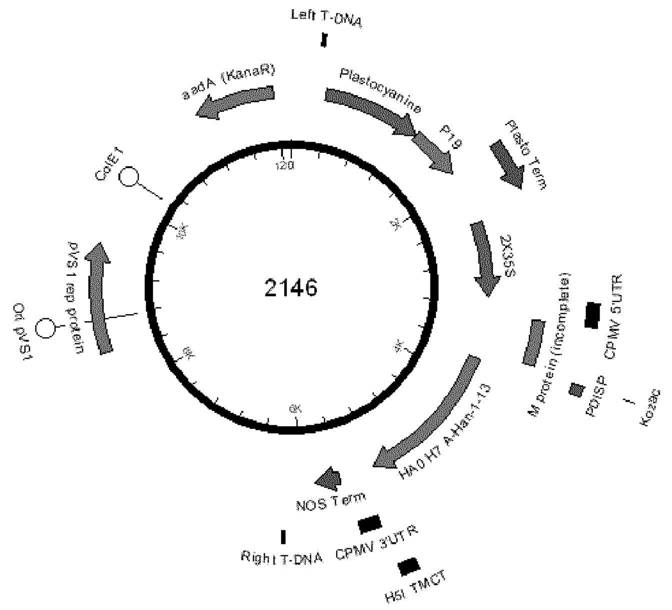

Figure 12: K- 2X35S/CPMV HT (construct no 1039) and HT+ (construct no 1829) for PDISP/HA B Brisbane (PrL-)

Figure 12A (SEQ ID NO : 43)

Nucleotide sequence of PDISP/HA B Brisbane (PrL-).

ATGGCGAAAAACGTTGCGATTTTCGGCTTATTGTTTTCTCTTCTTGTGTTGGTTCCTTCTCAGATCTTCGCCGATCGAATCTGCACTG
GAATAACATCGTCAAACTCACCACATGTCGTCAAAACTGCTACTCAAGGGGAGGTCAATGTGACTGGTGTAATACCACTGACAAC
AACACCCACCAAATCTCATTTTGCAAATCTCAAAGGAACAGAAACCAGGGGGAAACTATGCCCAAAATGCCTCAACTGCACAGAT
CTGGACGTAGCCTTGGGCAGACCAAAATGCACGGGGAAAATACCCTCGGCAAGAGTTTCAATACTCCATGAAGTCAGACCTGTTA
CATCTGGGTGCTTTCCTATAATGCACGACAGAACAAAAATTAGACAGCTGCCTAACCTTCTCCGAGGATACGAACATATCAGGTTA
TCAACCCATAACGTTATCAATGCAGAAAATGCACCAGGAGGACCCTACAAAATTGGAACCTCAGGGTCTTGCCCTAACATTACCAA
TGGAAACGGATTTTTCGCAACAATGGCTTGGGCCGTCCCAAAAAACGACAAAAACAAAACAGCAACAAATCCATTAACAATAGAA
GTACCATACATTTGTACAGAAGGAGAAGACCAAATTACCGTTTGGGGGTTCCACTCTGACAACGAGACCCAAATGGCAAAGCTCT
ATGGGGACTCAAAGCCCCAGAAGTTCACCTCATCTGCCAACGGAGTGACCACACATTACGTTTCACAGATTGGTGGCTTCCCAAAT
CAAACAGAAGACGGAGGACTACCACAAAGTGGTAGAATTGTTGTTGATTACATGGTGCAAAAATCTGGGAAAACAGGAACAATT
ACCTATCAAAGGGGTATTTTATTGCCTCAAAAGGTGTGGTGCGCAAGTGGCAGGAGCAAGGTAATAAAAGGATCCTTGCCTTTAA
TTGGAGAAGCAGATTGCCTCCACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACCTCCTGGTGGAGGATGGGAAG
GAATGATTGCAGGTTGGCACGGATACACATCCCATGGGGCACATGGAGTAGCGGTGGCAGCAGACCTTAAGAGCACTCAAGAGG
CCATAAACAAGATAACAAAAAATCTCAACTCTTTGAGTGAGCTGGAAGTAAAGAATCTTCAAAGACTAAGCGGTGCCATGGATGA
ACTCCACAACGAAATACTAGAACTAGATGAGAAAGTGGATGATCTCAGAGCTGATACAATAAGCTCACAAATAGAACTCGCAGTC
CTGCTTTCCAATGAAGGAATAATAAACAGTGAAGATGAACATCTCTTGGCGCTTGAAAGAAAGCTGAAGAAAATGCTGGGCCCCT
CTGCTGTAGAGATAGGGAATGGATGCTTTGAAACCAAACACAAGTGCAACCAGACCTGTCTCGACAGAATAGCTGCTGGTACCTT
TGATGCAGGAGAATTTTCTCTCCCCACCTTTGATTCACTGAATATTACTGCTGCATCTTTAAATGACGATGGATTGGATAATCATAC
TATACTGCTTTACTACTCAACTGCTGCCTCCAGTTTGGCTGTAACACTGATGATAGCTATCTTTGTTGTTTATATGGTCTCCAGAGAC
AATGTTTCTTGCTCCATCTGTCTATAA

Figure 12B (SEQ ID NO :44)

Amino acid sequence of PDISP/HA B Brisbane (PrL-).

MAKNVAIFGLLFSLLVLVPSQIFADRICTGITSSNSPHVVKTATQGEVNVTGVIPLTTTPTKSHFANLKGTETRGKLCPKCLNCTDLDVALG
RPKCTGKIPSARVSILHEVRPVTSGCFPIMHDRTKIRQLPNLLRGYEHIRLSTHNVINAENAPGGPYKIGTSGSCPNITNGNGFFATMAW
AVPKNDKNKTATNPLTIEVPYICTEGEDQITVWGFHSDNETQMAKLYGDSKPQKFTSSANGVTTHYVSQIGGFPNQTEDGGLPQSGRI
VVDYMVQKSGKTGTITYQRGILLPQKVWCASGRSKVIKGSLPLIGEADCLHEKYGGLNKSKPYYTGEHAKAIGNCPIWVKTPLKLANGTK
YRPPGGGWEGMIAGWHGYTSHGAHGVAVAADLKSTQEAINKITKNLNSLSELEVKNLQRLSGAMDELHNEILELDEKVDDLRADTISS
QIELAVLLSNEGIINSEDEHLLALERKLKKMLGPSAVEIGNGCFETKHKCNQTCLDRIAAGTFDAGEFSLPTFDSLNITAASLNDDGLDNHT
ILLYYSTAASSLAVTLMIAIFVVYMVSRDNVSCSICL*

Schematic representation of construct number 1039 (2X35S/CPMV HT)

Schematic representation of construct number 1829 (2X35S/CPMV HT+)

Figure 13: L- 2X35S/CPMV HT (construct no 1067) and HT+ (construct no 1875) for PDISP/HA B Brisbane (PrL-)+H1 California TMCT

Figure 13A (SEQ ID NO : 45)

Nucleotide sequence of PDISP/HA B Brisbane (PrL-)+H1 California TMCT.

ATGGCGAAAAACGTTGCGATTTTCGGCTTATTGTTTTCTCTTCTTGTGTTGGTTCCTTCTCAGATCTTCGCCGATCGAATCTGCACTG
GAATAACATCGTCAAACTCACCACATGTCGTCAAAACTGCTACTCAAGGGGAGGTCAATGTGACTGGTGTAATACCACTGACAAC
AACACCCACCAAATCTCATTTTGCAAATCTCAAAGGAACAGAAACCAGGGGGAAACTATGCCCAAAATGCCTCAACTGCACAGAT
CTGGACGTAGCCTTGGGCAGACCAAAATGCACGGGGAAAATACCCTCGGCAAGAGTTTCAATACTCCATGAAGTCAGACCTGTTA
CATCTGGGTGCTTTCCTATAATGCACGACAGAACAAAAATTAGACAGCTGCCTAACCTTCTCCGAGGATACGAACATATCAGGTTA
TCAACCCATAACGTTATCAATGCAGAAAATGCACCAGGAGGACCCTACAAAATTGGAACCTCAGGGTCTTGCCCTAACATTACCAA
TGGAAACGGATTTTTCGCAACAATGGCTTGGGCCGTCCCAAAAAACGACAAAAACAAAACAGCAACAAATCCATTAACAATAGAA
GTACCATACATTTGTACAGAAGGAGAAGACCAAATTACCGTTTGGGGGTTCCACTCTGACAACGAGACCCAAATGGCAAAGCTCT
ATGGGGACTCAAAGCCCCAGAAGTTCACCTCATCTGCCAACGGAGTGACCACACATTACGTTTCACAGATTGGTGGCTTCCCAAAT
CAAACAGAAGACGGAGGACTACCACAAAGTGGTAGAATTGTTGTTGATTACATGGTGCAAAAATCTGGGAAAACAGGAACAATT
ACCTATCAAAGGGGTATTTTATTGCCTCAAAAGGTGTGGTGCGCAAGTGGCAGGAGCAAGGTAATAAAAGGATCCTTGCCTTTAA
TTGGAGAAGCAGATTGCCTCCACGAAAAATACGGTGGATTAAACAAAAGCAAGCCTTACTACACAGGGGAACATGCAAAGGCCA
TAGGAAATTGCCCAATATGGGTGAAAACACCCTTGAAGCTGGCCAATGGAACCAAATATAGACCTCCTGGTGGAGGATGGGAAG
GAATGATTGCAGGTTGGCACGGATACACATCCCATGGGGCACATGGAGTAGCGGTGGCAGCAGACCTTAAGAGCACTCAAGAGG
CCATAAACAAGATAACAAAAAATCTCAACTCTTTGAGTGAGCTGGAAGTAAAGAATCTTCAAAGACTAAGCGGTGCCATGGATGA
ACTCCACAACGAAATACTAGAACTAGATGAGAAAGTGGATGATCTCAGAGCTGATACAATAAGCTCACAAATAGAACTCGCAGTC
CTGCTTTCCAATGAAGGAATAATAAACAGTGAAGATGAACATCTCTTGGCGCTTGAAAGAAAGCTGAAGAAAATGCTGGGCCCCT
CTGCTGTAGAGATAGGGAATGGATGCTTTGAAACCAAACACAAGTGCAACCAGACCTGTCTCGACAGAATAGCTGCTGGTACCTT
TGATGCAGGAGAATTTTCTCTCCCCACCTTTGATTCACTGAATATTACTGCTGCATCTTTAAATGACGATGGATTGGATAATTACCA
GATTTTGGCGATCTATTCAACTGTCGCCAGTTCATTGGTACTGGTAGTCTCCCTGGGGGCAATCAGTTTCTGGATGTGCTCTAATG
GGTCTCTACAGTGTAGAATATGTATTTAA

Figure 13B (SEQ ID NO : 46)

Amino acid sequence of PDISP/HA B Brisbane (PrL-)+H1 California TMCT.

MAKNVAIFGLLFSLLVLVPSQIFADRICTGITSSNSPHVVKTATQGEVNVTGVIPLTTTPTKSHFANLKGTETRGKLCPKCLNCTDLDVALG
RPKCTGKIPSARVSILHEVRPVTSGCFPIMHDRTKIRQLPNLLRGYEHIRLSTHNVINAENAPGGPYKIGTSGSCPNITNGNGFFATMAW
AVPKNDKNKTATNPLTIEVPYICTEGEDQITVWGFHSDNETQMAKLYGDSKPQKFTSSANGVTTHYVSQIGGFPNQTEDGGLPQSGRI
VVDYMVQKSGKTGTITYQRGILLPQKVWCASGRSKVIKGSLPLIGEADCLHEKYGGLNKSKPYYTGEHAKAIGNCPIWVKTPLKLANGTK
YRPPGGGWEGMIAGWHGYTSHGAHGVAVAADLKSTQEAINKITKNLNSLSELEVKNLQRLSGAMDELHNEILELDEKVDDLRADTISS
QIELAVLLSNEGIINSEDEHLLALERKLKKMLGPSAVEIGNGCFETKHKCNQTCLDRIAAGTFDAGEFSLPTFDSLNITAASLNDDGLDNYQ
ILAIYSTVASSLVLVVSLGAISFWMCSNGSLQCRICI*

Schematic representation of construct number 1067 (2X35S/CPMV HT)

Schematic representation of construct number 1875 (2X35S/CPMV HT+)

Figure 14: M- 2X35S/CPMV HT (construct no 2072) and HT+ (construct no 2052) for PDISP/HA B Massachussetts (PrL-)

Figure 14A (SEQ ID NO : 47)

Nucleotide sequence of PDISP/HA B Massachussetts (PrL-).

ATGGCGAAAAACGTTGCGATTTTCGGCTTATTGTTTTCTCTTCTTGTGTTGGTTCCTTCTCAGATCTTCGCCGATCGAATCTGCACTG
GGATAACATCTTCAAACTCACCTCATGTGGTCAAAACAGCTACTCAAGGGGAGGTCAATGTGACTGGTGTGATACCACTAACAAC
AACACCAACAAAATCTTATTTTGCAAATCTCAAAGGAACAAAGACCAGAGGGAAACTATGCCCAGACTGTCTCAACTGTACAGATC
TGGATGTGGCCCTGGGCAGGCCAATGTGTGTGGGAACTACACCTTCTGCGAAAGCTTCAATACTTCACGAAGTCAGACCTGTTAC
ATCCGGGTGCTTCCCTATAATGCACGACAGAACAAAAATCAGGCAACTAGCCAATCTTCTCAGAGGATATGAAAATATCAGGTTAT
CAACCCAAAACGTTATCGATGCAGAAAAGGCACCAGGAGGACCCTACAGACTTGGAACCTCAGGATCTTGCCCTAACGCTACCAG
TAAAAGCGGATTTTTCGCAACAATGGCTTGGGCTGTCCCAAAGGACAACAACAAAAATGCAACGAACCCATTAACAGTAGAAGTA
CCATACATTTGTGCAGAAGGGGAAGACCAAATTACTGTTTGGGGGTTCCATTCAGATAACAAAACCCAAATGAAGAACCTCTATG
GAGACTCAAATCCTCAAAAGTTCACCTCATCTGCTAATGGAGTAACCACACATTATGTTTCTCAGATTGGCGGCTTCCCAGATCAAA
CAGAAGACGGAGGACTACCACAAAGCGGCAGAATTGTCGTTGATTACATGATGCAAAAACCTGGGAAAACAGGAACAATTGTCT
ATCAAAGAGGTGTTTTGTTGCCTCAAAAGGTGTGGTGCGCGAGTGGCAGGAGCAAAGTAATAAAAGGGTCCTTGCCTTTAATTGG
TGAAGCAGATTGCCTTCATGAAAAATACGGTGGATTAAACAAAAGCAAGCCTTACTACACAGGAGAACATGCAAAAGCCATAGG
AAATTGCCCAATATGGGTGAAAACACCTTTGAAGCTTGCCAATGGAACCAAATATAGACCTCCTGGTGGAGGATGGGAAGGAAT
GATTGCAGGTTGGCACGGATACACATCTCACGGAGCACATGGAGTGGCAGTTGCTGCAGACCTTAAGAGCACACAAGAAGCTAT
AAACAAGATAACAAAAAATCTCAACTCTTTGAGTGAGCTAGAAGTAAAGAATCTTCAAAGGCTAAGTGGTGCCATGGATGAACTC
CACAACGAAATACTCGAGCTGGATGAGAAAGTGGATGACCTCAGAGCTGACACTATAAGTTCACAAATAGAACTTGCAGTCTTGC
TTTCCAACGAAGGAATAATAAACAGTGAAGACGAGCATCTATTGGCACTTGAGAGAAAACTAAAGAAAATGCTGGGTCCCTCTGC
TGTAGACATAGGAAATGGATGCTTCGAAACCAAACACAAATGCAACCAGACCTGCTTAGACAGGATAGCTGCTGGCACCTTTAAT
GCAGGAGAGTTTTCTCTCCCCACTTTTGATTCATTGAACATTACTGCTGCATCTTTAAATGATGATGGATTGGATAACCATACTATA
CTGCTCTATTACTCAACTGCTGCTTCTAGTTTGGCTGTAACATTGATGCTAGCTATTTTTATTGTTTATATGGTCTCCAGAGACAACG
TTTCATGCTCCATCTGTCTATAA

Figure 14B (SEQ ID NO :48)

Amino acid sequence of PDISP/HA B Massachussetts (PrL-).

MAKNVAIFGLLFSLLVLVPSQIFADRICTGITSSNSPHVVKTATQGEVNVTGVIPLTTTPTKSYFANLKGTKTRGKLCPDCLNCTDLDVALG
RPMCVGTTPSAKASILHEVRPVTSGCFPIMHDRTKIRQLANLLRGYENIRLSTQNVIDAEKAPGGPYRLGTSGSCPNATSKSGFFATMA
WAVPKDNNKNATNPLTVEVPYICAEGEDQITVWGFHSDNKTQMKNLYGDSNPQKFTSSANGVTTHYVSQIGGFPDQTEDGGLPQSG
RIVVDYMMQKPGKTGTIVYQRGVLLPQKVWCASGRSKVIKGSLPLIGEADCLHEKYGGLNKSKPYYTGEHAKAIGNCPIWVKTPLKLAN
GTKYRPPGGGWEGMIAGWHGYTSHGAHGVAVAADLKSTQEAINKITKNLNSLSELEVKNLQRLSGAMDELHNEILELDEKVDDLRAD
TISSQIELAVLLSNEGIINSEDEHLLALERKLKKMLGPSAVDIGNGCFETKHKCNQTCLDRIAAGTFNAGEFSLPTFDSLNITAASLNDDGLD
NHTILLYYSTAASSLAVTLMLAIFIVYMVSRDNVSCSICL*

Figure 14C Schematic representation of construct number 2072 (2X35S/CPMV HT)
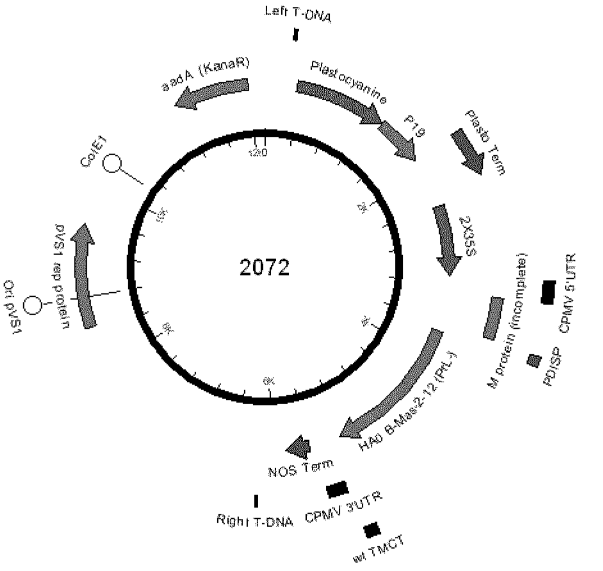
Figure 14D Schematic representation of construct number 2052 (2X35S/CPMV HT+)
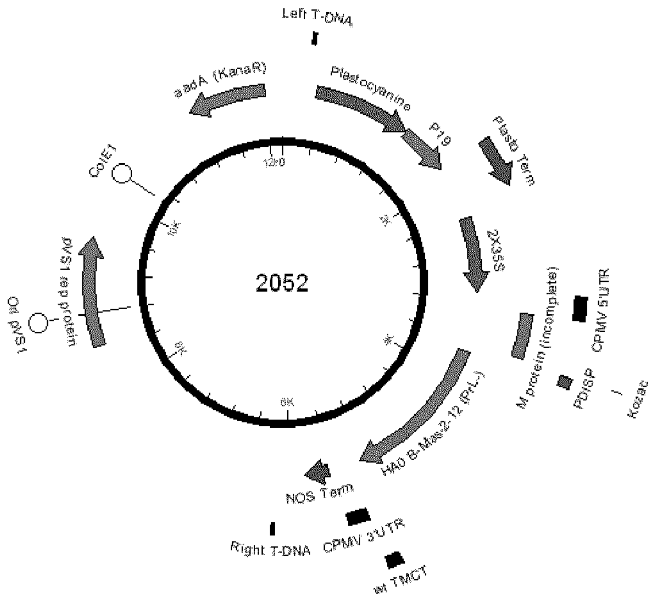

Figure 15: N- 2X35S/CPMV HT (construct no 2074) and HT+ (construct no 2062) for PDISP/HA B Massachussetts (PrL-)+H1 California TMCT

Figure 15A (SEQ ID NO : 49)

Nucleotide sequence of PDISP/HA B Massachussetts (PrL-)+H1 California TMCT.

ATGGCGAAAAACGTTGCGATTTTCGGCTTATTGTTTTCTCTTCTTGTGTTGGTTCCTTCTCAGATCTTCGCCGATCGAATCTGCACTG
GGATAACATCTTCAAACTCACCTCATGTGGTCAAAACAGCTACTCAAGGGGAGGTCAATGTGACTGGTGTGATACCACTAACAAC
AACACCAACAAAATCTTATTTTGCAAATCTCAAAGGAACAAAGACCAGAGGGAAACTATGCCCAGACTGTCTCAACTGTACAGATC
TGGATGTGGCCCTGGGCAGGCCAATGTGTGTGGGAACTACACCTTCTGCGAAAGCTTCAATACTTCACGAAGTCAGACCTGTTAC
ATCCGGGTGCTTCCCTATAATGCACGACAGAACAAAAATCAGGCAACTAGCCAATCTTCTCAGAGGATATGAAAATATCAGGTTAT
CAACCCAAAACGTTATCGATGCAGAAAAGGCACCAGGAGGACCCTACAGACTTGGAACCTCAGGATCTTGCCCTAACGCTACCAG
TAAAAGCGGATTTTTCGCAACAATGGCTTGGGCTGTCCCAAAGGACAACAACAAAAATGCAACGAACCCATTAACAGTAGAAGTA
CCATACATTTGTGCAGAAGGGGAAGACCAAATTACTGTTTGGGGGTTCCATTCAGATAACAAAACCCAAATGAAGAACCTCTATG
GAGACTCAAATCCTCAAAAGTTCACCTCATCTGCTAATGGAGTAACCACACATTATGTTTCTCAGATTGGCGGCTTCCCAGATCAAA
CAGAAGACGGAGGACTACCACAAAGCGGCAGAATTGTCGTTGATTACATGATGCAAAAACCTGGGAAAACAGGAACAATTGTCT
ATCAAAGAGGTGTTTTGTTGCCTCAAAAGGTGTGGTGCGCGAGTGGCAGGAGCAAAGTAATAAAAGGGTCCTTGCCTTTAATTGG
TGAAGCAGATTGCCTTCATGAAAAATACGGTGGATTAAACAAAAGCAAGCCTTACTACACAGGAGAACATGCAAAAGCCATAGG
AAATTGCCCAATATGGGTGAAAACACCTTTGAAGCTTGCCAATGGAACCAAATATAGACCTCCTGGTGGAGGATGGGAAGGAAT
GATTGCAGGTTGGCACGGATACACATCTCACGGAGCACATGGAGTGGCAGTTGCTGCAGACCTTAAGAGCACACAAGAAGCTAT
AAACAAGATAACAAAAAATCTCAACTCTTTGAGTGAGCTAGAAGTAAAGAATCTTCAAAGGCTAAGTGGTGCCATGGATGAACTC
CACAACGAAATACTCGAGCTGGATGAGAAAGTGGATGACCTCAGAGCTGACACTATAAGTTCACAAATAGAACTTGCAGTCTTGC
TTTCCAACGAAGGAATAATAAACAGTGAAGACGAGCATCTATTGGCACTTGAGAGAAAACTAAAGAAAATGCTGGGTCCCTCTGC
TGTAGACATAGGAAATGGATGCTTCGAAACCAAACACAAATGCAACCAGACCTGCTTAGACAGGATAGCTGCTGGCACCTTTAAT
GCAGGAGAGTTTTCTCTCCCCACTTTTGATTCATTGAACATTACTGCTGCATCTTTAAATGATGATGGATTGGATAACTACCAGATT
TTGGCGATCTATTCAACTGTCGCCAGTTCATTGGTACTGGTAGTCTCCCTGGGGGCAATCAGTTTCTGGATGTGCTCTAATGGGTCT
CTACAGTGTAGAATATGTATTTAA

Figure 15B (SEQ ID NO :50)

Amino acid sequence of PDISP/HA B Massachussetts (PrL-)+H1 California TMCT.

MAKNVAIFGLLFSLLVLVPSQIFADRICTGITSSNSPHVVKTATQGEVNVTGVIPLTTTPTKSYFANLKGTKTRGKLCPDCLNCTDLDVALG
RPMCVGTTPSAKASILHEVRPVTSGCFPIMHDRTKIRQLANLLRGYENIRLSTQNVIDAEKAPGGPYRLGTSGSCPNATSKSGFFATMA
WAVPKDNNKNATNPLTVEVPYICAEGEDQITVWGFHSDNKTQMKNLYGDSNPQKFTSSANGVTTHYVSQIGGFPDQTEDGGLPQSG
RIVVDYMMQKPGKTGTIVYQRGVLLPQKVWCASGRSKVIKGSLPLIGEADCLHEKYGGLNKSKPYYTGEHAKAIGNCPIWVKTPLKLAN
GTKYRPPGGGWEGMIAGWHGYTSHGAHGVAVAADLKSTQEAINKITKNLNSLSELEVKNLQRLSGAMDELHNEILELDEKVDDLRAD
TISSQIELAVLLSNEGIINSEDEHLLALERKLKKMLGPSAVDIGNGCFETKHKCNQTCLDRIAAGTFNAGEFSLPTFDSLNITAASLNDDGLD
NYQILAIYSTVASSLVLVVSLGAISFWMCSNGSLQCRICI*

Figure 15C Schematic representation of construct number 2074 (2X35S/CPMV HT)
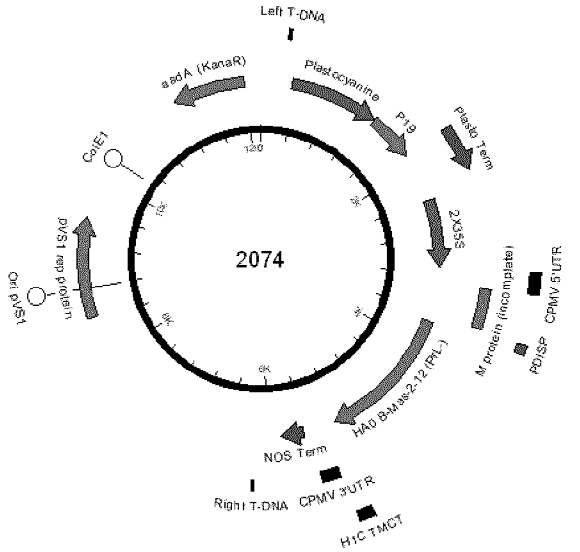
Figure 15D Schematic representation of construct number 2062 (2X35S/CPMV HT+)
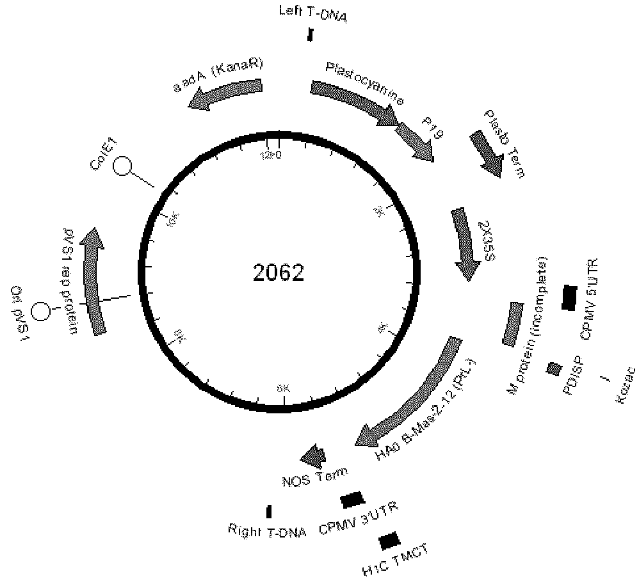

Figure 16: O- 2X35S/CPMV HT (construct no 1445), HT+ (construct no 1839) for HA B Wisconsin (PrL-)

Figure 16A (SEQ ID NO :51)

Nucleotide sequence of HA B Wisconsin (PrL-).

ATGAAGGCAATAATTGTACTACTCATGGTAGTAACATCCAATGCAGATCGAATCTGCACTGGGATAACATCTTCAAACTCACCTCA
TGTGGTCAAAACAGCTACTCAAGGGGAGGTCAATGTGACTGGCGTGATACCACTGACAACAACACCAACAAAATCTTATTTTGCA
AATCTCAAAGGAACAAGGACCAGAGGGAAACTATGCCCGGACTGTCTCAACTGTACAGATCTGGATGTGGCCTTGGGCAGGCCA
ATGTGTGTGGGGACCACACCTTCTGCTAAAGCTTCAATACTCCACGAGGTCAGACCTGTTACATCCGGGTGCTTTCCTATAATGCA
CGACAGAACAAAAATCAGGCAACTACCCAATCTTCTCAGAGGATATGAAAATATCAGGTTATCAACCCAAAACGTTATCGATGCA
GAAAAAGCACCAGGAGGACCCTACAGACTTGGAACCTCAGGATCTTGCCCTAACGCTACCAGTAAAATCGGATTTTTTGCAACAA
TGGCTTGGGCTGTCCCAAAGGACAACTACAAAAATGCAACGAACCCACTAACAGTAGAAGTACCATACATTTGTACAGAAGGGGA
AGACCAAATTACTGTTTGGGGGTTCCATTCAGATAACAAAACCCAAATGAAGAGCCTCTATGGAGACTCAAATCCTCAAAAGTTCA
CCTCATCTGCTAATGGAGTAACCACACATTATGTTTCTCAGATTGGCGACTTCCCAGATCAAACAGAAGACGGAGGACTACCACAA
AGCGGCAGAATTGTTGTTGATTACATGATGCAAAAACCTGGGAAAACAGGAACAATTGTCTATCAAAGAGGTGTTTTGTTGCCTC
AAAAGGTGTGGTGCGCGAGTGGCAGGAGCAAAGTAATAAAAGGGTCATTGCCTTTAATTGGTGAAGCAGATTGCCTTCATGAAA
AATACGGTGGATTAAACAAAAGCAAGCCTTACTACACAGGAGAACATGCAAAAGCCATAGGAAATTGCCCAATATGGGTAAAAA
CACCTTTGAAGCTTGCCAATGGAACCAAATATAGACCTCCTGGTGGAGGATGGGAAGGAATGATTGCAGGTTGGCACGGATACA
CATCTCACGGAGCACATGGAGTGGCAGTGGCGGCAGACCTTAAGAGTACACAAGAAGCTATAAATAAGATAACAAAAAATCTCA
ATTCTTTGAGTGAGCTAGAAGTAAAGAACCTTCAAAGACTAAGTGGTGCCATGGATGAACTCCACAACGAAATACTCGAGCTGGA
TGAGAAAGTGGATGATCTCAGAGCTGACACTATAAGCTCACAAATAGAACTTGCAGTCTTGCTTTCCAACGAAGGAATAATAAAC
AGTGAAGACGAGCATCTATTGGCACTTGAGAGAAAACTAAAGAAAATGCTGGGTCCCTCTGCTGTAGACATAGGAAACGGATGC
TTCGAAACCAAACACAAATGCAACCAGACCTGCTTAGACAGGATAGCTGCTGGCACCTTTAATGCAGGAGAATTTTCTCTCCCCAC
TTTTGATTCATTGAACATTACTGCTGCATCTTTAAATGATGATGGATTGGATAACCATACTATACTGCTCTATTACTCAACTGCTGCT
TCTAGTTTGGCTGTAACATTAATGCTAGCTATTTTTATTGTTTATATGGTCTCCAGAGACAACGTTTCATGCTCCATCTGTCTATAA

Figure 16B (SEQ ID NO :52)

Amino acid sequence of HA B Wisconsin (PrL-).

MKAIIVLLMVVTSNADRICTGITSSNSPHVVKTATQGEVNVTGVIPLTTTPTKSYFANLKGTRTRGKLCPDCLNCTDLDVALGRPMCVGT
TPSAKASILHEVRPVTSGCFPIMHDRTKIRQLPNLLRGYENIRLSTQNVIDAEKAPGGPYRLGTSGSCPNATSKIGFFATMAWAVPKDNY
KNATNPLTVEVPYICTEGEDQITVWGFHSDNKTQMKSLYGDSNPQKFTSSANGVTTHYVSQIGDFPDQTEDGGLPQSGRIVVDYMM
QKPGKTGTIVYQRGVLLPQKVWCASGRSKVIKGSLPLIGEADCLHEKYGGLNKSKPYYTGEHAKAIGNCPIWVKTPLKLANGTKYRPPGG
GWEGMIAGWHGYTSHGAHGVAVAADLKSTQEAINKITKNLNSLSELEVKNLQRLSGAMDELHNEILELDEKVDDLRADTISSQIELAVL
LSNEGIINSEDEHLLALERKLKKMLGPSAVDIGNGCFETKHKCNQTCLDRIAAGTFNAGEFSLPTFDSLNITAASLNDDGLDNHTILLYYST
AASSLAVTLMLAIFIVYMVSRDNVSCSICL*

Schematic representation of construct number 1445 (2X35S/CPMV HT)

Schematic representation of construct number 1839 (2X35S/CPMV HT+)

Figure 17: P- 2X35S/CPMV HT (construct no 1454) and HT+ (construct no 1860) for HA B Wisconsin (PrL-)+H1 California TMCT

Figure 17A (SEQ ID NO :53)

Nucleotide sequence of HA B Wisconsin (PrL-)+H1 California TMCT

ATGAAGGCAATAATTGTACTACTCATGGTAGTAACATCCAATGCAGATCGAATCTGCACTGGGATAACATCTTCAAACTCACCTCA
TGTGGTCAAAACAGCTACTCAAGGGGAGGTCAATGTGACTGGCGTGATACCACTGACAACAACACCAACAAAATCTTATTTTGCA
AATCTCAAAGGAACAAGGACCAGAGGGAAACTATGCCCGGACTGTCTCAACTGTACAGATCTGGATGTGGCCTTGGGCAGGCCA
ATGTGTGTGGGGACCACACCTTCTGCTAAAGCTTCAATACTCCACGAGGTCAGACCTGTTACATCCGGGTGCTTTCCTATAATGCA
CGACAGAACAAAAATCAGGCAACTACCCAATCTTCTCAGAGGATATGAAAATATCAGGTTATCAACCCAAAACGTTATCGATGCA
GAAAAAGCACCAGGAGGACCCTACAGACTTGGAACCTCAGGATCTTGCCCTAACGCTACCAGTAAAATCGGATTTTTTGCAACAA
TGGCTTGGGCTGTCCCAAAGGACAACTACAAAAATGCAACGAACCCACTAACAGTAGAAGTACCATACATTTGTACAGAAGGGGA
AGACCAAATTACTGTTTGGGGGTTCCATTCAGATAACAAAACCCAAATGAAGAGCCTCTATGGAGACTCAAATCCTCAAAAGTTCA
CCTCATCTGCTAATGGAGTAACCACACATTATGTTTCTCAGATTGGCGACTTCCCAGATCAAACAGAAGACGGAGGACTACCACAA
AGCGGCAGAATTGTTGTTGATTACATGATGCAAAAACCTGGGAAAACAGGAACAATTGTCTATCAAAGAGGTGTTTTGTTGCCTC
AAAAGGTGTGGTGCGCGAGTGGCAGGAGCAAAGTAATAAAAGGGTCATTGCCTTTAATTGGTGAAGCAGATTGCCTTCATGAAA
AATACGGTGGATTAAACAAAAGCAAGCCTTACTACACAGGAGAACATGCAAAAGCCATAGGAAATTGCCCAATATGGGTAAAAA
CACCTTTGAAGCTTGCCAATGGAACCAAATATAGACCTCCTGGTGGAGGATGGGAAGGAATGATTGCAGGTTGGCACGGATACA
CATCTCACGGAGCACATGGAGTGGCAGTGGCGGCAGACCTTAAGAGTACACAAGAAGCTATAAATAAGATAACAAAAAATCTCA
ATTCTTTGAGTGAGCTAGAAGTAAAGAACCTTCAAAGACTAAGTGGTGCCATGGATGAACTCCACAACGAAATACTCGAGCTGGA
TGAGAAAGTGGATGATCTCAGAGCTGACACTATAAGCTCACAAATAGAACTTGCAGTCTTGCTTTCCAACGAAGGAATAATAAAC
AGTGAAGACGAGCATCTATTGGCACTTGAGAGAAAACTAAAGAAAATGCTGGGTCCCTCTGCTGTAGACATAGGAAACGGATGC
TTCGAAACCAAACACAAATGCAACCAGACCTGCTTAGACAGGATAGCTGCTGGCACCTTTAATGCAGGAGAATTTTCTCTCCCCAC
TTTTGATTCATTGAACATTACTGCTGCATCTTTAAATGATGATGGATTGGATAACTACCAGATTTTGGCGATCTATTCAACTGTCGC
CAGTTCATTGGTACTGGTAGTCTCCCTGGGGGCAATCAGTTTCTGGATGTGCTCTAATGGGTCTCTACAGTGTAGAATATGTATTT
AA

Figure 17B (SEQ ID NO : 54)

Amino acid sequence of HA B Wisconsin (PrL-)+H1 California TMC.

MKAIIVLLMVVTSNADRICTGITSSNSPHVVKTATQGEVNVTGVIPLTTTPTKSYFANLKGTRTRGKLCPDCLNCTDLDVALGRPMCVGT
TPSAKASILHEVRPVTSGCFPIMHDRTKIRQLPNLLRGYENIRLSTQNVIDAEKAPGGPYRLGTSGSCPNATSKIGFFATMAWAVPKDNY
KNATNPLTVEVPYICTEGEDQITVWGFHSDNKTQMKSLYGDSNPQKFTSSANGVTTHYVSQIGDFPDQTEDGGLPQSGRIVVDYMM
QKPGKTGTIVYQRGVLLPQKVWCASGRSKVIKGSLPLIGEADCLHEKYGGLNKSKPYYTGEHAKAIGNCPIWVKTPLKLANGTKYRPPGG
GWEGMIAGWHGYTSHGAHGVAVAADLKSTQEAINKITKNLNSLSELEVKNLQRLSGAMDELHNEILELDEKVDDLRADTISSQIELAVL
LSNEGIINSEDEHLLALERKLKKMLGPSAVDIGNGCFETKHKCNQTCLDRIAAGTFNAGEFSLPTFDSLNITAASLNDDGLDNYQILAIYST
VASSLVLVVSLGAISFWMCSNGSLQCRICI*

Schematic representation of construct number 1454 (2X35S/CPMV HT)

Schematic representation of construct number 1860 (2X35S/CPMV HT+)

MODIFIED CPMV ENHANCER ELEMENTS

CROSS-REFERENCE TO RELATED APPLICATIONS

This application is a national phase application of PCT/CA2015/050240, filed Mar. 27, 2015. PCT/CA2015/050240 is a Continuation-In-Part of and claims priority from PCT Application No. PCT/CA2014/050326, filed Mar. 28, 2014. PCT/CA2015/050240 also claims priority from U.S. Provisional Application No. 61/971,274, filed Mar. 27, 2014. The content of each of these applications is hereby incorporated by reference.

REFERENCE TO SEQUENCE LISTING

The content of the following text file, which provides a computer-readable form (CRF) of the Sequence Listing for this application, is incorporated herein by reference in its entirety:
file name: PCTCA2015050240_SEQUENCE.txt; created: Sep. 26, 2016; size: 111 KB.

FIELD OF INVENTION

The present invention relates to the expression of proteins of interest in plants. The present invention also provides methods and compositions for the production of proteins of interest in plants.

BACKGROUND OF THE INVENTION

Plants offer great potential as production systems for recombinant proteins. One approach to producing foreign proteins in plants is to generate stable transgenic plant lines. However this is a time consuming and labor intensive process. An alternative to transgenic plants is the use of plant virus-based expression vectors. Plant virus-based vectors allow for the rapid, high level, transient expression of proteins in plants.

One method to achieve high level transient expression of foreign proteins in plants involves the use of vectors based on RNA plant viruses, including comoviruses, such as *Cowpea mosaic* virus (CPMV; see, for example, WO2007/135480; WO2009/087391; US 2010/0287670, Sainsbury F. et al., 2008, *Plant Physiology;* 148: 121-1218; Sainsbury F. et al., 2008, *Plant Biotechnology Journal;* 6: 82-92; Sainsbury F. et al., 2009, *Plant Biotechnology Journal;* 7: 682-693; Sainsbury F. et al. 2009, *Methods in Molecular Biology, Recombinant Proteins From Plants*, vol. 483: 25-39).

Comoviruses are RNA viruses with a bipartite genome. The segments of the comoviral RNA genome are referred to as RNA-1 and RNA-2. RNA-1 encodes the VPg, replicase and protease proteins. The replicase is required by the virus for replication of the viral genome. The RNA-2 of the comovirus cowpea mosaic virus (CPMV) produces a polyprotein of 105 kDa or 95 kDa processed into 4 functional peptides.

The 5' region of CPMV RNA-2 comprises start codons (AUGs) at positions 115, 161, 512 and 524. The start codons at positions 161 and 512 are in the same triplet reading frame. Initiation at the start codon at position 161 results in the synthesis of the 105K polyprotein while initiation at the start codon at position 512 directs the synthesis of the 95K polyprotein. Initiation of translation at the start codon at position 512 in CPMV is more efficient than initiation at position 161, resulting in the production of more 95K polyprotein than 105K polyprotein. The start codon at position 115 is not essential for virus replication (Wellink et al., 1993 Biochimie. 75(8):741-7).

Maintenance of the frame between the initiation sites at positions 161 and 512 in CPMV RNA-2 is required for efficient replication of RNA-2 by the RNA-1-encoded replicase (Holness et al., 1989; Virology 172, 311-320; van Bokhoven et al. 1993, Virology 195, 377-386; Rohll et al., 1993 Virology 193, 672-679; Wellink et al., 1993, Biochimie. 75(8):741-7). This requirement impacts the length of sequences which can be inserted upstream of the 512 start codon in replicative forms of CPMV RNA-2 expression vectors. Furthermore, the use of polylinkers should be used with caution as they may shift the open reading frame (ORF) between these initiation sites.

CPMV has served as the basis for the development of vector systems suitable for the production of heterologous polypeptides in plants (Liu et al., 2005 Vaccine 23, 1788-1792; Sainsbury et al., 2007 Virus Expression Vectors (Hefferon, K. ed), pp. 339-555). These systems are based on the modification of RNA-2 but differ in whether full-length or deleted versions are used. Replication of the modified RNA-2 is achieved by co-inoculation with RNA-1. Foreign proteins are fused to the C-terminus of the RNA-2-derived polyproteins. Release of the N-terminal polypeptide is mediated by the action of the 2A catalytic peptide sequence from foot-and-mouth-disease virus (Gopinath et al., 2000, Virology 267: 159-173). The resulting RNA-2 molecules are capable of spreading both within and between plants. This strategy has been used to express a number of recombinant proteins, such as the Hepatitis B core antigen (HBcAg) and Small Immune Proteins (SIPs), in cowpea plants (Mechtcheriakova et al. J. Virol. Methods 131, 10-15; 2006; Monger et al., 2006, Plant Biotechnol. J. 4, 623-631; Alamillo et al., 2006, Biotechnol. J. 1, 1103-1111). Though successful, the use of a full-length viral vector limits the size of inserted sequences, and movement between plants raises concerns about biocontainment of the virus.

To address the issue of biocontainment and insert size, Canizares et al. (2006 Plant Biotechnol, J 4:183-193) replaced the majority of the coding region of RNA-2 with a sequence of interest to produce a disabled version of CPMV RNA-2 (deIRNA-2). The sequence to be expressed was fused to the AUG at position 512 of RNA-2, immediately upstream of the 3' untranslated region (UTR) to create a molecule that mimics RNA-2. Such constructs were capable of replication when introduced into plants in the presence of RNA-1 and a suppressor of silencing, and directed the synthesis of substantial levels of heterologous proteins (Sainsbury et al., 2008 Plant Biotechnol J 6:82-92).

Mutation of the start codon at position 161 in a CPMV RNA-2 vector (U162C; HT) increases the levels of expression of a protein encoded by a sequence inserted after the start codon at position 512. This permits the production of high levels of foreign proteins without the need for viral replication and was termed the CPMV-HT system (WO2009/087391; Sainsbury and Lomonossoff, 2008, Plant Physiol. 148, 1212-1218). In pEAQ expression plasmids (Sainsbury et al., 2009, Plant Biotechnology Journal, 7, pp 682-693; US 2010/0287670), the sequence to be expressed is positioned between the 5'UTR and the 3' UTR. The 5'UTR in the pEAQ series carries the U162C (HT) mutation.

SUMMARY OF THE INVENTION

The present invention relates to the expression of proteins of interest in plants. The present invention also provides methods and compositions for the production of proteins of interest in plants.

As described herein, there is provided an expression enhancer comprising in series, a CPMV 5'UTR nucleotide sequence comprising nucleotides 1-160 of SEQ ID NO:1, or comprising a nucleotide sequence comprising from about 80% to 100% sequence similarity with SEQ ID NO:1, and a stuffer fragment, the stuffer fragment comprising a nucleotide sequence encoding an incomplete M protein, one or more kozak sequence active in a plant, or both. The stuffer fragment may comprise a length from 10 to about 500 nucleotides, or any length therebetween. The incomplete M protein of the stuffer fragment may comprise a length from about 10 to about 351 nucleotides, or any length therebetween. The stuffer fragment may further comprise a multiple cloning site. The multiple cloning site comprises a length from about 0 to about 100 nucleotides, or any length therebetween.

Also provided is the expression enhancer as described above, wherein the kozak sequence is selected from the group of sequences as shown in SEQ ID NO's: 5-17.

Also provided is a plant expression system comprising a nucleic acid sequence comprising a regulatory region, operatively linked with an expression enhancer comprising in series, a CPMV 5'UTR nucleotide sequence comprising nucleotides 1-160 of SEQ ID NO:1, or comprising a nucleotide sequence comprising from about 80% to 100% sequence similarity with SEQ ID NO:1, and a stuffer fragment, the stuffer fragment comprising a nucleotide sequence encoding an incomplete M protein and one or more plant kozak sequence, the expression enhancer operatively linked with a nucleotide sequence of interest. The plant expression system may further comprising a comovirus 3' UTR. The plant expression system may further comprise a second nucleic acid sequence encoding a suppressor of silencing, for example HcPro or p19.

The nucleotide sequence of interest of the plant expression system as defined above may encodes viral protein or an antibody. For example, the viral protein may be selected from the group of H1, H2, H3, H4, H5, H6, H7, H8, H9, H10, H11, H12, H13, H14, H15, H16, influenza type B hemagglutinin. The nucleotide sequence encoding the viral protein or the antibody may comprise a native signal peptide sequence, or a non-native signal peptide, for example the non-native signal peptide may be obtained from Protein disulfide isomerase (PDI).

As described herein there is provided a method of producing a protein of interest in a plant or in a portion of a plant comprising, introducing into the plant or in the portion of a plant the plant expression system defined above, and incubating the plant or the portion of a plant under conditions that permit expression of the nucleotide sequence encoding the protein of interest.

The present invention also provides a plant or portion of a plant transiently transfected or stably transformed with the plant expression system as described above.

Plant-based expression systems preferably have a number of properties such as, for example, containing convenient cloning sites for genes of interest, may easily infect plants in a cost-effective manner, may cause efficient local or systemic infection of inoculated plants. In addition, the infection should provide a good yield of useful protein material.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1A shows a general schematic of an example of an enhancer sequence of the prior art (CPMV HT) and as described herein (CPMV HT+) fused to a nucleotide sequence of interest. Not all of the elements shown in this figure may be required within the enhancer sequence. Additional elements may be included at the 3' end of the nucleotide sequence of interest (not shown) including a sequence encoding a comovirus 3' untranslated region (UTR), a plastocyanin 3' UTR, or a combination of the comovirus 3' UTR and the plastocyanin 3' UTR. FIG. 1B shows constructs comprising enhancer sequences, as described in the prior art (CPMV HT) and as described in the present invention (CPMV HT+), operatively linked to plant regulatory region (in these non-limiting examples 2X35S) at their 5' ends, and at their 3' ends, a stuffer fragment, a nucleotide sequence of interest, "GOI" comprising an ATG initiation site. In these examples, the stuffer fragment for CPMV HT comprises an incomplete M protein and a multiple cloning site, and in the example for CPMV HT+, the stuffer fragment comprises an incomplete M protein, a multiple cloning site and a plant kozak sequence. The CPMV HT nucleotide sequence in FIG. 1B (upper), for example, corresponds to bases 734-1267 of SEQ ID NO:22 (expression cassette 1391), with internal portions omitted for brevity. The CPMV HT+ nucleotide sequence in FIG. 1B (lower), for example, corresponds to bases 2877-3425 of SEQ ID NO:25 (construct 2181), with internal portions omitted for brevity.

FIG. 5 shows the sequence components used to prepare construct number 1391(A-2X35S CPMV-HT PDISP H3Victoria NOS; see example 1). Construct number 1391 incorporates a prior art CPMV-HT sequence (CPMV 5'UTR with mutated start codon at position 161 fused to a sequence encoding an incomplete M protein and does not comprise a heterologous kozak sequence between the 5'UTR and the nucleotide sequence of interest (PDISP/H3 Victoria)). PDISP: protein disulfide isomerase signal peptide. NOS: nopaline synthase terminator. FIG. 5A shows primer sequence IF-PDI.S1=3c (SEQ ID NO:18). FIG. 5B shows primer sequence IF-H3V36111.s1-4r (SEQ ID NO:19). FIG. 5C shows the sequence of PDISP/H3 Victoria (SEQ ID NO:20). FIG. 5E shows construct 1191; from left to right t-DNA borders (underlined), 2X35S CPMV-HT NOS, with Plastocyanine-P19-Plastocyanine silencing inhibitor expression cassette (SEQ ID NO:21). FIG. 5F shows expression cassette number 1391 from 2X35S promoter to NOS terminator. The PDISP/H3 Victoria nucleotide sequence is underlined; CPMV 5'UTR in bold; incomplete M-protein in italics (SEQ ID NO:22). FIG. 5G shows the amino acid sequence of PDISP/H3 Victoria (SEQ ID NO:23). FIG. 5H shows a schematic representation of construct number 1391 (a reference construct).

FIG. 6 shows the sequence components used to prepare construct number 1819 (2X35S CPMV-HT+ PDISP H3Victoria NOS; see example 1). Construct number 1819 incorporates a CPMV-HT+ sequence (CPMV 5'UTR with mutated start codon at position 161 fused to a stuffer fragment encoding an incomplete M protein, a multiple cloning site, and comprises a plant kozak sequence between the multiple cloning site and the nucleotide sequence of interest (PDISP/H3 Victoria)). PDISP: protein disulfide isomerase signal peptide. NOS: nopaline synthase terminator. FIG. 6A shows primer sequence IF(SacII)-Kozac_PDI.c (SEQ ID NO:24). FIG. 6B shows a schematic representation of construct 2181. FIG. 6C shows the sequence for construct 2181 (from left to right t-DNA borders, underlined; 2X35S/CPMV-HT+/NOS with Plastocyanine-P19-Plastocyanine silencing inhibitor expression cassette; SEQ ID NO:25). FIG. 6D shows expression cassette number 1819 from 2X35S promoter to NOS terminator. The PDISP/H3 Victoria nucleotide sequence is underlined (SEQ ID NO:26).

FIG. 7 shows sequences comprising variations in a plant kozak sequence used to prepare a selection of "CPMV HT+" based constructs (constructs number 1952 to 1959). Variation of sequence between SacII restriction site and ATG of PDISP/H3 Victoria in 2X35S/CPMV HT+/NOS expression system, comprising variations in a plant kozak sequence are shown (the sequences are shown as variations from the corresponding sequence from construct 1819; see Example 2). The variant plant kozak sequence are underlined. PDISP: protein disulfide isomerase signal peptide. FIG. 7A shows the nucleotide sequence of IF-HT1*-PDI.c (SEQ ID NO: 27; used to prepare construct number 1952). FIG. 7B shows the nucleotide sequence of IF-HT2*-PDI.c (SEQ ID NO:28; used to prepare construct number 1953). FIG. 7C shows the nucleotide sequence of IF-HT3*-PDI.c (SEQ ID NO:29; used to prepare construct number 1954). FIG. 7D shows the nucleotide sequence of IF-HT4*-PDI.c (SEQ ID NO:30; used to prepare construct number 1955). FIG. 7E shows the nucleotide sequence of IF-HT5*-PDI.c (SEQ ID NO:31; used to prepare construct number 1956). FIG. 7F shows the nucleotide sequence of IF-HT6*-PDI.c (SEQ ID NO:32 used to prepare construct number 1957). FIG. 7G shows the nucleotide sequence of IF-HT7*-PDI.c (SEQ ID NO:33; used to prepare construct number 1958). FIG. 7H shows the nucleotide sequence of IF-HT8*-PDI.c (SEQ ID NO:34; used to prepare construct number 1959). FIG. 7I shows a schematic representation of construct number 1952 comprising a plant kozak sequence (Kozak1) using SEQ ID NO:27 (FIG. 7A). Constructs 1953-1959 comprise the same features as construct 1952, except that each construct (1953-1959) comprises a modified plant Kozak sequence (Kozak1) as shown in FIGS. 7B to 7H (SEQ ID NOs: 28 to 34), respectively.

FIG. 8 shows sequence components used to prepare construct numbers 484 and 1805 (2X35S/CPMV HT PDISP/H1 California NOS and 2X35S/CPMV HT+ PDISP/H1 California NOS, respectively; see Example 4). Construct number 484 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (PDISP/H1 California). Construct number 1805 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide. NOS: nopaline synthase terminator. FIG. 8A shows the nucleotide sequence of PDISP/H1 California (SEQ ID NO: 35). FIG. 8B shows the amino acid sequence of PDISP/H1 California (SEQ ID NO: 36). FIG. 8C shows a schematic representation of construct number 484 (2X35S/CPMV HT; reference construct). FIG. 8D shows a schematic representation of construct number 1805 (2X35S/CPMV HT+).

FIG. 9 shows sequence components used to prepare construct numbers 409 and 2319 (2X35S/CPMV HT PDISP/H5 Indonesia NOS; CPMV HT+ PDISP/H5 Indonesia NOS, respectively; see Example 5). Construct number 409 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (PDISP/H5 Indonesia). Construct number 2319 includes a CPMV 5'UTR comprising 160 nucleotides, a stuffer fragment comprising an incomplete M protein, a multiple cloning site, and a plant kozak sequence and is an example of a CPMV HT+ based construct. NOS: nopaline synthase terminator. FIG. 9A shows the nucleotide sequence of PDISP/H5 Indonesia (SEQ ID NO: 37). FIG. 9B shows the amino acid sequence of PDISP/H5 Indonesia (SEQ ID NO: 38). FIG. 9C shows a schematic representation of construct number 409 (2X35S/CPMV HT; reference construct). FIG. 9D shows a schematic representation of construct number 2319 (2X35S/CPMV HT+).

FIG. 10 shows sequence components used to prepare construct numbers 2140 and 2142 (2X35S/CPMV HT H7 Hangzhou NOS; CPMV HT+H7 Hangzhou NOS, respectively; see Example 6). Construct number 2140 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (PDISP/H7 Hangzhou). Construct number 2142 includes a CPMV 5'UTR comprising 160 nucleotides, a stuffer fragment comprising an incomplete M protein, a multiple cloning site, and a plant kozak sequence and is an example of a CPMV HT+ based construct. NOS: nopaline synthase terminator. FIG. 10A shows the nucleotide sequence of native H7 Hangzhou (SEQ ID NO: 39). FIG. 10B shows the amino acid sequence of native H7 Hangzhou (SEQ ID NO: 40). FIG. 10C shows a schematic representation of construct number 2140 (2X35S/CPMV HT; reference construct). FIG. 10D shows a schematic representation of construct number 2142 (2X35S/CPMV HT+).

FIG. 11 shows sequence components used to prepare construct numbers 2130 and 2146 (2X35S/CPMV HT H7 Hangzhou+H5 Indonesia TMCT NOS; CPMV HT+H7 Hangzhou+H5 Indonesia TMCT NOS, respectively; see Example 7). Construct number 2130 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (PDISP/H7 Hangzhou+H5 Indonesia TMCT). Construct number 2146 includes a CPMV 5'UTR comprising 160 nucleotides, a stuffer fragment comprising an incomplete M protein, a multiple cloning site, and a plant kozak sequence and is an example of a CPMV HT+ based construct. NOS: nopaline synthase terminator. FIG. 11A shows the nucleotide sequence of H7 Hangzhou+H5 Indonesia TMCT (SEQ ID NO: 41). FIG. 11B shows the amino acid sequence of H7 Hangzhou+H5 Indonesia TMCT (SEQ ID NO: 42). FIG. 11C shows a schematic representation of construct number 2130 (2X35S/CPMV HT; reference construct). FIG. 11D shows a schematic representation of construct number 2146 (2X35S/CPMV HT+).

FIG. 12 shows sequence components used to prepare construct numbers 1039 and 1829 (2X35S/CPMV HT PDISP/HA B Brisbane (PrL-) NOS and 2X35S/CPMV HT+ PDISP/HA B Brisbane (PrL-) NOS, respectively; see Example 8). Construct number 1039 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (PDISP/HA B Brisbane (PrL-)). Construct number 1829 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide; NOS: nopaline synthase terminator; PrL-: deleted proteolytic loop. FIG. 12A shows the nucleotide sequence of PDISP/HA B Brisbane (PrL-) (SEQ ID NO: 43). FIG. 12B shows the amino acid sequence of PDISP/HA B Brisbane (PrL-); SEQ ID NO: 44).

FIG. 13 shows sequence components used to prepare construct numbers 1067 and 1875 (2X35S/CPMV HT PDISP/HA B Brisbane (Prl-)+H1 California TMCT NOS and 2X35S/CPMV HT+ PDISP/HA B Brisbane (PrL-)+H1 California TMCT NOS, respectively; see Example 9). Construct number 1067 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (PDISP/HA B Brisbane (PrL-)+H1 California TMCT). Construct number 1875 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide; NOS: nopaline synthase terminator; PrL-: deleted proteolytic loop; TMCT: transmembrane domain cytoplasmic tail. FIG. 13A shows the nucleotide sequence of PDISP/HA B Brisbane (PrL-)+H1 California TMCT (SEQ ID NO: 45). FIG. 13B shows the amino acid sequence of PDISP/HA B Brisbane (PrL-)+H1 California TMCT (SEQ ID NO: 46).

FIG. 14 shows sequence components used to prepare construct numbers 2072 and 2052 (2X35S/CPMV HT PDISP/HA B Massachusetts (PrL-) NOS and 2X35S/CPMV HT+ PDISP/HA B Massachusetts (PrL-) NOS, respectively; see Example 10). Construct number 2072 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (PDISP/HA B Massachusetts (PrL-)). Construct number 2052 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide; NOS: nopaline synthase terminator; PrL-: deleted proteolytic loop. FIG. 14A shows the nucleotide sequence of PDISP/HA B Massachusetts (PrL-) (SEQ ID NO: 47). FIG. 14B shows the amino acid sequence of PDISP/HA B Massachusetts (PrL-) (SEQ ID NO: 48). FIG. 14C shows a schematic representation of construct number 2072 (2X35S/CPMV HT; reference construct). FIG. 14D shows a schematic representation of construct number 2052 (2X35S/CPMV HT+).

FIG. 15 shows sequence components used to prepare construct numbers 2074 and 2062 (2X35S/CPMV HT PDISP/HA B Massachusetts (PrL-)+H1 California TMCT NOS and 2X35S/CPMV HT+ PDISP/HA B Massachusetts (PrL-)+H1 California TMCT NOS, respectively; see Example 11). Construct number 2074 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (PDISP/HA B Massachusetts (PrL-)+H1 California TMCT). Construct number 2062 includes a CPMV 5'UTR comprising 160 nucleotides, a stuffer fragment comprising an incomplete M protein, a multiple cloning site, and a plant kozak sequence and is an example of a CPMV HT+ based construct. PDISP: protein disulfide isomerase signal peptide; NOS: nopaline synthase terminator; PrL-: deleted proteolytic loop; TMCT: transmembrane domain cytoplasmic tail. FIG. 15A shows the nucleotide sequence of PDISP/HA B Massachusetts (PrL-)+H1 California TMCT (SEQ ID NO: 49). FIG. 15B shows the amino acid sequence of PDISP/HA B Massachusetts (PrL-)+H1 California TMCT (SEQ ID NO: 50). FIG. 15C shows a schematic representation of construct number 2074 (2X35S/CPMV HT; reference construct). FIG. 15D shows a schematic representation of construct number 2062 (2X35S/CPMV HT+).

FIG. 16 shows sequence components used to prepare construct numbers 1445 and 1839 (2X35S/CPMV HT HA B Wisconsin (PrL-) NOS, and 2X35S/CPMV HT+HA B Wisconsin (PrL-) NOS, respectively; see Example 12). Construct number 1445 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (HA B Wisconsin (PrL-)). Construct number 1839 includes a CPMV 5'UTR comprising 160 nucleotides, a stuffer fragment comprising an incomplete M protein, a multiple cloning site, and a plant kozak sequence and is an example of a CPMV HT+ based construct. PrL-: deleted proteolytic loop; NOS: nopaline synthase terminator. FIG. 16A shows the nucleotide sequence of HA B Wisconsin (PrL-) (SEQ ID NO: 51). FIG. 16B shows the amino acid sequence of HA B Wisconsin (PrL-) (SEQ ID NO: 52).

FIG. 17 shows sequence components used to prepare construct numbers 1454 and 1860 (2X35S/CPMV HT HA B Wisconsin (PrL-)+H1 California TMCT NOS and 2X35S/CPMV HT+HA B Wisconsin (PrL-)+H1 California TMCT NOS, respectively; see Example 13). Construct number 1454 incorporates a prior art CPMV-HT sequence (CPMV 5'UTR with mutated start codon at position 161 fused to a sequence encoding an incomplete M protein) and does not comprise a heterologous kozak sequence between the 5'UTR and the nucleotide sequence of interest (HA B Wisconsin (PrL-)+H1 California TMCT). Construct number 1860 includes a CPMV 5'UTR comprising 160 nucleotides, a stuffer fragment comprising n incomplete M protein, a multiple cloning site, and a plant kozak sequence and is an example of a CPMV HT+ based construct. NOS: nopaline synthase terminator; PrL-: deleted proteolytic loop; TMCT: transmembrane domain cytoplasmic tail. FIG. 17A shows the nucleotide sequence of HA B Wisconsin (PrL-)+H1 California TMCT (SEQ ID NO: 53). FIG. 17B shows the amino acid sequence of PDISP/HA B Wisconsin (PrL-)+H1 California TMCT (SEQ ID NO: 54).

DETAILED DESCRIPTION

Figure 2:
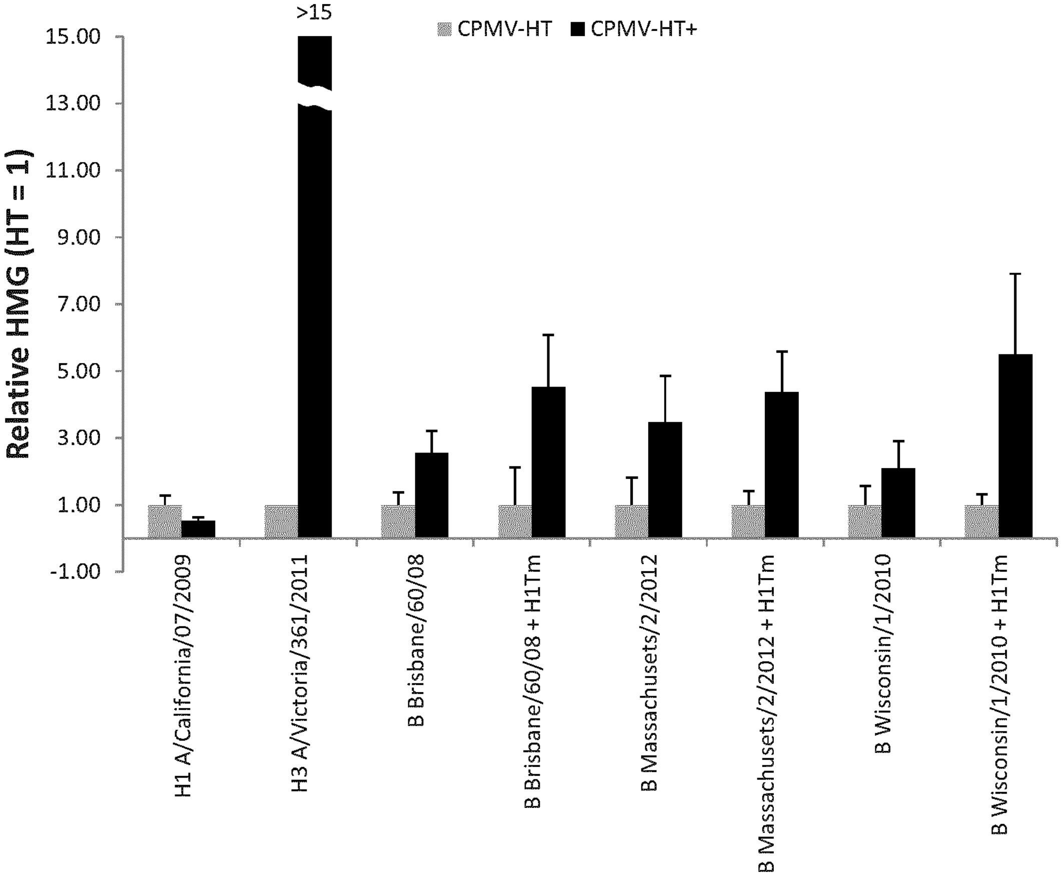
FIG. 2 shows the relative hemagglutination titre (HMG) in crude protein extracts of proteins produced in plants comprising CPMV-HT (prior art) expression constructs, and CPMV HT+ based expression constructs, operatively linked with a nucleotide sequence of interest. Data for the expression of HA from H1 A/California/07/2009 with a PDI signal peptide (construct number 484: CPMV HT; and construct number 1805: CPMV HT+; see Example 4), H3 A/Victoria/361/2011 with a PDI signal peptide (construct number 1391: CPMV HT; and construct number 1819: CPMV HT+; see Examples 1 and 2, respectively), B Brisbane/60/08 with deleted proteolytic loop and with a PDI signal peptide (construct number 1039: CPMV HT; and construct number 1829: CPMV HT+; see example 8), B Brisbane/60/08+H1TM with deleted proteolytic loop, with transmembrane domain and cytoplasmic tail replaced by those of H1 A/California/07/2009, and with a PDI signal peptide (construct number 1067: CPMV HT; and construct number 1875: CPMV HT+; see example 9), B Massachusetts/2/2012 with deleted proteolytic loop, and with a PDI signal peptide (construct number 2072: CPMV HT; and construct number 2052: CPMV HT+; see Example 10), B Massachusetts/2/2012+H1Tm with deleted proteolytic loop, with transmembrane domain and cytoplasmic tail replaced by those of H1 A/California/07/2009 and with a PDI signal peptide (construct number 2074: CPMV HT; and construct number 2062: CPMV HT+; see Example 11), B Wisconsin/1/2010 with deleted proteolytic loop and with the native signal peptide (construct number 1445: CPMV HT; and construct number 1839: CPMV HT+; see Example 12), and B Wisconsin/1/2010+H1Tm with deleted proteolytic loop, with transmembrane domain and cytoplasmic tail replaced by those of H1 A/California/07/2009 and with the native signal peptide (construct number 1454: CPMV HT; and construct number 1860: CPMV HT+; see Example 13), are shown.

The present invention relates to the expression of proteins of interest in plants. The present invention also provides methods and compositions for the production of proteins of interest in plants.

In the description that follows, a number of terms are used extensively, the following definitions are provided to facilitate understanding of various aspects of the invention. Use of examples in the specification, including examples of terms, is for illustrative purposes only and is not intended to limit the scope and meaning of the embodiments of the invention herein.

As used herein, the use of the word "a" or "an" when used herein in conjunction with the term "comprising" may mean "one," but it is also consistent with the meaning of "one or more," "at least one" and "one or more than one". The term "about" refers to an approximately +/−10% variation from a given value. The term "plurality", means more than one, for example, two or more, three or more, four or more, and the like.

The present invention provides nucleic acids, expression enhancers, and expression systems to produce proteins of interest in plants, comprising a comovirus 5' untranslated region (UTR) and a modified, lengthened, or truncated stuffer sequence. Plant cells, plant tissues, whole plants, inoculum, nucleic acids, constructs, comprising sequences of interest, and methods of expressing a protein of interest in plants are also provided.

An example of an expression enhancer of the present invention includes, but is not limited to CPMV HT+, as shown in FIG. 1A. Non-limiting example of the nucleotide sequence of CPMV HT+ is provided with reference to SEQ ID NO's: 1, 3 and 4.

The expression enhancer CPMV HT+ may be operatively linked at the 5'end of the enhancer sequence with a regulatory region that is active in a plant, and operatively linked to a nucleotide sequence of interest at the 3'end of the expression enhancer (FIG. 1A), in order to drive expression of the nucleotide sequence of interest within a plant host.

Expression systems to produce one or more proteins of interest in a plant using either CPMV HT+ are also provided. The expression systems described herein comprise an expression cassette comprising CPMV HT+, or a sequence that comprises from 80% to 100%, or any amount therebetween, sequence similarity with CPMV HT+. The expression cassette comprising CPMV HT+, may further comprise a regulatory region that is active in a plant that is operatively linked to the 5'end of the expression enhancer. A nucleotide sequence of interest may be operatively linked to the 3'end of the expression cassette so that when introduced within a plant, expression of the nucleotide sequence of interest within a plant host is achieved.

With reference to FIGS. 1A and 1B there are shown expression enhancers comprising a 5' UTR sequence from a comovirus genome (comovirus 5' UTR) along with a modified M protein. In FIGS. 1A and 1B, a prior art CPMV HT enhancer comprising an incomplete M protein (Sainsbury and Lomonossoff, 2008, Plant Physiology; 148: 1212-1218; WO 2009/087391; which are incorporated herein by reference) is shown, along with the CPMV HT+ of the present invention.

The prior art CPMV HT expression enhancer (Sainsbury and Lomonossoff, 2008, Plant Physiology; 148: 1212-1218; WO 2009/087391; which are incorporated herein by reference) comprises nucleotides 1-160 of the CPMV 5' UTR with a modified ATG at position 115 (ATG is modified to CGT), fused to an incomplete M protein comprising nucleotides 161-509 of SEQ ID NO: 2, the incomplete M protein consisting of a modified ATG at position 162 (ATG is modified to ACG), and a linker sequence (see SEQ ID NO:2). A nucleotide of interest is fused to the 3'end of the linker sequence (see FIGS. 1A and 1B). The prior art CPMV HT lacks a plant Kozak sequence immediately upstream from the location that the nucleotide of interest is fused to the expression enhancer.

The CPMV HT+ of the present invention may comprise nucleotides 1-160 of the CPMV 5' UTR with a modified ATG at position 115-117 (where ATG is modified to GTG; A at position 115 is modified to G), fused to a stuffer sequence that is modified and comprises: a modified ATG (ATG is modified to ACG at positions 161-163; with "T" modified to "C" at position 162), an incomplete M protein, a linker sequence and a plant kozak sequence. Non-limiting examples of a CPMV HT+ nucleotide sequence are shown in SEQ ID NO's:1 and 4. A nucleotide of interest may be fused to the 3'end of the kozak sequence, for example a plant kozak sequence, of CPMV HT+ (see FIGS. 1A and 1B).

The 5'UTR of the expression enhancer of the present invention may also include an "A" at position 115 and include the native ATG sequence at nucleotides 115-117 as shown in SEQ ID NO:4, fused to a stuffer sequence that is modified and comprises: a modified ATG at nucleotides 161-163, to ACG (where "T" at position 162 is modified to a "C") an incomplete M protein, a linker sequence and a plant kozak sequence. An expression enhancer comprising a native or wild type "A" at position 115, may be referred to as CPMV HT+ [WT115]. A non-limiting example of a CPMV HT+ [WT115] nucleotide sequence is shown in SEQ ID NO:3. A nucleotide of interest may be fused to the 3'end of the plant kozak sequence of CPMV HT+[WT115] (see FIGS. 1A and 1B). CPMV HT+ [WT115] may be considered a variant of the CPMV HT+, as CPMV HT+ comprises the nucleotide "G" at position 115 (SEQ ID NO:1). Also, CPMV HT+ [511] may also be considered a variant of CPMV HT+, since CPMV HT+ [511] includes nucleotides 161-511 of the incomplete M protein (see SEQ ID NO:56). In this manner, the term "CPMV HT+" is a generic term that includes variants such as CPMV HT+ [WT115] and CPMV HT+ [511].

Non-limiting examples of a CPMV HT+ expression enhancer are presented in SEQ ID NO's:1, 3 and 4, however, it is to be understood that variations or modifications in the stuffer sequence of CPMV HT+ and CPMV HT+[WT115] may be made without departing from the present invention, provided that the stuffer fragment comprises an incomplete M protein, and when fused to a nucleotide sequence of interest, a kozak sequence active in a plant, for example a plant kozak sequence, is positioned at the 5' end of the nucleotide sequence of interest. Another example of a CPMV HT+ expression enhancer (comprising an M protein-native kozak sequence) is provided in SEQ ID NO:56 (CPMV HT+ [511]).

The stuffer sequence may be modified by insertion, truncation or deletion, so that the incomplete M protein sequence is longer, truncated or shortened when compared to the initial (unmodified) incomplete M protein sequence of the prior art enhancer CPMV HT (Sainsbury and Lomonossoff, 2008, Plant Physiology; 148: 1212-1218; WO 2009/087391; which are incorporated herein by reference). In addition to the incomplete M protein, the stuffer sequence of the CPMV HT+ expression enhancer of the present invention may further comprise one or more restriction sites (a polylinker, a multiple cloning site, one or more cloning sites), one or more plant kozak sequences or an M protein-native kozak sequence, one or more linker sequences, one or more recombination sites, or a combination thereof. For example, which is not to be considered limiting, a stuffer sequence may comprise in series, an incomplete M protein (nucleotides 161-509 of SEQ ID NO's: 1 or 2, or nucleotide 161-511 of SEQ ID NO:56), a multiple cloning site of a desired length fused to a kozak sequence active in a plant, for example a plant kozak sequence.

The nucleotide sequence of interest may be fused (operatively linked) to the CPMV HT+ (or CPMV HT+ [WT115], or CPMV HT+ [511]) enhancer sequence of the present invention using a variety of approaches. For example, which are not to be considered limiting:

1) A nucleotide sequence of interest, for example a nucleic acid encoding a protein of interest, may be fused to the CPMV HT+ expression enhancer immediately after the stuffer fragment consisting of an incomplete M protein sequence (with or without a multiple cloning site). In this case, the nucleotide sequence of interest is fused to the 3' end of the incomplete M protein sequence (or multiple cloning site if present), and the nucleotide sequence of interest includes at its 5' end, a plant kozak sequence immediately upstream from the ATG initiation site of the nucleotide sequence of interest.

2) The nucleotide sequence of interest, may be fused to the expression enhancer comprising a stuffer fragment (including an incomplete M protein, an optional multiple cloning site, and a plant kozak sequence), immediately after the plank kozak sequence located at the 3' end of the stuffer fragment. In this case, the nucleotide sequence of interest would not include a corresponding multiple cloning site or plant kozak sequence.

3) The nucleotide sequence of interest may be fused to the CPMV HT+ expression enhancer using the multiple cloning site. In this case, the nucleotide sequence of interest may include at its 5' end a corresponding cloning site to permit fusion with the expression enhancer, and a plant kozak sequence immediately upstream from the ATG initiation site of the nucleotide sequence of interest.

The overall result using any of the above methods, is a construct, or an expression cassette, comprising a plant regulatory region in operative association (operatively linked) with a 5'UTR sequence, the 5'UTR sequence is fused to the 5'end of a stuffer fragment comprising an incomplete M protein fused to a plant kozak sequence, the 3' end of the plant kozak sequence fused to the 5' end of the nucleotide sequence of interest. The construct may further comprise a sequence comprising a comovirus 3' untranslated region (UTR), for example, a plastocyanin 3' UTR, or other 3'UTR that is active within a plant, and a terminator sequence, for example a NOS terminator, operatively linked to the 3'end of the nucleotide sequence of interest (see FIG. 1A).

A plant expression system comprising a first nucleic acid sequence comprising a regulatory region, operatively linked with one or more than one expression enhancer as described herein (e.g. CPMV HT+, CPMV HT+[WT115], CPMV HT+ [511]), and a nucleotide sequence of interest is also provided. Furthermore, a nucleic acid comprising a promoter (regulatory region) sequence, an expression enhancer (e.g. CPMV HT+, CPMV HT+[WT115], or CPMV HT+ [511]) comprising a comovirus 5'UTR and a stuffer sequence with a plant kozak sequence fused to one or more nucleic acid sequences encoding one or more proteins of interest are described. The nucleic acid may further comprise a sequence comprising a comovirus 3' untranslated region (UTR), for example, a plastocyanin 3' UTR, or other 3'UTR active in a plant, and a terminator sequence, for example a NOS terminator, operatively linked to the 3'end of the nucleotide sequence of interest (see FIG. 1A), so that the nucleotide sequence of interest is inserted upstream from the comovirus 3' untranslated region (UTR), plastocyanin 3' UTR, or other 3'UTR sequence.

By "operatively linked" it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

"Expression enhancer(s)", "enhancer sequence(s)" or "enhancer element(s)", as referred to herein, include sequences derived from, or that share from about 80% to 100%, or any amount therebetween, sequence similarity with nucleotides 1-160 of SEQ ID NO: 1. An enhancer sequence can enhance expression of a downstream heterologous open reading frame (ORF) to which they are attached.

The term "5'UTR" or "5' untranslated region" or "5' leader sequence" refers to regions of an mRNA that are not translated. The 5'UTR typically begins at the transcription start site and ends just before the translation initiation site or start codon (usually AUG in an mRNA, ATG in a DNA sequence) of the coding region. The 5'UTR may be modified in length, or by mutating a naturally occurring start codon or translation initiation site such that the codon no longer functions as start codon and translation may initiate at an alternate initiation site. For example the ATG starting at positions 115, 161, 512, 524 or a combination thereof, of the native CPMV 5'UTR may be modified to remove the ATG sequence, for example to ACG, GTG, or CGT or other non-ATG sequence.

By "incomplete M protein" it is meant an M protein coding sequence comprising from about 10 to about 351 nucleotides, or any amount therebetween, of nucleotides 161-509 of SEQ ID NO:1, or nucleotides 161-511 of SEQ ID NO:56. Nucleotides 161-509 of SEQ ID NO:1, or nucleotides 161-511 of SEQ ID NO:56, correspond to the sequence of the M protein present in the native CPMV RNA 2 genome sequence (see SEQ ID NO:55 herein; also see Table 1 of WO 2009/087391; which is incorporated herein by reference) with a modification (substitution) to one or more of the nucleotides at positions 161-163 to remove the "atg" start site. Non limiting examples of an incomplete M protein sequence include, a nucleotide sequence comprising from about 80% to 100% sequence similarity, or any amount therebetween, with the sequence defined by nucleotides 161 to 509 of SEQ ID NO's: 1-4, nucleotides 161-511 of SEQ ID NO:55, or nucleotides 161-511 of SEQ ID NO:56. The sequence may be modified to remove a start codon or start site so that the sequence does not comprise the "atg" codon. Furthermore, non limiting examples of an incomplete M protein comprise nucleotides 161 to 509 of SEQ ID NO's: 1-4, nucleotides 161-511 of SEQ ID NO:55, or nucleotides 161-511 of SEQ ID NO:56. Non-limiting examples of a sequence comprising modifications to the native CPMV RNA 2 sequence (SEQ ID NO:55) for use as described herein, include CPMV HT+, (SEQ ID NO:1), and CPMV HT+ [511] (SEQ ID NO:56).

SEQ ID NO:55 comprises a segment of the native (wild-type) sequence of the CPMV RNA 2 genome from nucleotides 1-514 (full length sequence of the native CMPV RNA-2 genomic segment is presented in Table 1 of WO 2009/087391; which is incorporated herein by reference). The 5'UTR sequence from nucleotides 1-511 of SEQ ID NO:55 comprises wild-type "atg" sequences starting at positions 115 and 161 (italics bold), and an incomplete M protein underlined, from nucleotides 161-511 (the "atg" at position 512 is also shown for context; initiation at "atg" at position 512 of the native 5' region of CPMV RNA-2 results in the synthesis of a 95K polyprotein):

SEQ ID NO: 55

1 tattaaaatc ttaataggtt ttgataaaag cgaacgtggg gaaacccgaa ccaaaccttc 61 ttctaaactc tctctcatct ctcttaaagc aaacttctct cttgtctttc ttgc*atg*agc 121 gatcttcaac gttgtcagat cgtgcttcgg caccagtaca *acg*ttttctt tcactgaagc 181 gaaatcaaag atctctttgt ggacacgtag tgcggcgcca ttaaataacg tgtacttgtc 241 ctattcttgt cggtgtggtc ttgggaaaag aaagcttgct ggaggctgct gttcagcccc 301 atacattact tgttacgatt ctgctgactt tcggcgggtg caatatctct acttctgctt 361 gacgaggtat tgttgcctgt acttctttct tcttcttctt gctgattggt tctataagaa 421 atctagtatt ttctttgaaa cagagttttc ccgtggtttt cgaacttgga gaaagattgt 481 taagcttctg tatattctgc ccaaatttga aatg...

The 5'UTR from nucleotides 1-160 of the CPMV RNA-2 sequence (see SEQ ID NO: 1), starts at the transcription start site to the first in frame initiation start codon (at position 161), which serve as the initiation site for the production of the longer of two carboxy coterminal proteins encoded by a wild-type comovirus genome segment (the shorter of the two encoded protein starts at position 155). Furthermore a 'third' initiation site at (or corresponding to) position 115 in the CPMV RNA-2 genomic sequence may also be mutated, deleted or otherwise altered. It has been shown that removal of AUG 115 in addition to the removal of AUG at position 161 enhances expression of a nucleotide sequence of interest when combined with an incomplete M protein (Sainsbury and Lomonossoff, 2008, *Plant Physiology;* 148: 1212-1218; WO 2009/087391; which are incorporated herein by reference).

The expression enhancer may comprise nucleotides 1-509 of SEQ ID NO's:1, 3 or 4, nucleotides 1-511 of SEQ ID NO: 55, or nucleotides 1-511 of SEQ ID NO:56, and includes a CPMV 5' untranslated region (UTR) fused to a stuffer fragment comprising an incomplete M protein and a plant kozak sequence at the 3' end of the stuffer fragment, and optionally, a multiple cloning site, or a sequence that comprises from 80% to 100%, or any amount therebetween, sequence similarity with nucleotides 1-160 of SEQ ID NO:1, nucleotides 161-509 of SEQ ID NO:1, nucleotides 1-509 of SEQ ID NO:1, nucleotides 1-511 of SEQ ID NO:55, or nucleotides 1-511 of SEQ ID NO:56, and includes a stuffer fragment comprising an incomplete M protein, and further includes and a kozak sequence that is active in a plant, either a plant kozak sequence or an M protein-native kozak sequence, at the 3' end of the stuffer fragment, and optionally a multi-cloning site, and exhibits the property of enhancing expression of a nucleotide sequence encoding a heterologous open reading frame that is operatively linked to the expression enhancer, when compared to the expression of the same nucleotide sequence encoding a heterologous open reading frame operatively linked to the prior art "CPMV HT" enhancer sequence (SEQ ID NO:2; Sainsbury F., and Lomonossoff G. P., 2008, Plant Physiol. 148: pp. 1212-1218; which is incorporated herein by reference).

The stuffer sequence may include from about 50 to 351 nucleotides, or any amount therebetween, of an incomplete M protein, for example but not limited to nucleotides 161-509 of SEQ ID NO:1 or nucleotides 161-511 of SEQ ID NO's:55 or 56, a plant kozak sequence, or an M protein-native kozak sequence, located at the 3' end of the stuffer fragment, and a multiple cloning site (MCS) of from about 0 to 100 nucleotides in length, or any amount therebetween located between the sequence encoding the incomplete M protein and the kozak sequence, for example a plant kozak sequence. The stuffer sequence may therefore be of a length from about 50 to about 500 nucleotides, or any amount therebetween, fused to the 3' end of the CPMV 5'UTR sequence, for example the stuffer sequence may be of a length from 50, 60, 70, 80, 90, 100, 120, 140, 160, 180, 200, 220, 240, 260, 280, 300, 320, 340, 360, 380, 400, 420, 440, 460, 480, 500 nucleotides, or any amount therebetween, fused to the 3' end of the CPMV 5'UTR sequence.

The expression enhancer may further comprise one or more "restriction site(s)" or "restriction recognition site(s)", "multiple cloning site", "MCS", "cloning site(s)" "polylinker sequence" or "polylinker" to facilitate the insertion of the nucleotide of interest into the plant expression system. Restrictions sites are specific sequence motifs that are recognized by restriction enzymes as are well known in the art. The expression enhancer may comprise one or more restriction sites or cloning sites that are located downstream (3') of the incomplete M protein. The one or more restriction sites or cloning sites may be located upstream (5') of one or more kozak sequences, and located between a incomplete M protein and a kozak sequence. The polylinker sequence (multiple cloning site) may comprise any sequence of nucleic acids that are useful for adding and removing nucleic acid sequences, including a nucleotide sequence encoding a protein of interest, to the 3' end of the 5'UTR. A polylinker sequence may comprise from 4 to about 100 nucleic acids, or any amount therebetween.

The CPMV HT+ expression enhancer (including CPMV HT+ [WT115]; CPMV HT+ [511]), defined by the sequence of SEQ ID NO's:1, 3, 4 or 56 are examples which are not to be considered limiting, of expression enhancers of the present invention. Expression cassettes or vectors comprising CPMV HT+, CPMV HT+ [WT115], or CPMV HT+ [511], as defined by SEQ ID NO's:1, 3, 4, or 56 and that further include a plant regulatory region in operative association with the expression enhancer sequence, and a nucleotide sequence of interest (GOI; with a 3'UTR and terminator sequences) fused to the 3' end of the expression enhancer are also included in the present invention. Variants of the CPMV HT+ expression enhancer as defined by SEQ DI NO's:1, 3, 4 or 56 are also included in the present invention.

If the enhancer sequence comprises a CPMV 5'UTR sequence, an incomplete M protein, and a kozak sequence active in a plant, for example a plant kozak sequence, at the 3' end of the enhancer sequence, then the enhancer sequence may be termed a "CPMV HT+ enhancer sequence", provided that the CPMV HT+ enhancer sequence exhibits the property of enhancing expression of a nucleotide sequence encoding a heterologous open reading frame that is operatively linked to the expression enhancer, when compared to the expression of the same nucleotide sequence encoding a heterologous open reading frame operatively linked to the prior art "CPMV HT" enhancer sequence (SEQ ID NO:2; Sainsbury F., and Lomonossoff G. P., 2008, Plant Physiol. 148: pp. 1212-1218; which is incorporated herein by reference).

Variations that may exist in CPMV HT+ may include:

1) modifications in the length of the incomplete M protein from about 50 to about 351 nucleotides or any amount therebetween;

2) modification in the multiple cloning site (MCS), both the sequences included, and the length of the MCS, of from about 0 to about 100 nucleotides in length, or any length therebetween; and 3) the kozak sequence may be any kozak sequence that is active in a plant and include a plant kozak sequence, or an M protein-native kozak sequence.

For example, the CPMV 5' UTR comprises nucleotides 1 to 160 of SEQ ID NO's:1 or 3, or from about 80% to about 100%, or any amount therebetween, sequence similarity to nucleotides 1-160 of SEQ ID NO's:1 or 3.

SEQ ID NO: 1 is an example of an expression enhancer comprising CPMV HT+ (nucleotide 1-160, 5'UTR, including modified ATG at positions 115 (GTG) lower case bold and italics; stuffer fragment comprising: an incomplete M protein underlined, nucleotides 161-509, with modified nucleotide at 162 (ACG); a multiple cloning site, italics, nucleotides 510-528; and a plant kozak sequence, caps and bold, nucleotides 529-534):

(SEQ ID NO: 1)

```
 1 tattaaaatc ttaataggtt ttgataaaag cgaacgtggg gaaacccgaa ccaaaccttc

61 ttctaaactc tctctcatct ctcttaaagc aaacttctct cttgtctttc ttgcgtgagc
```

-continued

```
121gatcttcaac gttgtcagat cgtgcttcgg caccagtaca acgttttctt tcactgaagc

181gaaatcaaag atctctttgt ggacacgtag tgcggcgcca ttaaataacg tgtacttgtc

241ctattcttgt cggtgtggtc ttgggaaaag aaagcttgct ggaggctgct gttcagcccc

301atacattact tgttacgatt ctgctgactt tcggcgggtg caatatctct acttctgctt

361gacgaggtat tgttgcctgt acttctttct tcttcttctt gctgattggt tctataagaa

421atctagtatt ttctttgaaa cagagttttc ccgtggtttt cgaacttgga gaaagattgt

481taagcttctg tatattctgc ccaaatttgt tcgggcccaa taccgcggAG AAAA
```

Constructs 1819, 1805, 2319, 2142, 2146, 1829, 1875, 2052, 2062, 1839 and 1860 (see Examples 1, and 4-13, respectively) are representative of constructs comprising a CPMV HT+ expression enhancer comprising SEQ ID NO:1. Results using these constructs may be found in FIGS. 2 and 3.

SEQ ID NO:2 comprises a "CPMV HT" expression enhancer as known in the prior art (e.g. FIG. 1 of Sainsbury and Lomonossoff 2008, Plant Physiol. 148: pp. 1212-1218; which is incorporated herein by reference). CPMV HT includes the 5'UTR sequence from nucleotides 1-160 of SEQ ID NO:2 with modified nucleotides at position 115 (cgt), and an incomplete M protein with a modified nucleotide at position 162 (acg), and lacks a plant kozak sequence (5'UTR: nucleotides 1-160; incomplete M protein underlined, nucleotides 161-509). SEQ ID NO:2 also includes a multiple cloning site (italics, nucleotides 510-517) which is not present in the prior art CPMV HT sequence as described by Sainsbury and Lomonossoff 2008:

```
                                                                SEQ ID NO: 2
  1tattaaaatc ttaataggtt ttgataaaag cgaacgtggg gaaacccgaa ccaaaccttc

 61ttctaaactc tctctcatct ctcttaaagc aaacttctct cttgtctttc ttgcgtgagc

121gatcttcaac gttgtcagat cgtgcttcgg caccagtaca acgttttctt tcactgaagc

181gaaatcaaag atctctttgt ggacacgtag tgcggcgcca ttaaataacg tgtacttgtc

241ctattcttgt cggtgtggtc ttgggaaaag aaagcttgct ggaggctgct gttcagcccc

301atacattact tgttacgatt ctgctgactt tcggcgggtg caatatctct acttctgctt

361gacgaggtat tgttgcctgt acttctttct tcttcttctt gctgattggt tctataagaa

421atctagtatt ttctttgaaa cagagttttc ccgtggtttt cgaacttgga gaaagattgt

481taagcttctg tatattctgc ccaaatttgt cgggccc
```

Constructs comprising CPMV HT are used herein as reference constructs, so that the expression levels of a nucleotide sequence of interest, or a product encoded by the nucleotide sequence of interest produced using a construct comprising CPMV HT+, CPMV HT+ [WT115] or CPMV HT+ [511], may be compared. Constructs 1391, 484, 409, 2140, 2130, 1039, 1067, 2072, 2074, 1445 and 1454 (see Examples 1, and 4-13, respectively) are representative of the reference construct CPMV HT, and comprise SEQ ID NO:2. Results using these constructs may be found in FIGS. 2 and 3.

Figure 4A:
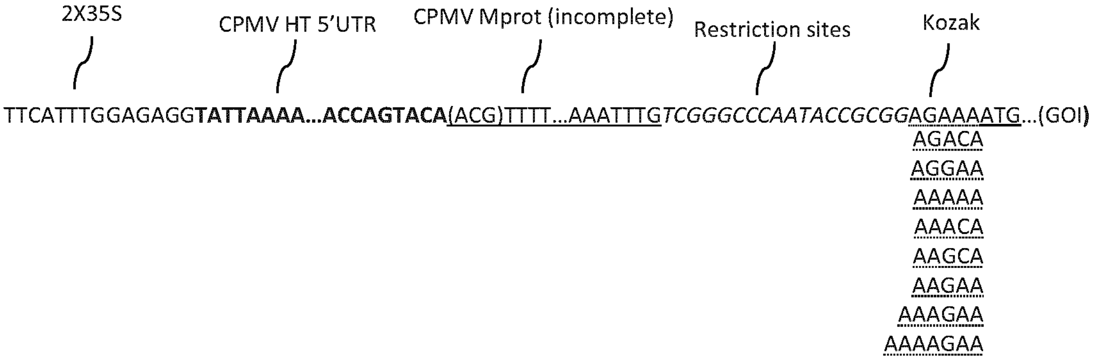
FIG. 4A shows examples of variants of plant Kozak sequences tested. Constructs showing a partial sequence of the CPMV HT+, a plant regulatory region, a 5'UTR, a stuffer fragment, and a nucleotide sequence of interest (GOI). In this non-limiting example, the construct comprises a 2X35S regulatory region, CPMV HT+ comprising a stuffer fragment comprising an incomplete M protein and a multiple cloning site (restriction sites), a plant kozak sequence (the 5' end of a nucleotide sequence of interest is also indicated: "ATG . . . GOI"; where the GOI is H3 A/Victoria/361). The construct sequence in FIG. 4A shows bases 734-931 of SEQ ID NO:26 (expression cassette number 1800, FIG. 7E), with an internal portion omitted for brevity. Variants of plant kozak sequences are also shown below the sequence (also see FIG. 7). Each variant plant Kozak sequence was located between the 3' end of the stuffer fragment, and the 5'-ATG site of the nucleotide sequence of interest (in these non-limiting examples, H3 A/Victoria/361). The other elements of the constructs remained the same.
Figure 4B:
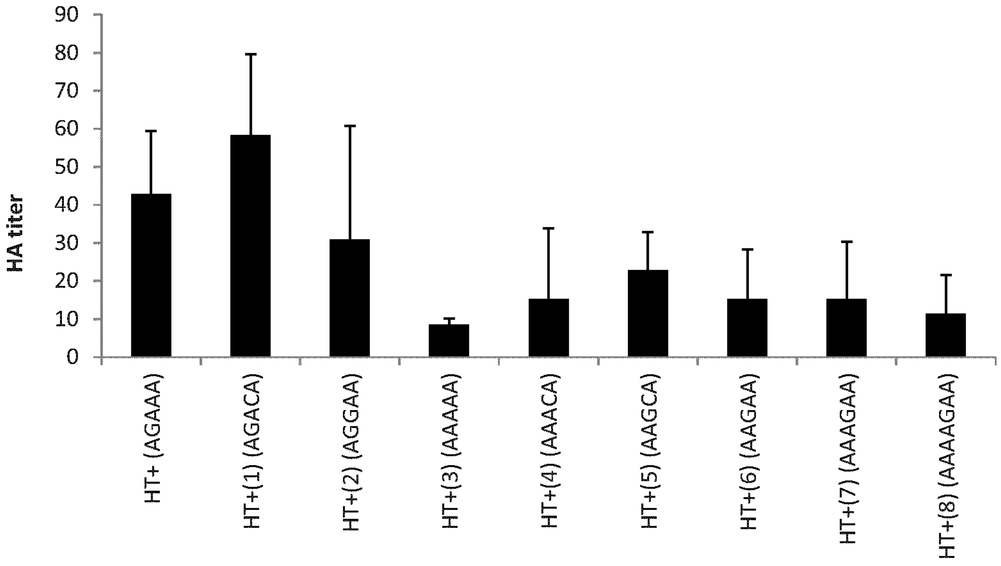
FIG. 4B shows HA titers of a nucleotide sequence of interest produced in plants comprising CPMV HT+ expression construct and a variant plant Kozak sequence as indicated.

The plant kozak sequence of CPMV HT+ as described herein, may be any plant kozak sequence, including but not limited, one of the sequences of SEQ ID NO's:5-17 (also see FIG. 4, CPMV HT+ with plant kozak; the constructs of FIG. 4 includes nucleotides 1-528 of SEQ ID NO:1, one of several examples of a plant kozak sequence, and includes a plant regulatory region and the transcription initiation site ATG of a nucleotide sequence of interest: GOI).

The expression enhancer may further comprise one or more "kozak consensus sequence" or "kozak sequence". The kozak sequence may include any kozak sequence that is active in a plant, for example, a plant kozak sequence (e.g. CPMV HT+; CPMV HT WT115), or a kozak sequence present within the native M protein (e.g. CPMV HT+511). Kozak sequences play a major role in the initiation of translation. The rate of translation can be optimized by ensuring that any mRNA instability sequences are eliminated from the transgene construct, and as required, that the translational start site or initiation site matches the kozak consensus for plants (Gutierrez, R.A. et al., 1999, Trends Plant Sci. 4, 429-438; Kawaguchi, R. and Bailey-Serres, J., 2002, Curr. Opin. Plant Biol. 5, 460-465). The most highly conserved position in this motif is the purine (which is most often an A) three nucleotides upstream of the ATG codon, which indicates the start of translation (Kozak, M., 1987, J. Mol. Biol. 20:947-950, herein incorporated by reference). The kozak sequence may include a native sequence present within the incomplete M protein. For example, the sequence immediately upstream from nucleotide 512 of the incomplete M protein as shown in SEQ ID NO's:55 or 56, for example nucleotides 508-511 of SEQ ID NO:55.

Plant kozak consensus sequences are known in the art (see for example Rangan et al. Mol. Biotechnol., 2008, July 39(3), pp. 207-213). Both naturally occurring and synthetic Kozak sequences may be used in the expression enhancer or may be fused to the nucleotide sequence of interest as described herein.

The plant kozak sequence may be any known plant kozak sequences (see for example L. Rangan et. al. Mol. Biotechnol.2008), including, but not limited to the following plant consensus sequences:

```
(caA(A/C)a plant kingdom)

(aaA(A/C)a dicots)

(aa(A/G)(A/C)a arabidopsis)
```

The plant kozak sequence may also be selected from the group of (see FIG. 4):

```
AGAAA

AGACA

AGGAA

AAAAA

AAACA
```

-continued

```
AAGCA

AAGAA

AAAGAA

AAAGAA

(A/-)A(A/G)(A/G)(A/C)A. Consensus sequence)
```

CPMV HT+ with a plant kozak consensus sequence is provided in SEQ ID NO:4 (nucleotide 1-160, 5'UTR, including modified ATG at positions 115 (GTG) lower case bold and italics; stuffer fragment comprising: an incomplete M protein underlined, nucleotides 161-509, with modified nucleotide at 162 (ACG); a multiple cloning site, italics, nucleotides 510-528; and a consensus plant kozak sequence, caps and bold, nucleotides 529-534).

```
                                                        (SEQ ID NO: 4)
  1 tattaaaatc ttaataggtt ttgataaaag cgaacgtggg gaaacccgaa ccaaaccttc

 61 ttctaaactc tctctcatct ctcttaaagc aaacttctct cttgtctttc ttgcgtgagc

121 gatcttcaac gttgtcagat cgtgcttcgg caccagtaca acgttttctt tcactgaagc

181 gaaatcaaag atctctttgt ggacacgtag tgcggcgcca ttaaataacg tgtacttgtc

241 ctattcttgt cggtgtggtc ttgggaaaag aaagcttgct ggaggctgct gttcagcccc

301 atacattact tgttacgatt ctgctgactt tcggcgggtg caatatctct acttctgctt

361 gacgaggtat tgttgcctgt acttctttct tcttcttctt gctgattggt tctataagaa

421 atctagtatt ttctttgaaa cagagttttc ccgtggtttt cgaacttgga gaaagattgt

481 taagcttctg tatattctgc ccaaatttgt tcgggcccaa taccgcgg(A/-)A(A/G)
    (A/G)(A/C)A
```

SEQ ID NO:56 ("CPMV HT+ [511]") comprises a segment of the native sequence of the CPMV RNA 2 genome from nucleotides 1-154. The 5'UTR sequence from nucleotides 1-511 of SEQ ID NO:56 comprises modified "atg" sequences at positions 115 ("g" in place of "a"; italics bold) and 162 ("c" in place of "t"; italics bold), and an incomplete M protein (underlined) from nucleotides 161-511. CPMV HT+ [511] comprises a native M protein kozak consensus sequence (nucleotides 508-511; bold):

```
                                                        SEQ ID NO: 56
  1 tattaaaatc ttaataggtt ttgataaaag cgaacgtggg gaaacccgaa ccaaaccttc

 61 ttctaaactc tctctcatct ctcttaaagc aaacttctct cttgtctttc ttgcgtgagc

121 gatcttcaac gttgtcagat cgtgcttcgg caccagtaca acgttttctt tcactgaagc

181 gaaatcaaag atctctttgt ggacacgtag tgcggcgcca ttaaataacg tgtacttgtc

241 ctattcttgt cggtgtggtc ttgggaaaag aaagcttgct ggaggctgct gttcagcccc

301 atacattact tgttacgatt ctgctgactt tcggcgggtg caatatctct acttctgctt

361 gacgaggtat tgttgcctgt acttctttct tcttcttctt gctgattggt tctataagaa

421 atctagtatt ttctttgaaa cagagttttc ccgtggtttt cgaacttgga gaaagattgt

481 taagcttctg tatattctgc ccaaatttga a...
```

Constructs 1952-1959 are examples of CPMV HT+ expression enhancers comprising SEQ ID NO:1 with variant plant kozak sequences (see Example 3, and FIGS. 4 and 7).

Another non-limiting example of a CPMV HT+ enhancer sequence is provided by the sequence of SEQ ID NO:3 (CPMV HT+[WT115]). Expression cassettes or vectors comprising CPMV HT+ and including a plant regulatory region in operative association with the expression enhancer sequence of SEQ ID NO:3, and the transcriptional start site (ATG) at the 3' end fused to a nucleotide sequence of interest (GOI) are also part of the present invention.

SEQ ID NO: 3 (CPMV HT+[WT115]) comprises nucleotides 1-160, 5'UTR, with an ATG at position 115-117, lower case bold, a stuffer fragment comprising: an incomplete M protein underlined, nucleotides 161-509, with a modified ATG at position 161-163 (acg) lower case bold, and underlined, a multiple cloning site, italics, nucleotides 510-528; and a plant kozak sequence, caps and bold, nucleotides 529-534.

```
                                                         (SEQ ID NO: 3)
  1tattaaaatc ttaataggtt ttgataaaag cgaacgtggg gaaacccgaa ccaaaccttc

 61ttctaaactc tctctcatct ctcttaaagc aaacttctct cttgtctttc ttgcatgagc

121gatcttcaac gttgtcagat cgtgcttcgg caccagtaca acgttttctt tcactgaagc

181gaaatcaaag atctctttgt ggacacgtag tgcggcgcca ttaaataacg tgtacttgtc

241ctattcttgt cggtgtggtc ttgggaaaag aaagcttgct ggaggctgct gttcagcccc

301atacattact tgttacgatt ctgctgactt tcggcgggtg caatatctct acttctgctt

361gacgaggtat tgttgcctgt acttctttct tcttcttctt gctgattggt tctataagaa

421atctagtatt ttctttgaaa cagagttttc ccgtggtttt cgaacttgga gaaagattgt

481taagcttctg tatattctgc ccaaatttgt tcgggcccaa taccgcggAG AAAA
```

The plant kozak sequence of SEQ ID NO:3 may be any plant kozak sequence, including but not limited, one of the sequences of SEQ ID NO's:5-17 (also see FIG. 4, CPMV HT+ with plant kozak; the constructs of FIG. 4 includes nucleotides 1-528 of SEQ ID NO:1, one of several examples of a plant kozak sequence, and includes a plant regulatory region and the transcription initiation site ATG of a nucleotide sequence of interest: GOI).

The CPMV HT+ expression enhancer may have at least 100%, 99%, 98%, 97%, 96%, 95%, 90%, 85%, and 80% identity to the sequence defined by nucleotides 1-160 of SEQ ID NO's: 1, 3 or 4, nucleotides 161-509 of SEQ ID NO's: 1, 3 or 4, or nucleotides 1-509 of SEQ ID NO's: 1, 3 or 4. For example the enhancer sequence may have from about 80% to about 100%, or any amount therebetween, identity to the sequence defined by nucleotides 1-160 of SEQ ID NO's: 1, 3 or 4, nucleotides 161-509 of SEQ ID NO's: 1, 3 or 4, or nucleotides 1-509 of SEQ ID NO's: 1, 3 or 4, or from about 90% to about 100%, or any amount therebetween, identity to the sequence defined by nucleotides 1-160 of SEQ ID NO's: 1, 3 or 4, nucleotides 161-509 of SEQ ID NO's: 1, 3 or 4, or nucleotides 1-509 of SEQ ID NO's: 1, 3 or 4, or about 95% to about 100%, or any amount therebetween, identity to the sequence defined by nucleotides 1-160 of SEQ ID NO's: 1, 3 or 4, nucleotides 161-509 of SEQ ID NO's: 1, 3 or 4, or nucleotides 1-509 of SEQ ID NO's: 1, 3 or 4, or any amount therebetween, wherein the expression enhancer, when operatively linked to a plant regulatory region and a plant kozak sequence as described herein, increases the level of expression of a nucleotide sequence of interest that is operatively linked to the expression enhancer when compared to the level of expression of the nucleotide sequence of interest fused to CPMV HT (SEQ ID NO:2) using the same plant regulatory region.

The terms "percent similarity", or "percent identity" when referring to a particular sequence are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Nat'l. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

Figure 3:
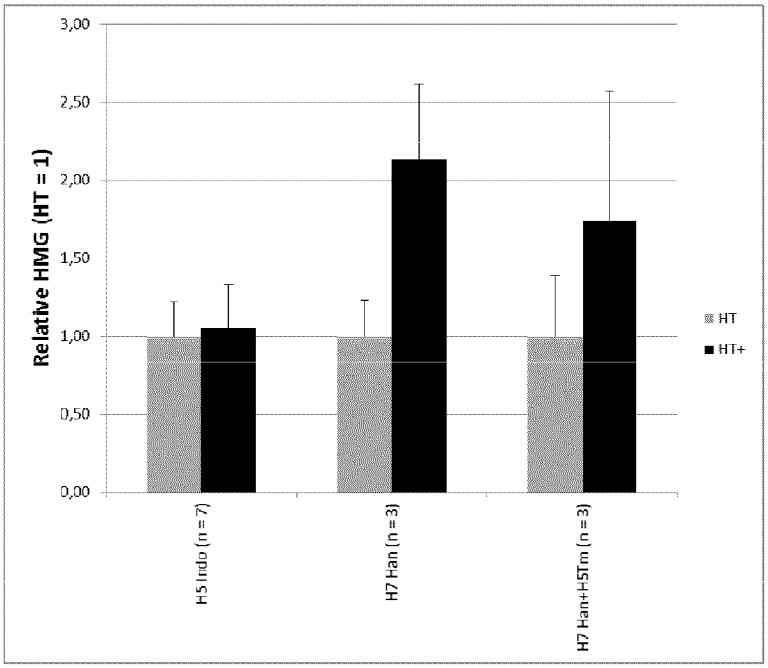
FIG. 3 shows the relative hemagglutination titres (HMG) in crude protein extracts of proteins produced in plants comprising CPMV-HT (prior art) expression constructs, and CPMV HT+ based expression constructs. Data for the expression of H5 from Influenza A/Indonesia/5/2005 with a PDI signal peptide (H5 Indo; construct number 409: CPMV HT; and construct number 2319: CPMV HT+; see Example 5), H7 from Influenza A/Hangzhou/1/2013 with a alfalfa protein disulfide isomerase (H7 Han; construct number 2140: CPMV HT; and construct number 2142: CPMV HT+; see example 6), H7 from Influenza A/Hangzhou/1/2013 fused to the transmembrane domain and cytoplasmic tail (TMCT) of H5 from influenza A/Indonesia/5/2005 and with the signal peptide of alfalfa protein disulfide isomerase (H7Han+H5Tm; construct number 2130: CPMV HT; construct number 2146: CPMV HT+; see example 7) are shown.

As shown in FIGS. 2-4, the use of the expression enhancers as described herein generally resulted in an increase of expression of the nucleotide sequence of interest, when compared to the expression of the same nucleotide sequence of interest using the same promoter, 3'UTR and terminator sequences, and operatively linked to a prior art expression enhancer. For example, with reference to FIGS. 2 and 3, there is shown a comparison of expression of proteins produced in plants comprising CPMV-HT (prior art) expression constructs and CPMV HT+ based expression constructs, operatively linked with:

H1 A/California/07/2009 ("PDI-H1 Cal", or "H1 A/California/07/2009"): CPMV HT+ based construct number 1805, CPMV HT based construct number 484 (see Example 4);

H3 A/Victoria/361/2011 ("PDI-H3 Vic", or "H3 A/Victoria/361/2011"): CPMV HT+ based construct number 1819; CPMV HT based construct number 1391 (see Examples 1 and 2, respectively);

B/Wisconsin/1/2010 with deleted proteolytic loop and with a native signal peptide ("WtSp-B Wis-PrL", or "B/Wisconsin/1/2010"): CPMV HT+ based construct number 1839; CPMV HT based construct number 1445 (see Example 12);

B Brisbane/60/08 with deleted proteolytic loop and with a PDI signal peptide ("B Brisbane/60/08"): CPMV HT+ based construct number 1829; CPMV HT based construct number 1039 (see Example 8);

B Brisbane/60/08+H1Tm, with deleted proteolytic loop fused to the transmembrane domain and cytoplasmic tail and with a PDI signal peptide ("B Brisbane/60/08+H1Tm"): CPMV HT+ based construct number 1875; CPMV HT based construct 1067 (see Example 9), B Massachusetts/2/2012 2012 with deleted proteolytic loop and with a PDI signal peptide ("B Massachusetts/2/2012 2012"): CPMV HT+ based construct number 2052; CPMV HT based construct number 2072 (see Example 10), B Massachusetts/2/2012+H1Tm with deleted proteolytic loop fused to the transmembrane domain and cytoplasmic tail and with a PDI signal peptide ("B Massachusetts/2/2012+H1Tm"): CPMV HT+ based construct number 2062; CPMV HT based construct 2074 (see Example 11), B Wisconsin/1/2010+H1Tm with deleted proteolytic loop fused to the transmembrane domain and cytoplasmic tail and with the native signal peptide ("B Wisconsin/1/2010+H1Tm"): CPMV HT+ based construct number 1860; CPMV HT based construct 1454 (see Example 13);

H5 from Influenza A/Indonesia/5/2005 (PDI H5 Indo) with a PDI signal peptide: CPMV HT+ based construct number 2319; CPMV HT based construct number 409 (see Example 5);

H7 from Influenza A/Hangzhou/1/2013 in which the native signal peptide has been replaced by that of alfalfa protein disulfide isomerase (H7 Han): CPMV HT+ based construct no 2142; CPMV HT based construct number 2140 (see Example 6)

H7 from Influenza A/Hangzhou/1/2013 fused to the transmembrane domain and cytoplasmic tail (TMCT) of H5 from influenza A/Indonesia/5/2005 and with the signal peptide of alfalfa protein disulfide isomerise (H7 Han+H5Tm): CPMV HT+ based construct number 2146; CPMV HT based construct number 2130 (see Example 7).

In general, the expression (determined as hemagglutination activity) is increased in the CPMV HT+ based construct when compared to that for the prior art CPMV HT based construct.

Furthermore, several of the nucleotide sequences of interest encoded chimeric or modified proteins, for example comprising heterologous signal peptides (e.g. PDI), heterologous transmembrane domain cytoplasmic tail sequences (TDCT), and/or modified sequences including a deleted proteolytic loop (PrL-), and an increase in activity was still observed.

The increase in expression observed using CPMV HT+ based constructs is also observed if the plant kozak sequence used in the CPMV HT+ based constructs above is replaced with other plant kozak sequences for example, one of those plant kozak sequences defined in SEQ ID NO:8-16. For example, with reference to FIG. 4, there is shown a comparison of the expression of proteins produced in plants comprising CPMV HT+ based expression constructs, operatively linked with a nucleotide sequence of interest (H3 A/Victoria/361) each fused to various plant kozak sequences. In each case, the expression (determined as hemagglutination titre) the CPMV HT+ based construct demonstrates significant expression levels and greater than the prior art CPMV HT based construct.

A nucleotide sequence interest that encodes a protein requires the presence of a "translation initiation site" or "initiation site" or "translation start site" or "start site" or "start codon" located upstream of the gene to be expressed. Such initiation sites may be provided either as part of an enhancer sequence or as part of a nucleotide sequence encoding the protein of interest.

"Expression cassette" refers to a nucleotide sequence comprising a nucleic acid of interest under the control of, and operably (or operatively) linked to, an appropriate promoter or other regulatory elements for transcription of the nucleic acid of interest in a host cell.

By "proteolytic loop" or "cleavage site" is meant the consensus sequence of the proteolytic site that is involved in precursor HA0 cleavage. "Consensus" or "consensus sequence" as used herein means a sequence (either amino acid or nucleotide sequence) that comprises the sequence variability of related sequences based on analysis of alignment of multiple sequences, for example, subtypes of a particular influenza HA0 sequence. Consensus sequence of the influenza HA0 cleavage site may include influenza A consensus hemagglutinin amino acid sequences, including for example consensus H1, consensus H3, consensus H5, or influenza B consensus hemagglutinin amino acid sequences, for example but not limited to B Florida, B Malaysia, B Wisconsin and B Massachusetts. Non limiting examples of sequences of the proteoloytic loop region are shown in FIGS. 15 and 18B of U.S. provisional application No. 61/806,227 (filed Mar. 28, 2013, which is incorporated herein by reference; also see Bianchi et al., 2005, Journal of Virology, 79:7380-7388; incorporated herein by reference).

Residues in the proteolytic loop or cleavage site might be either mutated, for example but not limited to point mutation, substitution, insertion, or deletion. The term "amino acid mutation" or "amino acid modification" as used herein is meant to encompass amino acid substitutions, deletions, insertions, and modifications. Any combination of substitution, deletion, insertion, and modification can be made as described in U.S. provisional application No. 61/806,227 (filed Mar. 28, 2013, which is incorporated herein by reference) to arrive at the final construct, provided that the final construct possesses the desired characteristics, e.g., reduced or abolished cleavage of the proteolytic loop or cleavage site by a protease.

As described herein, there is provided a nucleic acid construct (expression system) comprising an expression enhancer sequence operatively linked to a nucleotide sequence of interest encoding a protein of interest. Also provided are plant expression systems comprising an enhancer sequence as described herein. Also provided is a plant expression system comprising a plant regulatory region, in operative association with an enhancer sequence that is operatively linked to a nucleotide sequence of interest, the nucleotide sequence of interest encoding a protein of interest. The enhancer sequence may be selected from SEQ ID NO's:1 or 3 or a nucleotide sequence that exhibits 100%, 99%, 98%, 97%, 96%, 95%, 90%, 85% or 80% identity to nucleotides 1-160 of SEQ ID NO's: 1, 3 or 4, nucleotides 161-509 of SEQ ID NO's: 1, 3 or 4, or nucleotides 1-509 of SEQ ID NO's: 1, 3 or 4, wherein the expression enhancer, when operatively linked to a plant regulatory region and a plant kozak sequence as described herein, increases the level of expression of a nucleotide sequence of interest that is operatively linked to the expression enhancer when compared to the level of expression of the nucleotide sequence of interest fused to the CPMV HT (SEQ ID NO:2; prior art enhancer sequence comprising an incomplete M protein as described in Sainsbury F., and Lomonossoff G. P., 2008, Plant Physiol. 148: pp. 1212-1218; which is incorporated herein by reference) using the same plant regulatory region.

The enhancer sequence of the present invention may be used to express a protein of interest in a host organism for example a plant. In this case, the protein of interest may also be heterologous to the host organism in question and introduced into the plant cells using transformation techniques know in the art. A heterologous gene in an organism may replace an endogenous equivalent gene, i.e. one which normally performs the same or a similar function, or the inserted sequence may be additional to the endogenous gene or other sequence.

The invention further provides an expression cassette comprising in series, a promoter or plant regulatory region, operatively linked to an expression enhancer sequence as described herein which is fused with a nucleotide sequence of interest and a 3'UTR sequence and a terminator sequence. The enhancer sequence may be defined by, for example, but not limited to, any one of SEQ ID NO's:1, 3 and 4 or a nucleotide sequence that exhibits 100%, 99%, 98%, 97%, 96%, 95%, 90%, 85% or 80% identity to nucleotides 1-160 of SEQ ID NO's: 1, 3 or 4, nucleotides 161-509 of SEQ ID NO's: 1, 3 or 4, or nucleotides 1-509 of SEQ ID NO's: 1, 3 or 4. Either the expression enhancer or the nucleotide sequence of interest may comprise a plant kozak sequence.

As one of skill in the art would appreciate, the termination (terminator) sequence may be any sequence that is active the plant host, for example the termination sequence may be derived from the RNA-2 genome segment of a bipartite RNA virus, e.g. a comovirus, or the termination sequence may be a NOS terminator.

The constructs of the present invention can further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962,028; which is incorporated herein by reference), the promoter used in regulating plastocyanin expression (Pwee and Gray 1993; which is incorporated herein by reference). The termination (terminator) sequence may be obtained from the 3'UTR of the alfalfa plastocyanin gene.

By "nucleotide (or nucleic acid) sequence of interest", or "coding region of interest", it is meant any nucleotide sequence, or coding region (these terms may be used interchangeably) that is to be expressed within a host organism, for example a plant, to produce a protein of interest. Such a nucleotide sequence of interest may encode, but is not limited to, native or modified proteins, an industrial enzyme or a modified industrial enzyme, an agricultural protein or a modified agricultural protein, a helper protein, a protein supplement, a pharmaceutically active protein, a nutraceutical, a value-added product, or a fragment thereof for feed, food, or both feed and food use.

The protein of interest may comprise a native, or a non-native signal peptide; the non-native signal peptide may be of plant origin or obtained from an animal or bacterial polypeptide. The native signal peptide may correspond to that of the protein of interest being expressed, additionally, the signal peptide may be from a structural protein or hemagglutinin of a virus other than influenza. Non-limiting examples of a signal peptide that may be used is that of alfalfa protein disulfide isomerase (PDI SP; nucleotides 32-103 of Accession No. Z11499), or the patatin signal peptide (PatA SP; located nucleotides 1738-1806 of GenBank Accession number A08215). The nucleotide sequence of PatA SP for this accession number is:

```
                                          (SEQ ID NO: 57)
ATGGCAACTACTAAAACTTTTTTAATTTTATTTTTTATGATATTAGCAAC

TACTAGTTCAACATGTGCT;
```

the amino acid sequence of patatin A signal peptide is:

```
                                          (SEQ ID NO: 58)
          MATTKTFLILFFMILATTSSTCA
```

The nucleotide sequence of interest, or coding region of interest may also include a nucleotide sequence that encodes a pharmaceutically active protein, for example growth factors, growth regulators, antibodies, antigens, and fragments thereof, or their derivatives useful for immunization or vaccination and the like. Such proteins include, but are not limited to a protein that is a human pathogen, a viral protein, for example but not limited to one or more proteins from Respiratory syncytial virus (RSV), Rotavirus, influenza virus, human immunodeficiency virus (HIV), Rabies virus, human papiloma virus (HPV), Enterovirus 71 (EV71), or interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gamma, blood clotting factors, for example, Factor VIII, Factor IX, or tPA hGH, receptors, receptor agonists, antibodies for example but not limited to Rittman, neuropolypeptides, insulin, vaccines, growth factors for example but not limited to epidermal growth factor, keratinocyte growth factor, transformation growth factor, growth regulators, antigens, autoantigens, fragments thereof, or combinations thereof.

The protein of interest may also include an influenza hemagglutinin (HA; see WO 2009/009876, which is incorporated herein by reference). HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available (see, for example, the BioDefense and Public Health Database (Influenza Research Database; Squires et al., 2008 Nucleic Acids Research 36:D497-D503) at URL: biohealthbase.org/GSearch/ home.do?decorator=Influenza; or the databases maintained by the National Center for Biotechnology Information (see URL: ncbi.nlm.nih.gov), both of which are incorporated herein by reference).

An HA protein may be of a type A influenza, a type B influenza, or is a subtype of type A influenza HA selected from the group of H1, H2, H3, H4, H5, H6, H7, H8, H9, H10, H11, H12, H13, H14, H15, and H16. In some aspects of the invention, the HA may be from a type A influenza, selected from the group H1, H2, H3, H5, H6, H7 and H9. Fragments of the HAs listed above may also be considered a protein of interest. Furthermore, domains from an HA type or subtype listed above may be combined to produce chimeric HA's (see for example WO2009/076778 which is incorporated herein by reference).

Examples of subtypes comprising HA proteins include A/New Caledonia/20/99 (H1N1), A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949(H10N7), A/duck/England/56(H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

The HA protein may be an H1, H2, H3, H5, H6, H7 or H9 subtype. For example, the H1 protein may be from the A/New Caledonia/20/99 (H1N1), A/PuertoRico/8/34 (H1N1), A/Brisbane/59/2007 (H1N1), A/Solomon Islands 3/2006 (H1N1), A/California/04/2009 (H1N1) or A/California/07/2009 (H1N1) strain. The H3 protein may also be from the A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), or A/Perth/16/2009 (H3N2) strain. In a further aspect of the invention, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In an aspect of the invention, the H6 protein may be from the A/Teal/HongKong/W312/97 (H6N1) strain. The H7 protein may be from the A/Equine/Prague/56 (H7N7) strain, or H7 A/Hangzhou/1/2013, A/Anhui/1/2013 (H7N9), or A/Shanghai/2/2013 (H7N9) strain. In an aspect of the invention, the H9 protein is from the A/HongKong/1073/99 (H9N2) strain. In a further aspect of the invention, the HA protein may be from an influenza virus may be a type B virus, including B/Malaysia/2506/2004, B/Florida/4/2006, B/Brisbane/60/08, B/Massachusetts/2/2012-like virus (Yamagata lineage), or B/Wisconsin/1/2010 (Yamagata lineage). Non-limiting examples of amino acid sequences of the HA proteins from H1, H2, H3, H5, H6, H7, H9 or B subtypes include sequences as described in WO 2009/009876, WO 2009/076778, WO 2010/003225 (which are incorporated herein by reference). The influenza virus HA protein may be H5 Indonesia.

The HA may also be a chimeric HA, wherein a native transmembrane domain of the HA is replaced with a heterologous transmembrane domain. The transmembrane domain of HA proteins is highly conserved (see for example FIG. 1C of WO 2010/148511; which is incorporated herein by reference). The heterologous transmembrane domain may be obtained from any HA transmembrane domain, for example but not limited to the transmembrane domain from H1 California, B/Florida/4/2006 (GenBank Accession No. ACA33493.1), B/Malaysia/2506/2004 (GenBank Accession No. ABU99194.1), H1/Bri (GenBank Accession No. ADE28750.1), H1 A/Solomon Islands/3/2006 (GenBank Accession No. ABU99109.1), H1/NC (GenBank Accession No. AAP34324.1), H2 A/Singapore/1/1957 (GenBank Accession No. AAA64366.1), H3 A/Brisbane/10/2007 (GenBank Accession No. ACI26318.1), H3 A/Wisconsin/67/2005 (GenBank Accession No. ABO37599.1), H5 A/Anhui/1/2005 (GenBank Accession No. ABD28180.1), H5 A/Vietnam/1194/2004 (GenBank Accession No. ACR48874.1), H5-Indo (GenBank Accession No. ABW06108.1). The transmembrane domain may also be defined by the following consensus amino acid sequence:

```
(SEQ ID NO: 59)
iLXiYystvAiSslXlXXmlagXsXwmcs
```

Examples of constructs comprising a chimeric HA with a heterologous trans-membrane domain include: construct number 1875 (B Brisbane/60/08+H1TM, with trans-membrane domain and cytoplasmic tail replaced by H1 A/California/07/2009; see example 9), construct number 2074 (B Massachusetts/2/2012+H1Tm, with trans-membrane domain and cytoplasmic tail replaced by those of H1 A/California/07/2009; see Example 11), and construct number 1860 (B Wisconsin/1/2010+H1Tm with trans-membrane domain and cytoplasmic tail replaced by those of H1 A/California/07/2009; see Example 13). Activity of these chimeric HA's is shown in FIG. 2.

The expression enhancer as defined herein may also be used to drive expression of any nucleotide sequence of interest that encodes one or more than one protein of interest. Examples of a protein, include, for example but not limited to, an industrial enzyme for example, cellulase, xylanase, protease, peroxidase, subtilisin, a protein supplement, a nutraceutical, a value-added product, or a fragment thereof for feed, food, or both feed and food use, a pharmaceutically active protein, for example but not limited to growth factors, growth regulators, antibodies, antigens, and fragments thereof, or their derivatives useful for immunization or vaccination and the like. Additional proteins of interest may include, but are not limited to, interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gamma, blood clotting factors, for example, Factor VIII, Factor IX, or tPA hGH, receptors, receptor agonists, antibodies, neuropolypeptides, insulin, vaccines, growth factors for example but not limited to epidermal growth factor, keratinocyte growth factor, transformation growth factor, growth regulators, antigens, autoantigens, fragments thereof, an antibody, a monoclonal antibody, a chimeric monoclonal antibody, a single chain monoclonal antibody, a virus like particle (VLP), or combinations thereof, If the protein of interest is a VLP, then the VLP may comprise an HA0 precursor form, or the HA' or HA2 domains retained together by disulphide bridges form. A VLP may have an average size of about 20 nm to 1 μm, or any amount therebetween, for example 60, 65, 70, 75, 80, 85, 90, 95, 100, 105, 110, 120, 130, 140, 150 160, 170, 180, 190, or 200 nm, or any amount therebetween, for example 100 nm, and may include a lipid membrane. The VLP may be enveloped, or non-enveloped, for example, a viral envelope protein, a viral structural protein, a viral capsid protein, or a viral coat protein. The VLP may further comprise one or more lipids, phospholipids, nucleic acids, membranes or the like.

The HA may comprise a native, or a non-native signal peptide; the non-native signal peptide may be of plant origin. For example, the signal peptide may be a protein disulfide isomerase signal peptide (PDI). The native signal peptide may correspond to that of the hemagglutinin being expressed, or may correspond to a second hemagglutinin.

The present invention also provides nucleic acid molecules comprising sequences encoding an HA protein. The nucleic acid molecules may further comprise one or more regulatory regions operatively linked to the sequence encoding an HA protein. The nucleic acid molecules may comprise a sequence encoding an H1, H2, H3, H4, H5, H6, H7, H8, H9, H10, H11, H12, H13, H14, H15, H16 or HA from type B influenza. For example, the HA protein encoded by the nucleic acid molecule may be an H1, H2, H3, H5, H6, H7, H9 subtype an HA from type B. The H1 protein encoded by the nucleic acid may be from the A/New Caledonia/20/99 (H1N1), A/PuertoRico/8/34 (H1N1), A/Brisbane/59/2007 (H1N1), A/Solomon Islands 3/2006 (H1N1), A/California/04/2009 (H1N1) or A/California/07/2009 (H1N1) strain. The H3 protein encoded by the nucleic acid molecule may be from the A/Brisbane 10/2007 (H3N2), A/Wisconsin/67/2005 (H3N2), A/Victoria/361/2011 (H3N2), A/Texas/50/2012 (H3N2), A/Hawaii/22/2012 (H3N2), A/New York/39/2012 (H3N2), or A/Perth/16/2009 (H3N2) strain. The H2 protein encoded by the nucleic acid molecule may be from the A/Singapore/1/57 (H2N2) strain. The H5 protein encoded by the nucleic acid molecule A/Anhui/1/2005 (H5N1), A/Vietnam/1194/2004 (H5N1), or A/Indonesia/5/2005 strain. The H6 protein encoded by the nucleic acid molecule may be from the A/Teal/HongKong/W312/97 (H6N1) strain. The H7 protein encoded by the nucleic acid molecule may be from the A/Equine/Prague/56 (H7N7) strain, or H7 A/Hangzhou/1/2013, A/Anhui/1/2013 (H7N9), or A/Shanghai/2/2013 (H7N9) strain. Additional, the H9 protein encoded by the nucleic acid molecule may be from the A/HongKong/1073/99 (H9N2) strain. The HA protein encoded by the nucleic acid molecule may be from an influenza virus type B virus, including B/Malaysia/2506/2004, B/Florida/4/2006, B/Brisbane/60/08, B/Massachusetts/2/2012-like virus (Yamagata lineage), or B/Wisconsin/1/2010 (Yamagata lineage). Non-limiting examples of amino acid sequences of the HA proteins from H1, H2, H3, H5, H6, H7, H9 or B subtypes include sequences as described in WO 2009/009876, WO 2009/076778, WO 2010/003225 (which are incorporated herein by reference). The influenza virus HA protein may be H5 Indonesia.

TABLE 1

Examples of constructs that have been prepared as described herein:

| Construct # | SP[1] | Sequence of Interest | Example |
|---|---|---|---|
| CPMV-HT based constructs (constructs comprising SEQ ID NO: 2; prior art) | | | |
| 1391 | PDI[2] | H3 Victoria | 1 |
| 484 | PDI | H1 California | 4 |
| 409 | PDI | H5 Indonesia | 5 |
| 2140 | PDI | H7 Hangzhou | 6 |
| 2130 | PDI | H7 Hangzhou+H5 Indonesia TMCT[4] | 7 |
| 1039 | PDI | B Brisbane(Prl−) | 8 |
| 1067 | PDI | B Brisbane(PrL−)+Hi California TMCT | 9 |
| 2072 | PDI | B Massachusetts (PrL−) | 10 |
| 2074 | PDI | B Massachusetts (PrL−)+H1 California TMCT | 11 |
| 1445 | WT[3] | B Wisconsin (PrL−) | 12 |
| 1454 | WT | B Wisconsin (PrL−)+H1 California TMCT | 13 |
| CPMV HT+ based constructs (constructs comprising SEQ ID NO: 1) | | | |
| 1819 | PDI | H3 Victoria | 2 |
| 1805 | PDI | H1 California | 4 |
| 2319 | WT | H5 Indonesia | 5 |
| 2142 | PDI | H7 Hangzhou | 6 |
| 2146 | PDI | H7 Hangzhou+H5 Indonesia TMCT | 7 |
| 1829 | PDI | B Brisbane(Prl−) | 8 |
| 1875 | PDI | B Brisbane(PrL−)+Hi California TMCT | 9 |
| 2052 | PDI | B Massachusetts (PrL−) | 10 |
| 2062 | PDI | B Massachusetts (PrL−)+H1 California TMCT | 11 |
| 1839 | WT | B Wisconsin (PrL−) | 12 |
| 1860 | WT | B Wisconsin (PrL−)+H1 California TMCT | 13 |

[1]SP—signal peptide
[2]PDI—alfalfa protein disulfide isomerise
[3]WT—wild type or native
[4]TMCT—transmembrane domain and cytoplasmic tail If the nucleic acid sequence of interest encodes a product that is directly or indirectly toxic to the plant, then such toxicity may be reduced by selectively expressing the nucleotide sequence of interest within a desired tissue or at a desired stage of plant development.

The coding region of interest or the nucleotide sequence of interest may be expressed in any suitable plant host which is either transformed or comprises the nucleotide sequences, or nucleic acid molecules, or genetic constructs, or vectors of the present invention. Examples of suitable hosts include, but are not limited to, *Arabidopsis*, agricultural crops including for example canola, *Brassica* spp., maize, *Nicotiana* spp., (tobacco) for example, *Nicotiana benthamiana*, alfalfa, potato, sweet potato (*Ipomoea batatus*), *ginseng*, pea, oat, rice, soybean, wheat, barley, sunflower, cotton, corn, rye (*Secale cereale*), sorghum (*Sorghum bicolor, Sorghum vulgare*), safflower (*Carthamus tinctorius*).

The terms "biomass" and "plant matter" as used herein refer to any material derived from a plant. Biomass or plant matter may comprise an entire plant, or part of plant including the leaf, root, stem, flower, seed, it may also include any tissue of the plant, any cells of the plant, or any fraction of the plant, part or the plant, tissue or cell. Further, biomass or plant matter may comprise intracellular plant components, extracellular plant components, liquid or solid extracts of plants, or a combination thereof. Further, biomass or plant matter may comprise plants, plant cells, tissue, a liquid extract, or a combination thereof, from plant leaves, stems, fruit, roots or a combination thereof. A portion of a plant may comprise plant matter or biomass.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DRS (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812), the rice actin 1 (Zhang et al, 1991, Plant Cell, 3: 1155-1165), actin 2 (An et al., 1996, *Plant J.,* 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004). the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

As described herein, regulatory regions comprising enhancer sequences with demonstrated efficiency in leaf expression, have been found to be effective in transient expression. Without wishing to be bound by theory, attachment of upstream regulatory elements of a photosynthetic gene by attachment to the nuclear matrix may mediate strong expression. For example up to −784 from the translation start site of pea plastocyanin (U.S. Pat. No. 7,125,978, which is incorporated herein by reference) may be used mediate strong reporter gene expression.

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described above may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

If desired, the constructs of this invention may be further manipulated to include selectable markers. However, this may not be required. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

A vector may also include an expression enhancer as described herein. The expression enhancer may be positioned on a T-DNA which also contains a suppressor of gene silencing and NPTII. The polylinker may also encode one or two sets of 6× Histidine residues to allow the inclusion of N- or C-terminal His-tags to the protein of interest to facilitate protein purification.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998, *EMBO J.* 17, 6739-6746, which is incorporated herein by reference). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV -p21, p19 of Tomato bushy stunt virus (TBSV p19; the construction of p19 is described in described in WO 2010/0003225, which is incorporated herein by reference), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of *Heracleum* latent virus (HLV-p10), or p16 of Garlic common latent virus (GCLV-p16).

Therefore, one or more suppressors of silencing, for example, but not limited to, HcPro, TEV-p1/HC-Pro, BYV-p21, TBSV p19, TCV-CP, CMV-2b, PVX-p25, rgscam, B2 protein from FHV, the small coat protein of CPMV, and coat protein from TCV, PVM-p11, PVS-p11, BScV-p16, CTV-p23, GLRaV-2 p24, GBV-p14, HLV-p10, GCLV-p16, or GVA-p10 may be co-expressed along with the comovirus-based expression cassette, geminivirus-derived amplification element, and the nucleic acid sequence encoding the protein of interest to further ensure high levels of protein production within a plant.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991*, Gene* 100: 247-250), Scheid et al. (1991*, Mol. Gen. Genet.* 228: 104-112), Guerche et al. (1987*, Plant Science* 52: 111-116), Neuhause et al. (1987*, Theor. Appl Genet.* 75: 30-36), Klein et al., (2987*, Nature* 327: 70-73); Freeman et al. (1984*, Plant Cell Physiol.* 29: 1353), Howell et al. (1980*, Science* 208: 1265), Horsch et al. (1985*, Science* 227: 1229-1231), DeBlock et al., (1989*, Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002*, J Virol Meth,* 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009, *Methods in molecular biology*, Vol 483, pages 41-50; Liu and Lomonossoff, 2002, *Journal of Virological Methods,* 105:343-348; which is incorporated herein by reference). Alternatively, a vacuum-based transient expression method, as described by Kapila et al., (1997*, Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacteria* infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy RRD ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al., (Cell Culture and Somatic Cell Genetics of Plants, Vol I, II and III, Laboratory Procedures and Their Applications, Academic Press, 1984), and Weissbach and Weissbach, (Methods for Plant Molecular Biology, Academic Press, 1989). The method of obtaining transformed and regenerated plants is not critical to the present invention.

If plants, plant portions or plant cells are to be transformed or co-transformed by two or more nucleic acid constructs, the nucleic acid construct may be introduced into the *Agrobacterium* in a single transfection event the nucleic acids are pooled, and the bacterial cells transfected as described. Alternately, the constructs may be introduced serially. In this case, a first construct is introduced to the *Agrobacterium* as described, the cells grown under selective conditions (e.g. in the presence of an antibiotic) where only the singly transformed bacteria can grow. Following this first selection step, a second nucleic acid construct is introduced to the *Agrobacterium* as described, and the cells grown under doubly-selective conditions, where only the doubly-transformed bacteria can grow. The doubly-transformed bacteria may then be used to transform a plant, plant portion or plant cell as described herein, or may be subjected to a further transformation step to accommodate a third nucleic acid construct.

Alternatively, if plants, plant portions, or plant cells are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various *Agrobacteria* populations comprising the desired constructs may be varied.

The present disclosure further provides a transgenic plant comprising the expression system as defined herein, wherein the heterologous nucleic acid of interest in the cassette is expressed at an enhanced level when compared to other analogous expression systems that lack one or more components of the expression system as described herein, for example CPMV HT (SEQ ID NO:2).

The present disclosure further comprises a method for generating a protein of interest, comprising the steps of providing a plant, or plant part, that expresses the expression system as described herein, harvesting, at least, a tissue in which the protein of interest has been expressed and optionally, isolating the protein of interest from the tissue.

Thus in various aspects, and without limitation, the invention provides:

- an expression enhancer, comprising a comovirus 5'UTR selected from SEQ ID NO's:1 or 3, or a nucleotide sequence that exhibits 100%, 99%, 98%, 97%, 96%, 95%, 90%, 85% or 80% identity to the sequence as set forth in any one of SEQ ID NO's:1 or 3, wherein the expression enhancer, when operatively linked to a plant regulatory region and a kozak sequence active in a plant, for example a plant kozak sequence, as described herein, increases the level of expression of a nucleotide sequence of interest that is operatively linked to the expression enhancer when compared to the level of expression of the nucleotide sequence of interest fused to the CPMV HT (SEQ ID NO:2; prior art enhancer sequence comprising an incomplete M protein as described in Sainsbury F., and Lomonossoff G. P., 2008, Plant Physiol. 148: pp. 1212-1218; which is incorporated herein by reference) using the same plant regulatory region.
- one or more expression systems comprising a comovirus-based expression enhancer or expression cassette as defined above, a promoter (regulatory region), optionally a polylinker, a kozak sequence, a nucleic acid encoding a protein of interest, and a terminator.
- methods of expressing a protein of interest, in a host organism such as a plant using one or more expression systems or vectors as described herein.
- host cells and organisms expressing proteins of interest from the one or more expression systems or vectors of the invention and methods of producing the hosts and organisms.

TABLE 2 lists of sequences

| SEQ ID NO | Description |
|---|---|
| 1 | CPMV HT+ |
| 2 | CPMV HT |
| 3 | CPMV HT+ WT115 |
| | CPMV HT+ (plant kozak consensus sequence) |
| | Consensus plant kingdom kozak sequence |
| | Consensus dicot kozak sequence |
| | Consensus Arabidopsis kozak sequence |
| | kozak sequence AGAAA |
| | kozak sequence AGACA |
| | kozak sequence AGGAA |
| | kozak sequence AAAAA |
| | kozak sequence AAACA |
| | kozak sequence AAGCA |
| | kozak sequence AAGAA |
| | kozak sequence AAAGAA |
| | kozak sequence AAAAGAA |
| | Consensus kozak sequence (A/—)A(A/G)(A/G)(A/C)A |
| 18 | Primer IF-PDI.S1+3c |
| 19 | Primer IF-H3V36111.s1-4r |
| 20 | Nucleotide sequence of PDISP/H3 Victoria |
| 21 | Nucleotide sequence of Construct 1191 |
| 22 | Nucleotide sequence of expression cassette 1391 |
| 23 | Amino acid sequence of PDISP/H3 Victoria |
| 24 | Primer IF(SacII)-Kozac_PDI.c |
| 25 | Nucleotide sequence of Construct 2181 |
| 26 | Nucleotide sequence of expression cassette 1819 |
| 27 | Primer IF-HT1*-PDI.c |
| 28 | Primer IF-HT2*-PDI.c |
| 29 | Primer IF-HT3*-PDI.c |
| 30 | Primer IF-HT4*-PDI.c |
| 31 | Primer IF-HT5*-PDI.c |
| 32 | Primer IF-HT6*-PDI.c |
| 33 | IF-HT7*-PDI.c |
| 34 | IF-HT8*-PDI.c |
| 35 | Nucleotide sequence of PDISP/H1 California |
| 36 | Amino acid sequence of PDISP/H1 California |
| 37 | Nucleotide sequence of PDISP H5 Indonesia |
| 38 | Amino acid sequence of PDISP H5 Indonesia |
| 39 | Nucleotide sequence of PDISP/H7 Hangzhou |
| 40 | Amino acid sequence of PDISP/H7 Hangzhou |
| 41 | Nucleotide sequence of PDISP/H7 Hangzhou+H5 Indonesia TMCT |
| 42 | Amino acid sequence of PDISP/H7 Hangzhou+H5 Indonesia TMCT |
| 43 | Nucleotide sequence of PDISP/HA B Brisbane (PrL−) |
| 44 | Amino acid sequence of PDISP/HA B Brisbane (PrL−) |
| 45 | Nucleotide sequence of PDISP/HA B Brisbane (PrL−)+H1 California TMCT |
| 46 | Amino acid sequence of PDISP/HA B Brisbane (PrL−)+H1 California TMCT |
| 47 | Nucleotide sequence of PDISP/HA B Massachusetts (PrL−) |

TABLE 2-continued

| lists of sequences | |
|---|---|
| SEQ ID NO | Description |
| 48 | Amino acid sequence of PDISP/HA B Massachusetts (PrL−) |
| 49 | Nucleotide sequence of PDISP/HA B Massachusetts (PrL−)+H1 California TMCT |
| 50 | Amino acid sequence of PDISP/HA B Massachusetts (PrL−)+H1 California TMCT |
| 51 | Nucleotide sequence of HA B Wisconsin (PrL−) |
| 52 | Amino acid sequence of HA B Wisconsin (PrL−) |
| 53 | Nucleotide sequence of HA B Wisconsin (PrL−)+H1 California TMCT |
| 54 | Amino acid sequence of HA B Wisconsin (PrL−)+H1 California TMC |
| 55 | Segment of native CPMV RNA 2 genome, nucleotides 1-514, (WO2009/087391, Table 1) |
| 56 | CPMV RNA 2 genome, nucleotides 1-514, with modifications at 115 and 162 |
| 57 | Patatin signal peptide (nucleotide sequence) |
| 58 | Patatin signal peptide (amino acid sequence) |
| 59 | HA transmembrane domain consensus amino acid sequence |

Example 1: 2X35S/CPMV-HT/PDISP/H3 Victoria/NOS (Construct Number 1391)

Figure 5D:
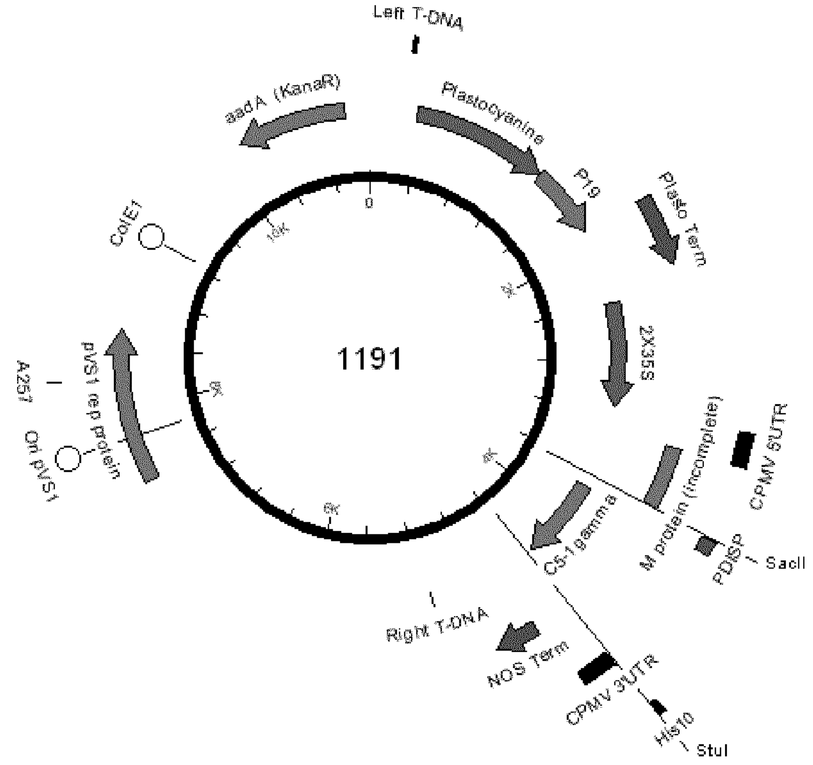
FIG. 5D shows a schematic representation of construct 1191.

A sequence encoding H3 from Influenza A/Victoria/361/2011 in which the native signal peptide has been replaced by that of alfalfa protein disulfide isomerase (PDISP/H3 Victoria) was cloned into 2X35S-CPMV-HT-NOS expression using the following PCR-based method. A fragment containing the PDISP/H3 Victoria coding sequence was amplified using primers IF-PDI.S1+3c (FIG. 5A, SEQ ID NO: 18) and IF-H3V36111.s1-4r (FIG. 5B, SEQ ID NO: 19), using PDISP/H3 Victoria sequence (FIG. 5C, SEQ ID NO: 20) as template. The PCR product was cloned in 2X35S/CPMV-HT/NOS expression system using In-Fusion cloning system (Clontech, Mountain View, Calif.). Construct number 1191 (FIGS. 5D and 5E, SEQ ID NO: 21) was digested with SacII and StuI restriction enzyme and the linearized plasmid was used for the In-Fusion assembly reaction. Construct number 1191 is an acceptor plasmid intended for "In Fusion" cloning of genes of interest in a CPMV-HT-based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 5E (SEQ ID NO: 21). The resulting construct was given number 1391 (FIG. 5F, SEQ ID NO: 22). The amino acid sequence of mature H3 from Influenza A/Victoria/361/2011 fused with PDISP is presented in FIG. 5G (SEQ ID NO: 23). A representation of plasmid 1391 is presented in FIG. 5H.

Example 2: 2X35S/CPMV-HT+/PDISP/H3 Victoria/NOS (Construct Number 1819)

Figure 6E:
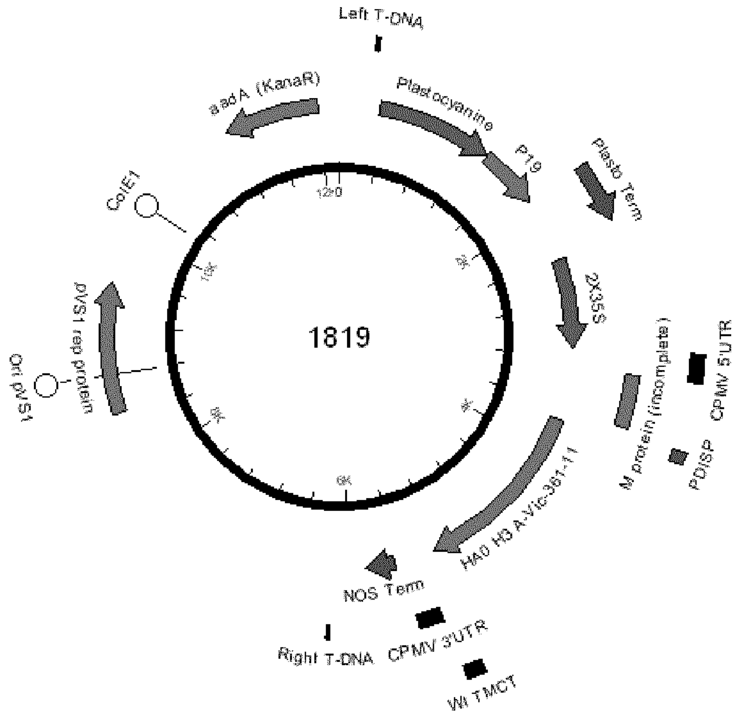
FIG. 6E shows a schematic representation of construct 1819.

A sequence encoding H3 from Influenza A/Victoria/361/2011 in which the native signal peptide has been replaced by that of alfalfa protein disulfide isomerase (PDISP/H3 Victoria) was cloned into 2X35S-CPMV-HT+/NOS expression using the following PCR-based method. A fragment containing the PDISP/H3 Victoria coding sequence was amplified using primers IF(SacII)-Kozac_PDI.c (FIG. 6A, SEQ ID NO: 24) and IF-H3V36111.s1-4r (FIG. 5B, SEQ ID NO: 19), using PDISP/H3 Victoria sequence (FIG. 8C, SEQ ID NO: 20) as template. The PCR product was cloned in 2X35S/CPMV-HT+/NOS expression system using In-Fusion cloning system (Clontech, Mountain View, Calif.). Construct number 2181 (FIG. 6B) was digested with SacII and StuI restriction enzyme and the linearized plasmid was used for the In-Fusion assembly reaction. Construct number 2181 is an acceptor plasmid intended for "In Fusion" cloning of genes of interest in a CPMV-HT+ based expression cassette. It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in FIG. 6C (SEQ ID NO: 25). The resulting construct was given number 1819 (FIG. 6D, SEQ ID NO: 26). The amino acid sequence of mature H3 from Influenza A/Victoria/361/2011 fused with PDISP is presented in FIG. 5G (SEQ ID NO: 23). A representation of plasmid 1819 is presented in FIG. 6E.

Example 3 Variation of Sequence Between SacII Restriction Site and ATG of PDISP/H3 Victoria in 2X35S/CPMV HT+/NOS Expression System (Constructs Number 1952 to 1959)

Eight constructs comprising sequence variations between SacII restriction site and the ATG of PDISP/H3 Victoria in 2X35S/CPMV HT+/NOS expression system were created using the same PCR-based method as in construct no 1819 (see Example 2) with a modified forward primer and keeping all other steps the same. Variant HT1* to HT8* were amplified using the primers listed in Figures FIG. 7A-7H:

IF-HT1*(-Mprot)-PDI.c (FIG. 7A, SEQ ID NO: 27),
IF-HT2*(-Mprot)-PDI.c (FIG. 7B, SEQ ID NO: 28),
IF-HT3*(-Mprot)-PDI.c (FIG. 7C, SEQ ID NO: 29)
IF-HT4*(-Mprot)-PDI.c (FIG. 7D, SEQ ID NO: 30)
IF-HT5*(-Mprot)-PDI.c (FIG. 7E, SEQ ID NO: 31)
IF-HT6*(-Mprot)-PDI.c (FIG. 7F, SEQ ID NO: 32)
IF-HT7*(-Mprot)-PDI.c (FIG. 7G, SEQ ID NO: 33) and
IF-HT8*(-Mprot)-PDI.c (FIG. 7H, SEQ ID NO: 34), to create construct no 1952 to 1959, respectively. Representation of plasmid 1952 is presented in FIG. 7I. Analogous features were used to prepare constructs 1953-1959.

Example 4: 2X35S/CPMV HT (Construct No 484) and HT+ (Construct No 1805) for PDISP/H1 California A coding sequence corresponding to H1 from Influenza A/California/7/2009 in which the native signal peptide has been replaced by that of alfalfa protein disulfide isomerase (PDISP/H1 California) (FIG. 8A, SEQ ID NO: 35) was cloned into original HT and modified HT+ using the same PCR-based method as construct 1391 and 1819 (see Examples 1 and 2), respectively, but with modified PCR primers specifically designed for PDISP/H1 California. The amino acid sequence of mature H1 from Influenza A/California/7/2009 fused with PDISP is presented in FIG. 8B (SEQ ID NO: 36). Representations of plasmid 484 and 1805 are presented in FIG. 8C and FIG. 8D.

Example 5: 2X35S/CPMV HT (Construct No 409) and HT+ (Construct No 2319) for H5 Indonesia A coding sequence corresponding to H5 from Influenza A/Indonesia/5/2005 in which the native signal peptide has been replaced by that of alfalfa protein disulfide isomerase (PDISP/H5 Indonesia) (FIG. 9A, SEQ ID NO: 37) was cloned into original HT and modified HT+ using the same PCR-based method as construct 1391 and 1819 (see Examples 1 and 2), respectively but with modified PCR primers specifically designed for PDI/H5 Indonesia. The amino acid sequence of mature H5 from Influenza A/Indonesia/5/2005 with PDISP is presented in FIG. 9B (SEQ ID NO: 38). Representations of plasmid 409 and 2319 are presented in FIG. 9C and FIG. 9D.

Example 6: 2X35S/CPMV HT (Construct No 2140) and HT+ (Construct No 2142) for PDISP-H7 Hangzhou A coding sequence corresponding to H7 from Influenza A/Hangzhou/1/2013 in which the native signal peptide has been replaced by that of alfalfa protein disulfide isomerase (PDISP/H7 Hangzhou) (FIG. 10A, SEQ ID NO: 39) was cloned into original HT and modified HT+ using the same PCR-based method as construct 1391 and 1819 (see Examples 1 and 2), respectively, but with modified PCR primers specifically designed for PDISP/H7 Hangzhou. The amino acid sequence of mature H7 from Influenza A/Hangzhou/1/2013 fused with PDISP is presented in FIG. 10B (SEQ ID NO: 40). Representations of plasmid 2140, 2142 and 2168 are presented in FIG. 10C and FIG. 10D.

Example 7: 2X35S/CPMV HT (Construct No 2130) and HT+ (Construct No 2146) for PDISP/H7 Hangzhou+H5 Indonesia TMCT A chimer hemagglutinin coding sequence corresponding to the ectodomain of H7 from Influenza A/Hangzhou/1/2013 fused to the transmembrane domain and cytoplasmic tail (TMCT) of H5 from influenza A/Indonesia/5/2005 and with the signal peptide of alfalfa protein disulfide isomerase (PDISP/H7 Hangzhou+H5 Indonesia TMCT) (FIG. 11A, SEQ ID NO: 41) was cloned into original HT and modified HT+ using the same PCR-based method as construct 1391 and 1819 (see Examples 1 and 2), respectively, but with modified PCR primers specifically designed for the PDISP/H7 Hangzhou+H5 Indonesia TMCT. The amino acid sequence of H7 Hangzhou+H5 Indonesia TMCT fused with PDISP is presented in FIG. 11B (SEQ ID NO: 42). Representations of plasmid 2130 and 2146 are presented in FIGS. 11C and 11D.

Example 8: 2X35S/CPMV HT (Construct No 1039) and HT+ (Construct No 1829) for PDISP/HA B Brisbane (PrL-)

Figure 12C:
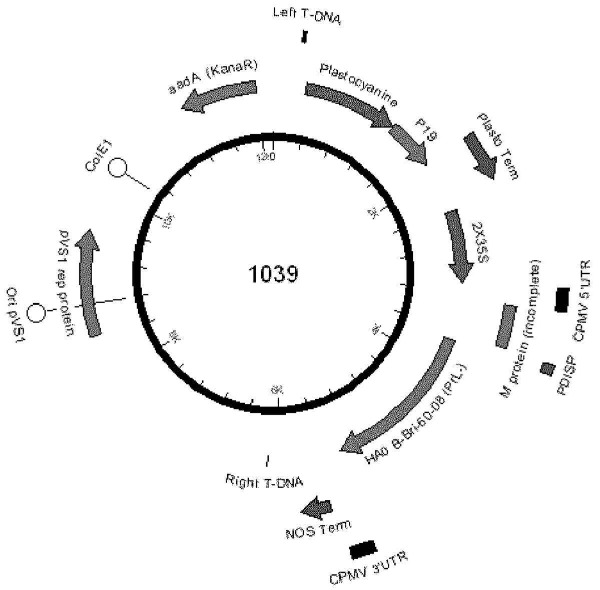
FIG. 12C shows a schematic representation of construct number 1039 (2X35S/CPMV HT; reference construct).
Figure 12D:
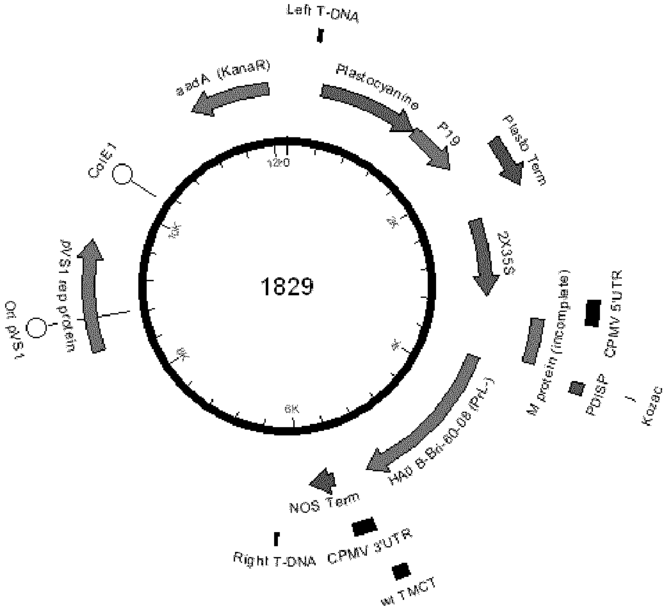
FIG. 12D shows a schematic representation of construct number 1829 (2X35S/CPMV HT+).

A coding sequence corresponding to HA from Influenza B/Brisbane/60/2008 with deleted proteolytic loop (PrL-) in which the native signal peptide has been replaced by that of alfalfa protein disulfide isomerase (PDISP/HA B Brisbane (PrL-; FIG. 12A, SEQ ID NO: 43) was cloned into original HT and modified HT+ using the same PCR-based method as construct 1391 and 1819 (see Examples 1 and 2), respectively, but with modified PCR primers specifically designed for PDISP/HA B Brisbane (PrL-). The amino acid sequence of mature HA B Brisbane (PrL-) fused with PDISP is presented in FIG. 12B (SEQ ID NO: 44). Representations of plasmid 1039 and 1829 are presented in FIGS. 12C and 12D.

Figure 13C:
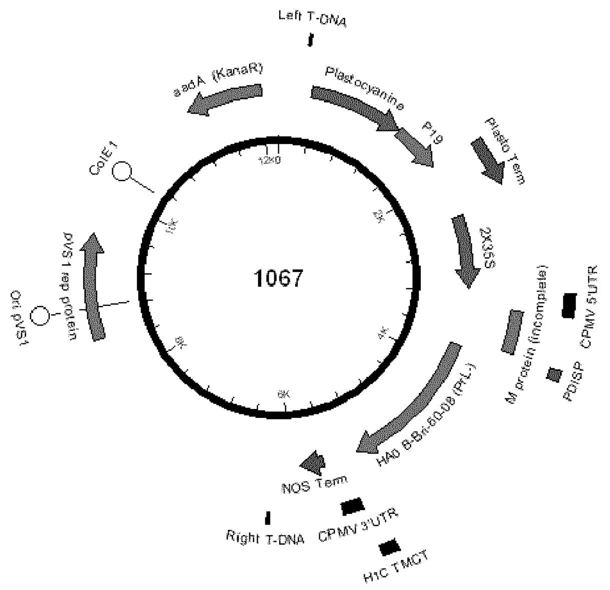
FIG. 13C shows a schematic representation of construct number 1067 (2X35S/CPMV HT; reference construct).
Figure 13D:
FIG. 13D shows a schematic representation of construct number 1875 (2X35S/CPMV160+).

Example 9: 2X35S/CPMV HT (construct no 1067) and HT+ (construct No 1875) for PDISP/HA B Brisbane (PrL-)+H1 California TMCT A chimer hemagglutinin coding sequence corresponding to the ectodomain of HA from Influenza B/Brisbane/60/08 with deleted proteolytic loop (PrL-) fused to the transmembrane domain and cytoplasmic tail (TMCT) of H1 from influenza A/California/7/2009 and with the signal peptide of alfalfa protein disulfide isomerase (PDISP/HA B Brisbane (PrL-)+H1 California TMCT) (FIG. 13A, SEQ ID NO: 45) was cloned into original HT and modified HT+ using the same PCR-based method as construct 1391 and 1819 (see examples 1 and 2), respectively, but with modified PCR primers specifically designed for PDISP/HA B Brisbane (PrL-)+H1 California TMCT. The amino acid sequence of mature HA B Brisbane (PrL-)+H1 California TMCT fused with PDISP is presented in FIG. 13B (SEQ ID NO: 46). Representations of plasmid 1067 and 1875 are presented in FIGS. 13C and 13D.

Example 10: 2X35S/CPMV HT (Construct No 2072) and HT+ (Construct No 2052) for PDISP/HA B Massachusetts (PrL-)

A coding sequence corresponding to HA from Influenza B/Massachusetts/2/2012 with deleted proteolytic loop (PrL-) in which the native signal peptide has been replaced by that of alfalfa protein disulfide isomerase (PDISP/HA B Massachusetts (PrL-)) (FIG. 14A, SEQ ID NO: 47) was cloned into original HT and modified HT+ using the same PCR-based method as construct 1391 and 1819 (see Examples 1 and 2), respectively, but with modified PCR primers specifically designed for PDISP/HA B Massachusetts (PrL-). The amino acid sequence of mature HA B Massachusetts (PrL-) fused with PDISP is presented in FIG. 14B (SEQ ID NO: 48). Representations of plasmid 2072 and 2052 are presented in FIG. 14C and FIG. 14D.

Example 11: 2X35S/CPMV HT (Construct No 2074) and HT+ (Construct No 2062) for PDISP/HA B Massachusetts (PrL-)+H1 California TMCT A chimer hemagglutinin coding sequence corresponding to the ectodomain of HA from Influenza B/Massachusetts/2/2012 with deleted proteolytic loop (PrL-) fused to the transmembrane domain and cytoplasmic tail (TMCT) of H1 from influenza A/California/7/2009 and with the signal peptide of alfalfa protein disulfide isomerase (PDISP/HA B Massachusetts (PrL-)+H1 California TMCT) (FIG. 15A, SEQ ID NO: 49) was cloned into original HT and modified HT+ using the same PCR-based method as construct 1391 and 1819 (see Examples 1 and 2), respectively, but with modified PCR primers specifically designed for PDISP/HA B Massachusetts (PrL-)+H1 California TMCT. The amino acid sequence of mature HA B Massachusetts (PrL-)+H1 California TMCT fused with PDISP is presented in FIG. 15B (SEQ ID NO: 50). Representations of plasmid 2074 and 2062 are presented in FIG. 15C and FIG. 15D.

Example 12: 2X35S/CPMV HT (Construct No 1445) and HT+ (Construct No 1839) for HA B Wisconsin (PrL-)

Figure 16C:
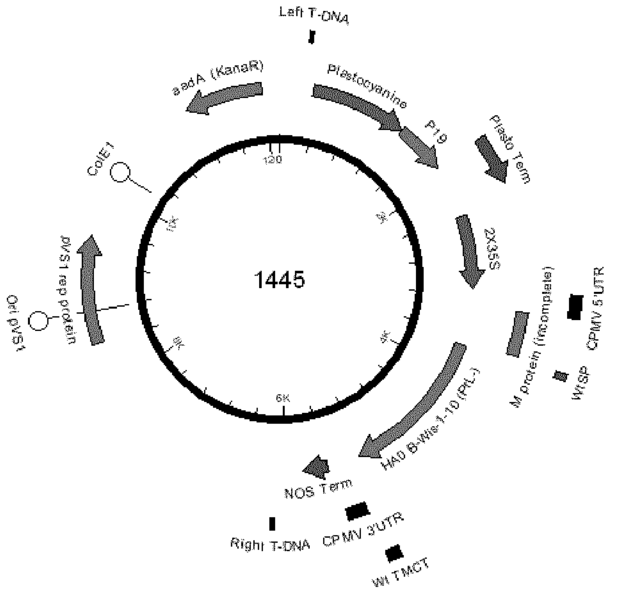
FIG. 16C shows a schematic representation of construct number 1445 (2X35S/CPMV HT; reference construct).
Figure 16D:
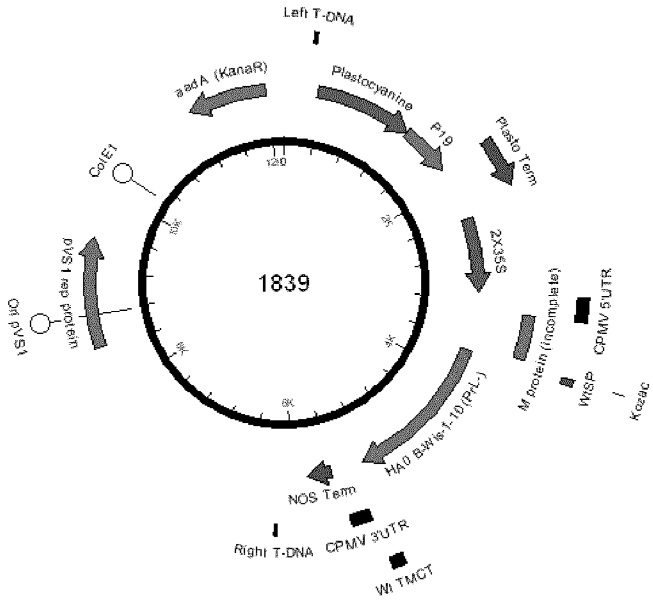
FIG. 16D shows a schematic representation of construct number 1839 (2X35S/CPMV HT+).

A coding sequence corresponding to HA from Influenza B/Wisconsin/1/2010 with deleted proteolytic loop (PrL-)

with his native signal peptide (HA B Wisconsin (PrL-)) (FIG. 16A, SEQ ID NO: 51) was cloned into original HT and modified HT+ using the same PCR-based method as construct 1391 and 1819 (see Examples 1 an 2), respectively, but with modified PCR primers specifically designed for HA B Wisconsin (PrL-). The amino acid sequence of HA B Wisconsin (PrL-) with his native signal peptide is presented in FIG. 16B (SEQ ID NO: 52). Representations of plasmid 1445 and 1839 are presented in FIGS. 16C and 16D.

Figure 17C:
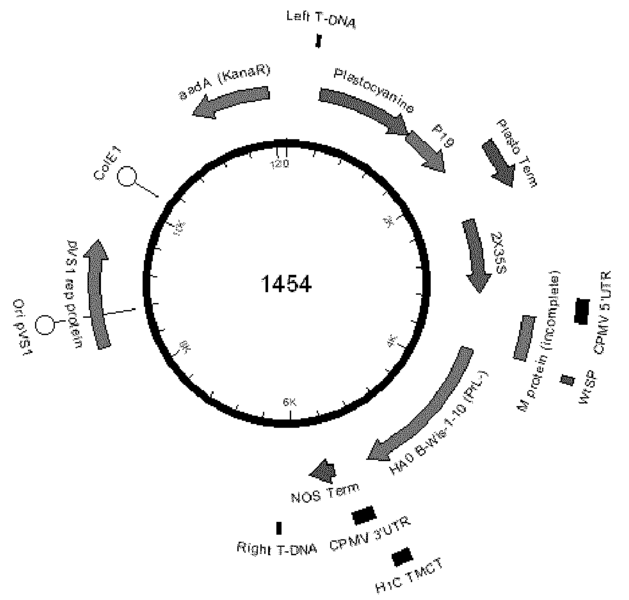
FIG. 17C shows a schematic representation of construct number 1454 (2X35S/CPMV HT; reference construct).
Figure 17D:
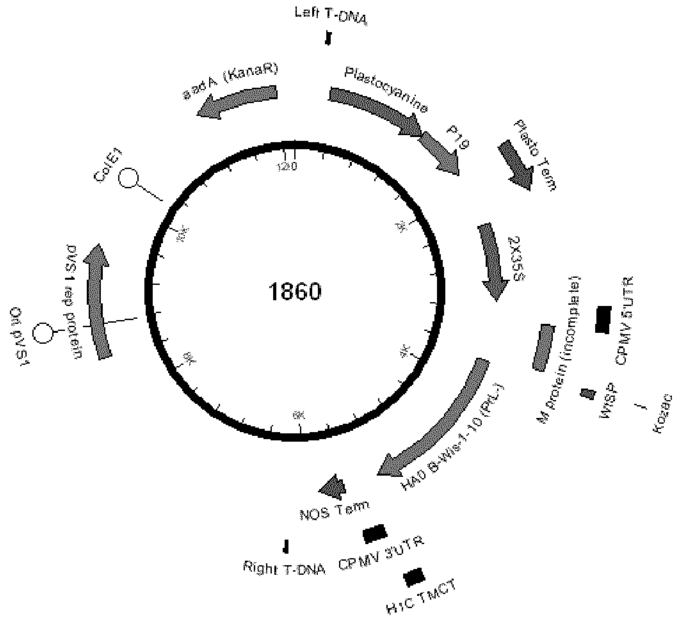
FIG. 17D shows a schematic representation of construct number 1893 (2X35S/CPMV HT+).

Example 13: 2X35S/CPMV HT (Construct No 1454) and HT+ (Construct No 1860) for HA B Wisconsin (PrL-)+H1 California TMCT A chimer hemagglutinin coding sequence corresponding to the ectodomain of HA from Influenza B/Wisconsin/2/2012 with deleted proteolytic loop (PrL-) fused to the transmembrane domain and cytoplasmic tail (TMCT) of H1 from influenza A/California/7/2009 with the native signal peptide of HA B Wisconsin (HA B Wisconsin (PrL-)+H1 California TMCT) (FIG. 17A, SEQ ID NO: 53) was cloned into original HT and modified HT+ using the same PCR-based method as construct 1391 and 1819, respectively, but with modified PCR primers specifically designed for HA B Wisconsin (PrL-)+H1 California TMCT. The amino acid sequence of HA B Wisconsin (PrL-)+H1 California TMCT is presented in FIG. 17B (SEQ ID NO: 54). Representations of plasmid 1454 and 1860 are presented in FIGS. 17C and 17D.

Example 14: *Agrobacterium* Transfection

*Agrobacterium* strain AGL1 was transfected by electroporation with the DNA constructs using the methods described by D'Aoust et al 2008 (Plant Biotechnology Journal 6:930-940). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

The terms “biomass” and “plant matter” as used herein are meant to reflect any material derived from a plant. Biomass or plant matter may comprise an entire plant, tissue, cells, or any fraction thereof. Further, biomass or plant matter may comprise intracellular plant components, extracellular plant components, liquid or solid extracts of plants, or a combination thereof. Further, biomass or plant matter may comprise plants, plant cells, tissue, a liquid extract, or a combination thereof, from plant leaves, stems, fruit, roots or a combination thereof. A portion of a plant may comprise plant matter or biomass.

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions.

*Agrobacteria* transfected with each construct were grown in a YEB medium supplemented with 10 mM 2-(N-morpholino)ethanesulfonic acid (MES), 20 μM acetosyringone, 50 μg/ml kanamycin and 25 μg/ml of carbenicillin pH 5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 2-6 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 3 volumes of cold 50 mM Tris pH 8.0, 0.15 M NaCl, 0.1% Triton X-100 and 1 mM phenylmethanesulfonyl fluoride. After homogenization, the slurries were centrifuged at 10,000 g for 10 min at 4° C. and these clarified crude extracts (supernatant) kept for analyses.

Example 15: Hemagglutination Assay

The total protein content of clarified crude extracts was determined by the Bradford assay (Bio-Rad, Hercules, Calif.) using bovine serum albumin as the reference standard.

Hemagglutination assay was based on a method described by Nayak and Reichl (2004). Briefly, serial double dilutions of the test samples (100 μL) were made in V-bottomed 96-well microtiter plates containing 100 μL PBS, leaving 100 μL of diluted sample per well. One hundred microliters of a 0.25% turkey red blood cells suspension (Bio Link Inc., Syracuse, N.Y.; for all B strains, H1, H5 and H7) or 0.5% guinea pig red blood cells suspension (for H3) were added to each well, and plates were incubated for 2h at room temperature. The reciprocal of the highest dilution showing complete hemagglutination was recorded as HA activity.

All citations are hereby incorporated by reference.

The present invention has been described with regard to one or more embodiments. However, it will be apparent to persons skilled in the art that a number of variations and modifications can be made without departing from the scope of the invention as defined in the claims.

We claim:

1. An expression enhancer comprising, in series, a CPMV 5' UTR and a stuffer fragment, the CPMV 5' UTR consisting of nucleotides 1-114 and 118-160 of SEQ ID NO:1 and an ATG or a non-ATG codon at nucleotides 115-117 of the CPMV 5' UTR, the stuffer fragment comprising a nucleotide sequence encoding an incomplete M protein and one or more Kozak sequences, the incomplete M protein comprising nucleotides 164-509 of SEQ ID NO:1 and an ATG or a non-ATG codon at nucleotides 161-163 of the incomplete M protein, the one or more Kozak sequences comprising the nucleotide sequence AGAAA, AGACA, AGGAA or AAGCA.

2. The expression enhancer of claim 1, wherein the stuffer fragment comprises a length from 349 to about 500 nucleotides, or any length therebetween.

3. The expression enhancer of claim 2, wherein the stuffer fragment further comprises a multiple cloning site.

4. The expression enhancer of claim 1, wherein the nucleotide sequence encoding the incomplete M protein is either 349 or 351 nucleotides long.

5. The expression enhancer of claim 1 wherein nucleotide 115 of the CPMV 5'UTR is adenine or guanine.

6. A plant expression system comprising a nucleic acid sequence comprising a regulatory region, operatively linked with the expression enhancer of claim 1 and a nucleotide sequence of interest.

7. The plant expression system of claim 6, further comprising a comovirus 3' UTR.

8. The plant expression system of claim 7, further comprising a second nucleic acid sequence, the second nucleic acid sequence encoding a suppressor of silencing.

9. The plant expression system of claim 8 wherein the suppressor of silencing is selected from the group consisting of HcPro and p19.

10. The plant expression system of claim 6, wherein the regulatory region is selected from the group consisting of a plastocyanin promoter, a CaMV 35S promoter, a 2× CaMV35S promoter, a CAS promoter, a RbcS promoter, a Ubi promoter, and an actin promoter.

11. The plant expression system of claim 6, wherein the nucleotide sequence of interest encodes a viral protein or an antibody.

12. The plant expression system of claim 11, wherein the viral protein is an influenza hemagglutinin selected from the group consisting of H1, H2, H3, H4, H5, H6, H7, H8, H9, H10, H11, H12, H13, H14, H15, H16, and influenza type B hemagglutinin.

13. The plant expression system of claim 12, wherein the nucleotide sequence encoding the viral protein or the antibody comprises a native signal peptide sequence, or a non-native signal peptide.

14. The plant expression system of claim 13, wherein the non-native signal peptide is from Protein disulfide isomerase (PDI).

15. A method of producing a protein of interest in a plant or in a portion of a plant comprising, introducing into the plant or in the portion of a plant the plant expression system of claim 6, and incubating the plant or the portion of a plant under conditions that permit expression of the nucleotide sequence encoding the protein of interest.

16. A plant or portion of a plant transiently transfected or stably transformed with the plant expression system of claim 6.

17. A nucleic acid comprising the expression enhancer of claim 1, operatively linked to a nucleotide sequence of interest.

18. The nucleic acid of claim 17, wherein the nucleotide sequence of interest is an influenza hemagglutinin (HA), selected from B HA, C, H1, H2, H3, H4, H5, H6, H7, H8, H9, H10, H11, H12, H13, H14, H15, and H16.

19. The nucleic acid of claim 18, wherein the HA is a chimeric HA, wherein a native trans-membrane domain of the HA is replaced with a heterologous trans-membrane domain.

20. The nucleic acid of claim 19, wherein the heterologous trans-membrane domain is obtained from H1 California.

21. The expression enhancer of claim 1, wherein the nucleotide sequence encoding the incomplete M protein comprises: nucleotides 161 to 509 of any one of SEQ ID NOs:1-4, nucleotides 161-511 of SEQ ID NO:55, or nucleotides 161-511 of SEQ ID NO:56.

* * * * *

SEQUENCE LISTING

```
<160> NUMBER OF SEQ ID NOS: 59

<210> SEQ ID NO 1
<211> LENGTH: 534
<212> TYPE: DNA
<213> ORGANISM: Artificial Sequence
<220> FEATURE:
```

```
<223> OTHER INFORMATION: Expression enhancer comprising CPMV HT+

<400> SEQUENCE: 1

tattaaaatc ttaataggtt ttgataaaag cgaacgtggg gaaacccgaa ccaaaccttc     60

ttctaaactc tctctcatct ctcttaaagc aaacttctct cttgtctttc ttgcgtgagc    120

gatcttcaac gttgtcagat cgtgcttcgg caccagtaca acgttttctt tcactgaagc    180

gaaatcaaag atctctttgt ggacacgtag tgcggcgcca ttaaataacg tgtacttgtc    240

ctattcttgt cggtgtggtc ttgggaaaag aaagcttgct ggaggctgct gttcagcccc    300

atacattact tgttacgatt ctgctgactt tcggcgggtg caatatctct acttctgctt    360

gacgaggtat tgttgcctgt acttctttct tcttcttctt gctgattggt tctataagaa    420

atctagtatt ttctttgaaa cagagttttc ccgtggtttt cgaacttgga gaaagattgt    480

taagcttctg tatattctgc ccaaatttgt tcgggcccaa taccgcggag aaaa          534


<210> SEQ ID NO 2
<211> LENGTH: 517
<212> TYPE: DNA
<213> ORGANISM: Artificial Sequence
<220> FEATURE:
<223> OTHER INFORMATION: Expression enhancer CPMV HT

<400> SEQUENCE: 2

tattaaaatc ttaataggtt ttgataaaag cgaacgtggg gaaacccgaa ccaaaccttc     60

ttctaaactc tctctcatct ctcttaaagc aaacttctct cttgtctttc ttgcgtgagc    120

gatcttcaac gttgtcagat cgtgcttcgg caccagtaca acgttttctt tcactgaagc    180

gaaatcaaag atctctttgt ggacacgtag tgcggcgcca ttaaataacg tgtacttgtc    240

ctattcttgt cggtgtggtc ttgggaaaag aaagcttgct ggaggctgct gttcagcccc    300

atacattact tgttacgatt ctgctgactt tcggcgggtg caatatctct acttctgctt    360

gacgaggtat tgttgcctgt acttctttct tcttcttctt gctgattggt tctataagaa    420

atctagtatt ttctttgaaa cagagttttc ccgtggtttt cgaacttgga gaaagattgt    480

taagcttctg tatattctgc ccaaatttgt cgggccc                             517


<210> SEQ ID NO 3
<211> LENGTH: 534
<212> TYPE: DNA
<213> ORGANISM: Artificial Sequence
<220> FEATURE:
<223> OTHER INFORMATION: CPMV HT+[WT115]

<400> SEQUENCE: 3

tattaaaatc ttaataggtt ttgataaaag cgaacgtggg gaaacccgaa ccaaaccttc     60

ttctaaactc tctctcatct ctcttaaagc aaacttctct cttgtctttc ttgcatgagc    120

gatcttcaac gttgtcagat cgtgcttcgg caccagtaca acgttttctt tcactgaagc    180

gaaatcaaag atctctttgt ggacacgtag tgcggcgcca ttaaataacg tgtacttgtc    240

ctattcttgt cggtgtggtc ttgggaaaag aaagcttgct ggaggctgct gttcagcccc    300

atacattact tgttacgatt ctgctgactt tcggcgggtg caatatctct acttctgctt    360

gacgaggtat tgttgcctgt acttctttct tcttcttctt gctgattggt tctataagaa    420

atctagtatt ttctttgaaa cagagttttc ccgtggtttt cgaacttgga gaaagattgt    480

taagcttctg tatattctgc ccaaatttgt tcgggcccaa taccgcggag aaaa          534
```

<210> SEQ ID NO 4
<211> LENGTH: 534
<212> TYPE: DNA
<213> ORGANISM: Artificial Sequence
<220> FEATURE:
<223> OTHER INFORMATION: CPMV HT+ (plant kozak consensus sequence)
<220> FEATURE:
<221> NAME/KEY: misc_feature
<222> LOCATION: (529)..(529)
<220> FEATURE:
<221> NAME/KEY: misc_feature
<222> LOCATION: (529)..(529)
<223> OTHER INFORMATION: a may be present or absent

<400> SEQUENCE: 4
tattaaaatc ttaataggtt ttgataaaag cgaacgtggg gaaacccgaa ccaaaccttc 60
ttctaaactc tctctcatct ctcttaaagc aaacttctct cttgtctttc ttgcgtgagc 120
gatcttcaac gttgtcagat cgtgcttcgg caccagtaca acgttttctt tcactgaagc 180
gaaatcaaag atctctttgt ggacacgtag tgcggcgcca ttaaataacg tgtacttgtc 240
ctattcttgt cggtgtggtc ttgggaaaag aaagcttgct ggaggctgct gttcagcccc 300
atacattact tgttacgatt ctgctgactt tcggcgggtg caatatctct acttctgctt 360
gacgaggtat tgttgcctgt acttctttct tcttcttctt gctgattggt tctataagaa 420
atctagtatt ttctttgaaa cagagttttc ccgtggtttt cgaacttgga gaaagattgt 480
taagcttctg tatattctgc ccaaatttgt tcgggcccaa taccgcggna rrma 534

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18
<211> LENGTH: 48
<212> TYPE: DNA
<213> ORGANISM: Artificial Sequence
<220> FEATURE:
<223> OTHER INFORMATION: IF-PDI.S1+3c

<400> SEQUENCE: 18
aaatttgtcg ggcccatggc gaaaaacgtt gcgattttcg gcttattg 48

<210> SEQ ID NO 19
<211> LENGTH: 51
<212> TYPE: DNA
<213> ORGANISM: Artificial Sequence
<220> FEATURE:
<223> OTHER INFORMATION: IF-H3V36111.s1-4r

<400> SEQUENCE: 19
actaaagaaa ataggccttc aaatgcaaat gttgcaccta atgttgccct t 51

<210> SEQ ID NO 20
<211> LENGTH: 1725
<212> TYPE: DNA
<213> ORGANISM: Artificial Sequence
<220> FEATURE:
<223> OTHER INFORMATION: Nucleotide sequence of PDISP/H3 Victoria

<400> SEQUENCE: 20

```
atggcgaaaa acgttgcgat tttcggctta ttgttttctc ttcttgtgtt ggttccttct     60

cagatcttcg cccaaaaact tcctggaaat gacaacagca cggcaacgct gtgccttggg    120

caccatgcag taccaaacgg aacgatagtg aaaacaatca cgaatgacca aattgaagtt    180

actaatgcta ctgagctggt tcagaattcc tcaataggtg aaatatgcga cagtcctcat    240

cagatccttg atggagaaaa ctgcacacta atagatgctc tattgggaga ccctcagtgt    300

gatggcttcc aaaataagaa atgggacctt tttgttgaac gaagcaaagc ctacagcaac    360

tgttaccctt atgatgtgcc ggattatgcc tcccttaggt cactagttgc ctcatccggc    420

acactggagt ttaacaatga aagcttcaat tggactggag tcactcaaaa cggaacaagt    480

tctgcttgca taaggagatc taataatagt ttctttagta gattaaattg gttgacccac    540

ttaaacttca aatacccagc attgaacgtg actatgccaa acaatgaaca atttgacaaa    600

ttgtacattt gggggttca ccacccgggt acggacaagg accaaatctt cctgtatgct    660

caatcatcag gaagaatcac agtatctacc aaaagaagcc aacaagctgt aatcccgaat    720

atcggatcta gacccagaat aaggaatatc cctagcagaa taagcatcta ttggacaata    780

gtaaaaccgg gagacatact tttgattaac agcacaggga atctaattgc tcctaggggt    840

tacttcaaaa tacgaagtgg gaaaagctca ataatgagat cagatgcacc cattggcaaa    900

tgcaattctg aatgcatcac tccaaatgga agcattccca atgacaaacc attccaaaat    960

gtaaacagga tcacatacgg ggcctgtccc agatatgtta agcaaagcac tctgaaattg   1020

gcaacaggaa tgcgaaatgt accagagaaa caaactagag gcatatttgg cgcaatagcg   1080

ggtttcatag aaaatggttg ggagggaatg gtggatggtt ggtacggttt caggcatcaa   1140

aattctgagg gaagaggaca agcagcagat ctcaaaagca ctcaagcagc aatcgatcaa   1200

atcaatggga agctgaatcg attgatcggg aaaaccaacg agaaattcca tcagattgaa   1260

aaagaattct cagaagtcga agggagaatt caggaccttg agaaatatgt tgaggacact   1320

aaaatagatc tctggtcata caacgcggag cttcttgttg ccctggagaa ccaacataca   1380

attgatctaa ctgactcaga aatgaacaaa ctgtttgaaa aaacaaagaa gcaactaagg   1440

gaaaatgctg aggatatggg caatggttgt ttcaaaatat accacaaatg tgacaatgcc   1500

tgcataggat caatcagaaa tggaacttat gaccacgatg tatacagaga tgaagcatta   1560

aacaaccggt tccagatcaa gggagttgag ctgaagtcag ggtacaaaga ttggatccta   1620

tggatttcct ttgccatatc atgtttttttg ctttgtgttg ctttgttggg gttcatcatg   1680

tgggcctgcc aaaagggcaa cattaggtgc aacatttgca tttga                   1725
```

<210> SEQ ID NO 21
<211> LENGTH: 4903
<212> TYPE: DNA
<213> ORGANISM: Artificial Sequence
<220> FEATURE:
<223> OTHER INFORMATION: Nucleotide sequence of construct 1191

<400> SEQUENCE: 21

```
tggcaggata tattgtggtg taaacaaatt gacgcttaga caacttaata acacattgcg     60

gacgttttta atgtactgaa ttaacgccga atcccgggct ggtatattta tatgttgtca    120

aataactcaa aaaccataaa agtttaagtt agcaagtgtg tacatttttta cttgaacaaa    180

aatattcacc tactactgtt ataaatcatt attaaacatt agagtaaaga aatatggatg    240

ataagaacaa gagtagtgat attttgacaa caattttgtt gcaacatttg agaaaatttt    300
```

-continued

```
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
```

```
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccagtaca acgttttctt   3060
tcactgaagc gaaatcaaag atctctttgt ggacacgtag tgcggcgcca ttaaataacg   3120
tgtacttgtc ctattcttgt cggtgtggtc ttgggaaaag aaagcttgct ggaggctgct   3180
gttcagcccc atacattact tgttacgatt ctgctgactt tcggcgggtg caatatctct   3240
acttctgctt gacgaggtat tgttgcctgt acttctttct tcttcttctt gctgattggt   3300
tctataagaa atctagtatt ttctttgaaa cagagttttc ccgtggtttt cgaacttgga   3360
gaaagattgt taagcttctg tatattctgc ccaaatttgt cgggcccgcg gatggcgaaa   3420
aacgttgcga ttttcggctt attgttttct cttcttgtgt tggttccttc tcagatcttc   3480
gcctgcaggc tcctcagcca aaacgacacc cccatctgtc tatccactgg cccctggatc   3540
tgctgcccaa actaactcca tggtgaccct gggatgcctg gtcaagggct atttccctga   3600
gccagtgaca gtgacctgga actctggatc cctgtccagc ggtgtgcaca ccttcccagc   3660
tgtcctgcag tctgacctct acactctgag cagctcagtg actgtcccct ccagcacctg   3720
gcccagcgag accgtcacct gcaacgttgc ccacccggcc agcagcacca aggtggacaa   3780
gaaaattgtg cccagggatt gtggttgtaa gccttgcata tgtacagtcc cagaagtatc   3840
atctgtcttc atcttccccc caaagcccaa ggatgtgctc accattactc tgactcctaa   3900
ggtcacgtgt gttgtggtag acatcagcaa ggatgatccc gaggtccagt tcagctggtt   3960
tgtagatgat gtggaggtgc acacagctca gacgcaaccc cgggaggagc agttcaacag   4020
cactttccgc tcagtcagtg aacttcccat catgcaccag gactggctca atggcaagga   4080
gcgatcgctc accatcacca tcaccatcac catcaccatt aaaggcctat tttctttagt   4140
ttgaatttac tgttattcgg tgtgcatttc tatgtttggt gagcggtttt ctgtgctcag   4200
agtgtgttta ttttatgtaa tttaatttct ttgtgagctc ctgtttagca ggtcgtccct   4260
tcagcaagga cacaaaaaga ttttaatttt attaaaaaaa aaaaaaaaaa agaccgggaa   4320
ttcgatatca agcttatcga cctgcagatc gttcaaacat ttggcaataa agtttcttaa   4380
gattgaatcc tgttgccggt cttgcgatga ttatcatata atttctgttg aattacgtta   4440
agcatgtaat aattaacatg taatgcatga cgttatttat gagatgggtt tttatgatta   4500
gagtcccgca attatacatt taatacgcga tagaaaacaa aatatagcgc gcaaactagg   4560
ataaattatc gcgcgcggtg tcatctatgt tactagatct ctagagtctc aagcttggcg   4620
cgcccacgtg actagtggca ctggccgtcg ttttacaacg tcgtgactgg gaaaaccctg   4680
gcgttaccca acttaatcgc cttgcagcac atcccccttt cgccagctgg cgtaatagcg   4740
aagaggcccg caccgatcgc ccttcccaac agttgcgcag cctgaatggc gaatgctaga   4800
gcagcttgag cttggatcag attgtcgttt cccgccttca gtttaaacta tcagtgtttg   4860
acaggatata ttggcgggta aacctaagag aaaagagcgt tta                       4903
```

<210> SEQ ID NO 22
<211> LENGTH: 3465
<212> TYPE: DNA

-continued

<213> ORGANISM: Artificial Sequence
<220> FEATURE:
<223> OTHER INFORMATION: Nucleotide sequence of expression cassette 1391

<400> SEQUENCE: 22
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140
tcttcttgct gattggttct ataagaaatc tagtattttc tttgaaacag agttttcccg 1200
tggttttcga acttggagaa agattgttaa gcttctgtat attctgccca aatttgtcgg 1260
gcccatggcg aaaaacgttg cgattttcgg cttattgttt tctcttcttg tgttggttcc 1320
ttctcagatc ttcgcccaaa aacttcctgg aaatgacaac agcacggcaa cgctgtgcct 1380
tgggcaccat gcagtaccaa acggaacgat agtgaaaaca atcacgaatg accaaattga 1440
agttactaat gctactgagc tggttcagaa ttcctcaata ggtgaaatat gcgacagtcc 1500
tcatcagatc cttgatggag aaaactgcac actaatagat gctctattgg gagaccctca 1560
gtgtgatggc ttccaaaata agaaatggga cctttttgtt gaacgaagca aagcctacag 1620
caactgttac ccttatgatg tgccggatta tgcctccctt aggtcactag ttgcctcatc 1680
cggcacactg gagtttaaca atgaaagctt caattggact ggagtcactc aaaacggaac 1740
aagttctgct tgcataagga gatctaataa tagtttcttt agtagattaa attggttgac 1800
ccacttaaac ttcaaatacc cagcattgaa cgtgactatg ccaaacaatg aacaatttga 1860
caaattgtac atttgggggg ttcaccaccc gggtacggac aaggaccaaa tcttcctgta 1920
tgctcaatca tcaggaagaa tcacagtatc taccaaaaga agccaacaag ctgtaatccc 1980
gaatatcgga tctagaccca gaataaggaa tatccctagc agaataagca tctattggac 2040
aatagtaaaa ccgggagaca tacttttgat taacagcaca gggaatctaa ttgctcctag 2100
gggttacttc aaaatacgaa gtgggaaaag ctcaataatg agatcagatg cacccattgg 2160
caaatgcaat tctgaatgca tcactccaaa tggaagcatt cccaatgaca aaccattcca 2220

```
aaatgtaaac aggatcacat acggggcctg tcccagatat gttaagcaaa gcactctgaa   2280

attggcaaca ggaatgcgaa atgtaccaga gaaacaaact agaggcatat ttggcgcaat   2340

agcgggtttc atagaaaatg gttgggaggg aatggtggat ggttggtacg gtttcaggca   2400

tcaaaattct gagggaagag gacaagcagc agatctcaaa agcactcaag cagcaatcga   2460

tcaaatcaat gggaagctga atcgattgat cgggaaaacc aacgagaaat tccatcagat   2520

tgaaaaagaa ttctcagaag tcgaagggag aattcaggac cttgagaaat atgttgagga   2580

cactaaaata gatctctggt catacaacgc ggagcttctt gttgccctgg agaaccaaca   2640

tacaattgat ctaactgact cagaaatgaa caaactgttt gaaaaaacaa agaagcaact   2700

aagggaaaat gctgaggata tgggcaatgg ttgtttcaaa atataccaca aatgtgacaa   2760

tgcctgcata ggatcaatca gaaatggaac ttatgaccac gatgtataca gagatgaagc   2820

attaaacaac cggttccaga tcaagggagt tgagctgaag tcagggtaca aagattggat   2880

cctatggatt tcctttgcca tatcatgttt tttgctttgt gttgctttgt tggggttcat   2940

catgtgggcc tgccaaaagg gcaacattag gtgcaacatt tgcatttgaa ggcctatttt   3000

ctttagtttg aatttactgt tattcggtgt gcatttctat gtttggtgag cggttttctg   3060

tgctcagagt gtgtttattt tatgtaattt aatttctttg tgagctcctg tttagcaggt   3120

cgtcccttca gcaaggacac aaaaagattt taattttatt aaaaaaaaaa aaaaaaaaga   3180

ccgggaattc gatatcaagc ttatcgacct gcagatcgtt caaacatttg gcaataaagt   3240

ttcttaagat tgaatcctgt tgccggtctt gcgatgatta tcatataatt tctgttgaat   3300

tacgttaagc atgtaataat taacatgtaa tgcatgacgt tatttatgag atgggttttt   3360

atgattagag tcccgcaatt atacatttaa tacgcgatag aaaacaaaat atagcgcgca   3420

aactaggata aattatcgcg cgcggtgtca tctatgttac tagat                   3465
```

```
<210> SEQ ID NO 23
<211> LENGTH: 574
<212> TYPE: PRT
<213> ORGANISM: Artificial Sequence
<220> FEATURE:
<223> OTHER INFORMATION: Amino acid sequence of PDISP/H3 Victoria

<400> SEQUENCE: 23

Met Ala Lys Asn Val Ala Ile Phe Gly Leu Leu Phe Ser Leu Leu Val
1               5                   10                  15

Leu Val Pro Ser Gln Ile Phe Ala Gln Lys Leu Pro Gly Asn Asp Asn
            20                  25                  30

Ser Thr Ala Thr Leu Cys Leu Gly His His Ala Val Pro Asn Gly Thr
        35                  40                  45

Ile Val Lys Thr Ile Thr Asn Asp Gln Ile Glu Val Thr Asn Ala Thr
    50                  55                  60

Glu Leu Val Gln Asn Ser Ser Ile Gly Glu Ile Cys Asp Ser Pro His
65                  70                  75                  80

Gln Ile Leu Asp Gly Glu Asn Cys Thr Leu Ile Asp Ala Leu Leu Gly
                85                  90                  95

Asp Pro Gln Cys Asp Gly Phe Gln Asn Lys Lys Trp Asp Leu Phe Val
            100                 105                 110

Glu Arg Ser Lys Ala Tyr Ser Asn Cys Tyr Pro Tyr Asp Val Pro Asp
        115                 120                 125

Tyr Ala Ser Leu Arg Ser Leu Val Ala Ser Ser Gly Thr Leu Glu Phe
    130                 135                 140
```

-continued

```
Asn Asn Glu Ser Phe Asn Trp Thr Gly Val Thr Gln Asn Gly Thr Ser
145                 150                 155                 160

Ser Ala Cys Ile Arg Arg Ser Asn Asn Ser Phe Phe Ser Arg Leu Asn
                165                 170                 175

Trp Leu Thr His Leu Asn Phe Lys Tyr Pro Ala Leu Asn Val Thr Met
            180                 185                 190

Pro Asn Asn Glu Gln Phe Asp Lys Leu Tyr Ile Trp Gly Val His His
        195                 200                 205

Pro Gly Thr Asp Lys Asp Gln Ile Phe Leu Tyr Ala Gln Ser Ser Gly
    210                 215                 220

Arg Ile Thr Val Ser Thr Lys Arg Ser Gln Gln Ala Val Ile Pro Asn
225                 230                 235                 240

Ile Gly Ser Arg Pro Arg Ile Arg Asn Ile Pro Ser Arg Ile Ser Ile
                245                 250                 255

Tyr Trp Thr Ile Val Lys Pro Gly Asp Ile Leu Leu Ile Asn Ser Thr
            260                 265                 270

Gly Asn Leu Ile Ala Pro Arg Gly Tyr Phe Lys Ile Arg Ser Gly Lys
        275                 280                 285

Ser Ser Ile Met Arg Ser Asp Ala Pro Ile Gly Lys Cys Asn Ser Glu
    290                 295                 300

Cys Ile Thr Pro Asn Gly Ser Ile Pro Asn Asp Lys Pro Phe Gln Asn
305                 310                 315                 320

Val Asn Arg Ile Thr Tyr Gly Ala Cys Pro Arg Tyr Val Lys Gln Ser
                325                 330                 335

Thr Leu Lys Leu Ala Thr Gly Met Arg Asn Val Pro Glu Lys Gln Thr
            340                 345                 350

Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Arg Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Gly Tyr Lys Asp Trp Ile Leu Trp Ile Ser Phe
    530                 535                 540

Ala Ile Ser Cys Phe Leu Leu Cys Val Ala Leu Leu Gly Phe Ile Met
545                 550                 555                 560
```

```
Trp Ala Cys Gln Lys Gly Asn Ile Arg Cys Asn Ile Cys Ile
                565                 570


<210> SEQ ID NO 24
<211> LENGTH: 48
<212> TYPE: DNA
<213> ORGANISM: Artificial Sequence
<220> FEATURE:
<223> OTHER INFORMATION: IF(SacII)-Kozac_PDI.c

<400> SEQUENCE: 24

gtcgggccca ataccgcgga gaaaatggcg aaaaacgttg cgattttc                  48


<210> SEQ ID NO 25
<211> LENGTH: 4914
<212> TYPE: DNA
<213> ORGANISM: Artificial Sequence
<220> FEATURE:
<223> OTHER INFORMATION: Nucleotide sequence of Construct 2181

<400> SEQUENCE: 25

tggcaggata tattgtggtg taaacaaatt gacgcttaga caacttaata acacattgcg     60

gacgttttta atgtactgaa ttaacgccga atcccgggct ggtatattta tatgttgtca    120

aataactcaa aaaccataaa agtttaagtt agcaagtgtg tacattttta cttgaacaaa    180

aatattcacc tactactgtt ataaatcatt attaaacatt agagtaaaga aatatggatg    240

ataagaacaa gagtagtgat attttgacaa caattttgtt gcaacatttg agaaaatttt    300

gttgttctct cttttcattg gtcaaaaaca atagagagag aaaaaggaag agggagaata    360

aaaacataat gtgagtatga gagagaaagt tgtacaaaag ttgtaccaaa atagttgtac    420

aaatatcatt gaggaatttg acaaaagcta cacaaataag ggttaattgc tgtaaataaa    480

taaggatgac gcattagaga gatgtaccat tagagaattt ttggcaagtc attaaaaaga    540

aagaataaat tatttttaaa attaaaagtt gagtcatttg attaaacatg tgattattta    600

atgaattgat gaaagagttg gattaaagtt gtattagtaa ttagaatttg gtgtcaaatt    660

taatttgaca tttgatcttt tcctatatat tgccccatag agtcagttaa ctcattttta    720

tatttcatag atcaaataag agaaataacg gtatattaat ccctccaaaa aaaaaaaacg    780

gtatatttac taaaaaatct aagccacgta ggaggataac aggatccccg taggaggata    840

acatccaatc caaccaatca caacaatcct gatgagataa cccactttaa gcccacgcat    900

ctgtggcaca tctacattat ctaaatcaca cattcttcca cacatctgag ccacacaaaa    960

accaatccac atctttatca cccattctat aaaaaatcac actttgtgag tctacacttt   1020

gattcccttc aaacacatac aaagagaaga gactaattaa ttaattaatc atcttgagag   1080

aaaatggaac gagctataca aggaaacgac gctagggaac aagctaacag tgaacgttgg   1140

gatggaggat caggaggtac cacttctccc ttcaaacttc ctgacgaaag tccgagttgg   1200

actgagtggc ggctacataa cgatgagacg aattcgaatc aagataatcc ccttggtttc   1260

aaggaaagct ggggtttcgg gaaagttgta tttaagagat atctcagata cgacaggacg   1320

gaagcttcac tgcacagagt ccttggatct tggacgggag attcggttaa ctatgcagca   1380

tctcgatttt tcggtttcga ccagatcgga tgtacctata gtattcggtt tcgaggagtt   1440

agtatcaccg tttctggagg gtcgcgaact cttcagcatc tctgtgagat ggcaattcgg   1500

tctaagcaag aactgctaca gcttgcccca atcgaagtgg aaagtaatgt atcaagagga   1560

tgccctgaag gtactcaaac cttcgaaaaa gaaagcgagt aagttaaaat gcttcttcgt   1620
```

-continued

```
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccagtaca acgttttctt   3060
tcactgaagc gaaatcaaag atctctttgt ggacacgtag tgcggcgcca ttaaataacg   3120
tgtacttgtc ctattcttgt cggtgtggtc ttgggaaaag aaagcttgct ggaggctgct   3180
gttcagcccc atacattact tgttacgatt ctgctgactt tcggcgggtg caatatctct   3240
acttctgctt gacgaggtat tgttgcctgt acttctttct tcttcttctt gctgattggt   3300
tctataagaa atctagtatt ttctttgaaa cagagttttc ccgtggtttt cgaacttgga   3360
gaaagattgt taagcttctg tatattctgc ccaaatttgt cgggcccaat accgcggaga   3420
aaatggcgaa aaacgttgcg attttcggct tattgttttc tcttcttgtg ttggttcctt   3480
ctcagatctt cgcgacgtca ctcctcagcc aaaacgacac ccccatctgt ctatccactg   3540
gcccctggat ctgctgccca aactaactcc atggtgaccc tgggatgcct ggtcaagggc   3600
tatttccctg agccagtgac agtgacctgg aactctggat ccctgtccag cggtgtgcac   3660
accttcccag ctgtcctgca gtctgacctc tacactctga gcagctcagt gactgtcccc   3720
tccagcacct ggcccagcga gaccgtcacc tgcaacgttg cccacccggc cagcagcacc   3780
aaggtggaca agaaaattgt gcccagggat tgtggttgta agccttgcat atgtacagtc   3840
ccagaagtat catctgtctt catcttcccc ccaaagccca aggatgtgct caccattact   3900
ctgactccta aggtcacgtg tgttgtggta gacatcagca aggatgatcc cgaggtccag   3960
ttcagctggt ttgtagatga tgtggaggtg cacacagctc agacgcaacc ccgggaggag   4020
```

-continued cagttcaaca gcactttccg ctcagtcagt gaacttccca tcatgcacca ggactggctc 4080
aatggcaagg agcgatcgct caccatcacc atcaccatca ccatcaccat taaaggccta 4140
ttttctttag tttgaattta ctgttattcg gtgtgcattt ctatgtttgg tgagcggttt 4200
tctgtgctca gagtgtgttt attttatgta atttaatttc tttgtgagct cctgtttagc 4260
aggtcgtccc ttcagcaagg acacaaaaag attttaattt tattaaaaaa aaaaaaaaaa 4320
aagaccggga attcgatatc aagcttatcg acctgcagat cgttcaaaca tttggcaata 4380
aagtttctta agattgaatc ctgttgccgg tcttgcgatg attatcatat aatttctgtt 4440
gaattacgtt aagcatgtaa taattaacat gtaatgcatg acgttattta tgagatgggt 4500
ttttatgatt agagtcccgc aattatacat ttaatacgcg atagaaaaca aaatatagcg 4560
cgcaaactag gataaattat cgcgcgcggt gtcatctatg ttactagatc tctagagtct 4620
caagcttggc gcgcccacgt gactagtggc actggccgtc gttttacaac gtcgtgactg 4680
ggaaaaccct ggcgttaccc aacttaatcg ccttgcagca catccccctt tcgccagctg 4740
gcgtaatagc gaagaggccc gcaccgatcg cccttcccaa cagttgcgca gcctgaatgg 4800
cgaatgctag agcagcttga gcttggatca gattgtcgtt tcccgccttc agtttaaact 4860
atcagtgttt gacaggatat attggcgggt aaacctaaga gaaaagagcg ttta 4914

<210> SEQ ID NO 26
<211> LENGTH: 3480
<212> TYPE: DNA
<213> ORGANISM: Artificial Sequence
<220> FEATURE:
<223> OTHER INFORMATION: Nucleotide sequence of expression cassette 1819

<400> SEQUENCE: 26
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaacg ttttctttca ctgaagcgaa atcaaagatc tctttgtgga cacgtagtgc 960
ggcgccatta aataacgtgt acttgtccta ttcttgtcgg tgtggtcttg ggaaaagaaa 1020
gcttgctgga ggctgctgtt cagccccata cattacttgt tacgattctg ctgactttcg 1080
gcgggtgcaa tatctctact tctgcttgac gaggtattgt tgcctgtact tctttcttct 1140

-continued tcttcttgct gattggttct ataagaaatc tagtattttc tttgaaacag agttttcccg 1200
tggttttcga acttggagaa agattgttaa gcttctgtat attctgccca aatttgtcgg 1260
gcccaatacc gcggagaaaa tggcgaaaaa cgttgcgatt ttcggcttat tgttttctct 1320
tcttgtgttg gttccttctc agatcttcgc ccaaaaactt cctggaaatg acaacagcac 1380
ggcaacgctg tgccttgggc accatgcagt accaaacgga acgatagtga aaacaatcac 1440
gaatgaccaa attgaagtta ctaatgctac tgagctggtt cagaattcct caataggtga 1500
aatatgcgac agtcctcatc agatccttga tggagaaaac tgcacactaa tagatgctct 1560
attgggagac cctcagtgtg atggcttcca aaataagaaa tgggaccttt ttgttgaacg 1620
aagcaaagcc tacagcaact gttaccctta tgatgtgccg gattatgcct cccttaggtc 1680
actagttgcc tcatccggca cactggagtt taacaatgaa agcttcaatt ggactggagt 1740
cactcaaaac ggaacaagtt ctgcttgcat aaggagatct aataatagtt tctttagtag 1800
attaaattgg ttgacccact taaacttcaa atacccagca ttgaacgtga ctatgccaaa 1860
caatgaacaa tttgacaaat tgtacatttg gggggttcac cacccgggta cggacaagga 1920
ccaaatcttc ctgtatgctc aatcatcagg aagaatcaca gtatctacca aaagaagcca 1980
acaagctgta atcccgaata tcggatctag acccagaata aggaatatcc ctagcagaat 2040
aagcatctat tggacaatag taaaaccggg agacatactt ttgattaaca gcacagggaa 2100
tctaattgct cctaggggtt acttcaaaat acgaagtggg aaaagctcaa taatgagatc 2160
agatgcaccc attggcaaat gcaattctga atgcatcact ccaaatggaa gcattcccaa 2220
tgacaaacca ttccaaaatg taaacaggat cacatacggg gcctgtccca gatatgttaa 2280
gcaaagcact ctgaaattgg caacaggaat gcgaaatgta ccagagaaac aaactagagg 2340
catatttggc gcaatagcgg gtttcataga aaatggttgg gagggaatgg tggatggttg 2400
gtacggtttc aggcatcaaa attctgaggg aagaggacaa gcagcagatc tcaaaagcac 2460
tcaagcagca atcgatcaaa tcaatgggaa gctgaatcga ttgatcggga aaaccaacga 2520
gaaattccat cagattgaaa aagaattctc agaagtcgaa gggagaattc aggaccttga 2580
gaaatatgtt gaggacacta aaatagatct ctggtcatac aacgcggagc ttcttgttgc 2640
cctggagaac caacatacaa ttgatctaac tgactcagaa atgaacaaac tgtttgaaaa 2700
aacaaagaag caactaaggg aaaatgctga ggatatgggc aatggttgtt tcaaaatata 2760
ccacaaatgt gacaatgcct gcataggatc aatcagaaat ggaacttatg accacgatgt 2820
atacagagat gaagcattaa acaaccggtt ccagatcaag ggagttgagc tgaagtcagg 2880
gtacaaagat tggatcctat ggatttcctt tgccatatca tgtttttttgc tttgtgttgc 2940
tttgttgggg ttcatcatgt gggcctgcca aaagggcaac attaggtgca acatttgcat 3000
ttgaaggcct attttcttta gtttgaattt actgttattc ggtgtgcatt tctatgtttg 3060
gtgagcggtt ttctgtgctc agagtgtgtt tattttatgt aatttaattt ctttgtgagc 3120
tcctgtttag caggtcgtcc cttcagcaag gacacaaaaa gattttaatt ttattaaaaa 3180
aaaaaaaaaa aaagaccggg aattcgatat caagcttatc gacctgcaga tcgttcaaac 3240
atttggcaat aaagtttctt aagattgaat cctgttgccg gtcttgcgat gattatcata 3300
taatttctgt tgaattacgt taagcatgta ataattaaca tgtaatgcat gacgttattt 3360
atgagatggg tttttatgat tagagtcccg caattataca tttaatacgc gatagaaaac 3420
aaaatatagc gcgcaaacta ggataaatta tcgcgcgcgg tgtcatctat gttactagat 3480

<210> SEQ ID NO 27
<211> LENGTH: 52
<212> TYPE: DNA
<213> ORGANISM: Artificial Sequence
<220> FEATURE:
<223> OTHER INFORMATION: Primer IF-HT1*-PDI.c

<400> SEQUENCE: 27
gtcgggccca ataccgcgga gacaatggcg aaaaacgttg cgattttcgg ct 52

<210> SEQ ID NO 28
<211> LENGTH: 52
<212> TYPE: DNA
<213> ORGANISM: Artificial Sequence
<220> FEATURE:
<223> OTHER INFORMATION: Primer IF-HT2*-PDI.c

<400> SEQUENCE: 28
gtcgggccca ataccgcgga ggaaatggcg aaaaacgttg cgattttcgg ct 52

<210> SEQ ID NO 29
<211> LENGTH: 52
<212> TYPE: DNA
<213> ORGANISM: Artificial Sequence
<220> FEATURE:
<223> OTHER INFORMATION: Primer IF-HT3*-PDI.c

<400> SEQUENCE: 29
gtcgggccca ataccgcgga aaaaatggcg aaaaacgttg cgattttcgg ct 52

<210> SEQ ID NO 30
<211> LENGTH: 52
<212> TYPE: DNA
<213> ORGANISM: Artificial Sequence
<220> FEATURE:
<223> OTHER INFORMATION: Primer IF-HT4*-PDI.c

<400> SEQUENCE: 30
gtcgggccca ataccgcgga aacaatggcg aaaaacgttg cgattttcgg ct 52

<210> SEQ ID NO 31
<211> LENGTH: 52
<212> TYPE: DNA
<213> ORGANISM: Artificial Sequence
<220> FEATURE:
<223> OTHER INFORMATION: Primer IF-HT5*-PDI.c

<400> SEQUENCE: 31
gtcgggccca ataccgcgga agcaatggcg aaaaacgttg cgattttcgg ct 52

<210> SEQ ID NO 32
<211> LENGTH: 52
<212> TYPE: DNA
<213> ORGANISM: Artificial Sequence
<220> FEATURE:
<223> OTHER INFORMATION: Primer IF-HT6*-PDI.c

<400> SEQUENCE: 32
gtcgggccca ataccgcgga agaaatggcg aaaaacgttg cgattttcgg ct 52

<210> SEQ ID NO 33
<211> LENGTH: 53
<212> TYPE: DNA
<213> ORGANISM: Artificial Sequence
<220> FEATURE:
<223> OTHER INFORMATION: IF-HT7*-PDI.c

<400> SEQUENCE: 33
gtcgggccca ataccgcgga aagaaatggc gaaaaacgtt gcgattttcg gct 53

<210> SEQ ID NO 34
<211> LENGTH: 54
<212> TYPE: DNA
<213> ORGANISM: Artificial Sequence
<220> FEATURE:
<223> OTHER INFORMATION: IF-HT8*-PDI.c

<400> SEQUENCE: 34
gtcgggccca ataccgcgga aaagaaatgg cgaaaaacgt tgcgattttc ggct 54

<210> SEQ ID NO 35
<211> LENGTH: 1722
<212> TYPE: DNA
<213> ORGANISM: Artificial Sequence
<220> FEATURE:
<223> OTHER INFORMATION: Nucleotide sequence of PDISP/H1 California

<400> SEQUENCE: 35
atggcgaaaa acgttgcgat tttcggctta ttgttttctc ttcttgtgtt ggttccttct 60
cagatcttcg ctgacacatt atgtataggt tatcatgcga acaattcaac agacactgta 120
gacacagtac tagaaaagaa tgtaacagta acacactctg ttaaccttct agaagacaag 180
cataacggga aactatgcaa actaagaggg gtagccccat tgcatttggg taaatgtaac 240
attgctggct ggatcctggg aaatccagag tgtgaatcac tctccacagc aagctcatgg 300
tcctacattg tggaaacacc tagttcagac aatggaacgt gttacccagg agatttcatc 360
gattatgagg agctaagaga gcaattgagc tcagtgtcat catttgaaag gtttgagata 420
ttccccaaga caagttcatg gcccaatcat gactcgaaca aaggtgtaac ggcagcatgt 480
cctcatgctg gagcaaaaag cttctacaaa aatttaatat ggctagttaa aaaaggaaat 540
tcatacccaa agctcagcaa atcctacatt aatgataaag ggaaagaagt cctcgtgcta 600
tggggcattc accatccatc tactagtgct gaccaacaaa gtctctatca gaatgcagat 660
gcatatgttt ttgtggggtc atcaagatac agcaagaagt tcaagccgga aatagcaata 720
agacccaaag tgagggatca agaagggaga atgaactatt actggacact agtagagccg 780
ggagacaaaa taacattcga agcaactgga aatctagtgg taccgagata tgcattcgca 840
atggaaagaa atgctggatc tggtattatc atttcagata caccagtcca cgattgcaat 900
acaacttgtc aaacacccaa gggtgctata aacaccagcc tcccatttca gaatatacat 960
ccgatcacaa ttggaaaatg tccaaaatat gtaaaaagca caaaattgag actggccaca 1020
ggattgagga atatcccgtc tattcaatct agaggactat ttggggccat tgccggtttc 1080
attgaagggg ggtggacagg gatggtagat ggatggtacg gttatcacca tcaaaatgag 1140
caggggtcag gatatgcagc cgacctgaag agcacacaga atgccattga cgagattact 1200
aacaaagtaa attctgttat tgaaaagatg aatacacagt tcacagcagt aggtaaagag 1260
ttcaaccacc tggaaaaaag aatagagaat ttaaataaaa aagttgatga tggtttcctg 1320
gacatttgga cttacaatgc cgaactgttg gttctattgg aaaatgaaag aactttggac 1380
taccacgatt caaatgtgaa gaacttatat gaaaaggtaa gaagccagct aaaaaacaat 1440
gccaaggaaa ttggaaacgg ctgctttgaa ttttaccaca aatgcgataa cacgtgcatg 1500
gaaagtgtca aaaatgggac ttatgactac ccaaaatact cagaggaagc aaaattaaac 1560
agagaagaaa tagatggggt aaagctggaa tcaacaagga tttaccagat tttggcgatc 1620

```
tattcaactg tcgccagttc attggtactg gtagtctccc tgggggcaat cagtttctgg   1680

atgtgctcta atgggtctct acagtgtaga atatgtattt aa                      1722


<210> SEQ ID NO 36
<211> LENGTH: 573
<212> TYPE: PRT
<213> ORGANISM: Artificial Sequence
<220> FEATURE:
<223> OTHER INFORMATION: Amino acid sequence of PDISP/H1 California

<400> SEQUENCE: 36

Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Ala Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255

Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
```

```
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 37
<211> LENGTH: 1728
<212> TYPE: DNA
<213> ORGANISM: Artificial Sequence
<220> FEATURE:
<223> OTHER INFORMATION: Nucleotide sequence of PDISP/H5 Indonesia

<400> SEQUENCE: 37

```
atggcgaaaa acgttgcgat tttcggctta ttgttttctc ttcttgtgtt ggttccttct      60

cagatcttcg ccgatcagat ttgcattggt taccatgcaa acaattcaac agagcaggtt     120

gacacaatca tggaaaagaa cgttactgtt acacatgccc aagacatact ggaaaagaca     180

cacaacggga agctctgcga tctagatgga gtgaagcctc taattttaag agattgtagt     240

gtagctggat ggctcctcgg gaacccaatg tgtgacgaat tcatcaatgt accggaatgg     300

tcttacatag tggagaaggc caatccaacc aatgacctct gttacccagg gagtttcaac     360

gactatgaag aactgaaaca cctattgagc agaataaacc attttgagaa aattcaaatc     420

atccccaaaa gttcttggtc cgatcatgaa gcctcatcag gagttagctc agcatgtcca     480

tacctgggaa gtccctcctt ttttagaaat gtggtatggc ttatcaaaaa gaacagtaca     540

tacccaacaa taaagaaaag ctacaataat accaaccaag aggatctttt ggtactgtgg     600

ggaattcacc atcctaatga tgcggcagag cagacaaggc tatatcaaaa cccaaccacc     660

tatatttcca ttgggacatc aacactaaac cagagattgg taccaaaaat agctactaga     720

tccaaagtaa acgggcaaag tggaaggatg gagttcttct ggacaatttt aaaacctaat     780
```

-continued

```
gatgcaatca acttcgagag taatggaaat ttcattgctc cagaatatgc atacaaaatt    840

gtcaagaaag gggactcagc aattatgaaa agtgaattgg aatatggtaa ctgcaacacc    900

aagtgtcaaa ctccaatggg ggcgataaac tctagtatgc cattccacaa catacaccct    960

ctcaccatcg ggaatgcccc caaatatgtg aaatcaaaca gattagtcct tgcaacaggg   1020

ctcagaaata gccctcaaag agagagcaga agaaaaaaga gaggactatt tggagctata   1080

gcaggtttta tagagggagg atggcaggga atggtagatg gttggtatgg gtaccaccat   1140

agcaatgagc aggggagtgg gtacgctgca gacaaagaat ccactcaaaa ggcaatagat   1200

ggagtcacca ataaggtcaa ctcaatcatt gacaaaatga acactcagtt tgaggccgtt   1260

ggaagggaat ttaataactt agaaaggaga atagagaatt taaacaagaa gatggaagac   1320

gggtttctag atgtctggac ttataatgcc gaacttctgg ttctcatgga aaatgagaga   1380

actctagact ttcatgactc aaatgttaag aacctctacg acaaggtccg actacagctt   1440

agggataatg caaaggagct gggtaacggt tgtttcgagt tctatcacaa atgtgataat   1500

gaatgtatgg aaagtataag aaacggaacg tacaactatc cgcagtattc agaagaagca   1560

agattaaaaa gagaggaaat aagtggggta aaattggaat caataggaac ttaccaaata   1620

ctgtcaattt attcaacagt ggcgagttcc ctagcactgg caatcatgat ggctggtcta   1680

tctttatgga tgtgctccaa tggatcgtta caatgcagaa tttgcatt                1728
```

<210> SEQ ID NO 38
<211> LENGTH: 576
<212> TYPE: PRT
<213> ORGANISM: Artificial Sequence
<220> FEATURE:
<223> OTHER INFORMATION: Amino acid sequence of PDISP/H5 Indonesia

<400> SEQUENCE: 38

```
Met Ala Lys Asn Val Ala Ile Phe Gly Leu Leu Phe Ser Leu Leu Val
1               5                   10                  15

Leu Val Pro Ser Gln Ile Phe Ala Asp Gln Ile Cys Ile Gly Tyr His
            20                  25                  30

Ala Asn Asn Ser Thr Glu Gln Val Asp Thr Ile Met Glu Lys Asn Val
        35                  40                  45

Thr Val Thr His Ala Gln Asp Ile Leu Glu Lys Thr His Asn Gly Lys
    50                  55                  60

Leu Cys Asp Leu Asp Gly Val Lys Pro Leu Ile Leu Arg Asp Cys Ser
65                  70                  75                  80

Val Ala Gly Trp Leu Leu Gly Asn Pro Met Cys Asp Glu Phe Ile Asn
                85                  90                  95

Val Pro Glu Trp Ser Tyr Ile Val Glu Lys Ala Asn Pro Thr Asn Asp
            100                 105                 110

Leu Cys Tyr Pro Gly Ser Phe Asn Asp Tyr Glu Glu Leu Lys His Leu
        115                 120                 125

Leu Ser Arg Ile Asn His Phe Glu Lys Ile Gln Ile Ile Pro Lys Ser
    130                 135                 140

Ser Trp Ser Asp His Glu Ala Ser Ser Gly Val Ser Ser Ala Cys Pro
145                 150                 155                 160

Tyr Leu Gly Ser Pro Ser Phe Phe Arg Asn Val Val Trp Leu Ile Lys
                165                 170                 175

Lys Asn Ser Thr Tyr Pro Thr Ile Lys Lys Ser Tyr Asn Asn Thr Asn
            180                 185                 190
```

```
Gln Glu Asp Leu Leu Val Leu Trp Gly Ile His His Pro Asn Asp Ala
        195                 200                 205

Ala Glu Gln Thr Arg Leu Tyr Gln Asn Pro Thr Thr Tyr Ile Ser Ile
    210                 215                 220

Gly Thr Ser Thr Leu Asn Gln Arg Leu Val Pro Lys Ile Ala Thr Arg
225                 230                 235                 240

Ser Lys Val Asn Gly Gln Ser Gly Arg Met Glu Phe Phe Trp Thr Ile
                245                 250                 255

Leu Lys Pro Asn Asp Ala Ile Asn Phe Glu Ser Asn Gly Asn Phe Ile
            260                 265                 270

Ala Pro Glu Tyr Ala Tyr Lys Ile Val Lys Lys Gly Asp Ser Ala Ile
        275                 280                 285

Met Lys Ser Glu Leu Glu Tyr Gly Asn Cys Asn Thr Lys Cys Gln Thr
    290                 295                 300

Pro Met Gly Ala Ile Asn Ser Ser Met Pro Phe His Asn Ile His Pro
305                 310                 315                 320

Leu Thr Ile Gly Glu Cys Pro Lys Tyr Val Lys Ser Asn Arg Leu Val
                325                 330                 335

Leu Ala Thr Gly Leu Arg Asn Ser Pro Gln Arg Glu Ser Arg Arg Lys
            340                 345                 350

Lys Arg Gly Leu Phe Gly Ala Ile Ala Gly Phe Ile Glu Gly Gly Trp
        355                 360                 365

Gln Gly Met Val Asp Gly Trp Tyr Gly Tyr His His Ser Asn Glu Gln
    370                 375                 380

Gly Ser Gly Tyr Ala Ala Asp Lys Glu Ser Thr Gln Lys Ala Ile Asp
385                 390                 395                 400

Gly Val Thr Asn Lys Val Asn Ser Ile Ile Asp Lys Met Asn Thr Gln
                405                 410                 415

Phe Glu Ala Val Gly Arg Glu Phe Asn Asn Leu Glu Arg Arg Ile Glu
            420                 425                 430

Asn Leu Asn Lys Lys Met Glu Asp Gly Phe Leu Asp Val Trp Thr Tyr
        435                 440                 445

Asn Ala Glu Leu Leu Val Leu Met Glu Asn Glu Arg Thr Leu Asp Phe
    450                 455                 460

His Asp Ser Asn Val Lys Asn Leu Tyr Asp Lys Val Arg Leu Gln Leu
465                 470                 475                 480

Arg Asp Asn Ala Lys Glu Leu Gly Asn Gly Cys Phe Glu Phe Tyr His
                485                 490                 495

Lys Cys Asp Asn Glu Cys Met Glu Ser Ile Arg Asn Gly Thr Tyr Asn
            500                 505                 510

Tyr Pro Gln Tyr Ser Glu Glu Ala Arg Leu Lys Arg Glu Glu Ile Ser
        515                 520                 525

Gly Val Lys Leu Glu Ser Ile Gly Thr Tyr Gln Ile Leu Ser Ile Tyr
    530                 535                 540

Ser Thr Val Ala Ser Ser Leu Ala Leu Ala Ile Met Met Ala Gly Leu
545                 550                 555                 560

Ser Leu Trp Met Cys Ser Asn Gly Ser Leu Gln Cys Arg Ile Cys Ile
                565                 570                 575
```

<210> SEQ ID NO 39
<211> LENGTH: 1701
<212> TYPE: DNA
<213> ORGANISM: Artificial Sequence
<220> FEATURE:
<223> OTHER INFORMATION: Nucleotide sequence of PDISP/H7 Hangzhou

<400> SEQUENCE: 39

```
atggcgaaaa acgttgcgat tttcggctta ttgttttctc ttcttgtgtt ggttccttct     60
cagatcttcg cggacaaaat ctgcctcgga catcatgccg tgtcaaacgg aaccaaagta    120
aacacattaa ctgaaagagg agtggaagtc gtcaatgcaa ctgaaacagt ggaacgaaca    180
aacatcccca ggatctgctc aaaagggaaa aggacagttg acctcggtca atgtggactc    240
ctggggacaa tcactggacc acctcaatgt gaccaattcc tagaattttc agccgattta    300
attattgaga ggcgagaagg aagtgatgtc tgttatcctg ggaaattcgt gaatgaagaa    360
gctctgaggc aaattctcag agaatcaggc ggaattgaca aggaagcaat gggattcaca    420
tacagtggaa taagaactaa tggagcaacc agtgcatgta ggagatcagg atcttcattc    480
tatgcagaaa tgaaatggct cctgtcaaac acagataatg ctgcattccc gcagatgact    540
aagtcatata aaaatacaag aaaaagccca gctctaatag tatgggggat ccatcattcc    600
gtatcaactg cagagcaaac caagctatat gggagtggaa acaaactggt gacagttggg    660
agttctaatt atcaacaatc ttttgtaccg agtccaggag cgagaccaca agttaatggt    720
atatctggaa gaattgactt tcattggcta atgctaaatc ccaatgatac agtcactttc    780
agtttcaatg gggctttcat agctccagac cgtgcaagct tcctgagagg aaaatctatg    840
ggaatccaga gtggagtaca ggttgatgcc aattgtgaag gggactgcta tcatagtgga    900
gggacaataa taagtaactt gccatttcag aacatagata gcagggcagt tggaaaatgt    960
ccgagatatg ttaagcaaag gagtctgctg ctagcaacag ggatgaagaa tgttcctgag   1020
attccaaagg gaagaggcct atttggtgct atagcgggtt tcattgaaaa tggatgggaa   1080
ggcctaattg atggttggta tggtttcaga caccagaatg cacagggaga gggaactgct   1140
gcagattaca aaagcactca atcggcaatt gatcaaataa caggaaaatt aaaccggctt   1200
atagaaaaaa ccaaccaaca atttgagttg atcgacaatg aattcaatga ggtagagaag   1260
caaatcggta atgtgataaa ttggaccaga gattctataa cagaagtgtg gtcatacaat   1320
gctgaactct tggtagcaat ggagaaccag catacaattg atctggctga ttcagaaatg   1380
gacaaactgt acgaacgagt gaaaagacag ctgagagaga atgctgaaga agatggcact   1440
ggttgctttg aaatatttca caagtgtgat gatgactgta tggccagtat tagaaataac   1500
acctatgatc acagcaaata cagggaagag gcaatgcaaa atagaataca gattgaccca   1560
gtcaaactaa gcagcggcta caaagatgtg atactttggt ttagcttcgg ggcatcatgt   1620
ttcatacttc tagccattgt aatgggcctt gtcttcatat gtgtaaagaa tggaaacatg   1680
cggtgcacta tttgtatata a                                              1701
```

<210> SEQ ID NO 40
<211> LENGTH: 566
<212> TYPE: PRT
<213> ORGANISM: Artificial Sequence
<220> FEATURE:
<223> OTHER INFORMATION: Amino acid sequence of PDISP/H7 Hangzhou

<400> SEQUENCE: 40

```
Met Ala Lys Asn Val Ala Ile Phe Gly Leu Leu Phe Ser Leu Leu Val
1               5                   10                  15

Leu Val Pro Ser Gln Ile Phe Ala Asp Lys Ile Cys Leu Gly His His
            20                  25                  30

Ala Val Ser Asn Gly Thr Lys Val Asn Thr Leu Thr Glu Arg Gly Val
        35                  40                  45
```

-continued

```
Glu Val Val Asn Ala Thr Glu Thr Val Glu Arg Thr Asn Ile Pro Arg
    50                  55                  60

Ile Cys Ser Lys Gly Lys Arg Thr Val Asp Leu Gly Gln Cys Gly Leu
65                  70                  75                  80

Leu Gly Thr Ile Thr Gly Pro Pro Gln Cys Asp Gln Phe Leu Glu Phe
                85                  90                  95

Ser Ala Asp Leu Ile Ile Glu Arg Arg Glu Gly Ser Asp Val Cys Tyr
            100                 105                 110

Pro Gly Lys Phe Val Asn Glu Glu Ala Leu Arg Gln Ile Leu Arg Glu
        115                 120                 125

Ser Gly Gly Ile Asp Lys Glu Ala Met Gly Phe Thr Tyr Ser Gly Ile
    130                 135                 140

Arg Thr Asn Gly Ala Thr Ser Ala Cys Arg Arg Ser Gly Ser Ser Phe
145                 150                 155                 160

Tyr Ala Glu Met Lys Trp Leu Leu Ser Asn Thr Asp Asn Ala Ala Phe
                165                 170                 175

Pro Gln Met Thr Lys Ser Tyr Lys Asn Thr Arg Lys Ser Pro Ala Leu
            180                 185                 190

Ile Val Trp Gly Ile His His Ser Val Ser Thr Ala Glu Gln Thr Lys
        195                 200                 205

Leu Tyr Gly Ser Gly Asn Lys Leu Val Thr Val Gly Ser Ser Asn Tyr
    210                 215                 220

Gln Gln Ser Phe Val Pro Ser Pro Gly Ala Arg Pro Gln Val Asn Gly
225                 230                 235                 240

Ile Ser Gly Arg Ile Asp Phe His Trp Leu Met Leu Asn Pro Asn Asp
                245                 250                 255

Thr Val Thr Phe Ser Phe Asn Gly Ala Phe Ile Ala Pro Asp Arg Ala
            260                 265                 270

Ser Phe Leu Arg Gly Lys Ser Met Gly Ile Gln Ser Gly Val Gln Val
        275                 280                 285

Asp Ala Asn Cys Glu Gly Asp Cys Tyr His Ser Gly Gly Thr Ile Ile
    290                 295                 300

Ser Asn Leu Pro Phe Gln Asn Ile Asp Ser Arg Ala Val Gly Lys Cys
305                 310                 315                 320

Pro Arg Tyr Val Lys Gln Arg Ser Leu Leu Leu Ala Thr Gly Met Lys
                325                 330                 335

Asn Val Pro Glu Ile Pro Lys Gly Arg Gly Leu Phe Gly Ala Ile Ala
            340                 345                 350

Gly Phe Ile Glu Asn Gly Trp Glu Gly Leu Ile Asp Gly Trp Tyr Gly
        355                 360                 365

Phe Arg His Gln Asn Ala Gln Gly Glu Gly Thr Ala Ala Asp Tyr Lys
    370                 375                 380

Ser Thr Gln Ser Ala Ile Asp Gln Ile Thr Gly Lys Leu Asn Arg Leu
385                 390                 395                 400

Ile Glu Lys Thr Asn Gln Gln Phe Glu Leu Ile Asp Asn Glu Phe Asn
                405                 410                 415

Glu Val Glu Lys Gln Ile Gly Asn Val Ile Asn Trp Thr Arg Asp Ser
            420                 425                 430

Ile Thr Glu Val Trp Ser Tyr Asn Ala Glu Leu Leu Val Ala Met Glu
        435                 440                 445

Asn Gln His Thr Ile Asp Leu Ala Asp Ser Glu Met Asp Lys Leu Tyr
    450                 455                 460
```

-continued

```
Glu Arg Val Lys Arg Gln Leu Arg Glu Asn Ala Glu Glu Asp Gly Thr
465                 470                 475                 480

Gly Cys Phe Glu Ile Phe His Lys Cys Asp Asp Asp Cys Met Ala Ser
                485                 490                 495

Ile Arg Asn Asn Thr Tyr Asp His Ser Lys Tyr Arg Glu Glu Ala Met
            500                 505                 510

Gln Asn Arg Ile Gln Ile Asp Pro Val Lys Leu Ser Ser Gly Tyr Lys
        515                 520                 525

Asp Val Ile Leu Trp Phe Ser Phe Gly Ala Ser Cys Phe Ile Leu Leu
    530                 535                 540

Ala Ile Val Met Gly Leu Val Phe Ile Cys Val Lys Asn Gly Asn Met
545                 550                 555                 560

Arg Cys Thr Ile Cys Ile
                565


<210> SEQ ID NO 41
<211> LENGTH: 1698
<212> TYPE: DNA
<213> ORGANISM: Artificial Sequence
<220> FEATURE:
<223> OTHER INFORMATION: Nucleotide sequence of PDISP/H7 Hangzhou+H5
      Indonesia TMCT

<400> SEQUENCE: 41

atggcgaaaa acgttgcgat tttcggctta ttgttttctc ttcttgtgtt ggttccttct      60

cagatcttcg cggacaaaat ctgcctcgga catcatgccg tgtcaaacgg aaccaaagta     120

aacacattaa ctgaaagagg agtggaagtc gtcaatgcaa ctgaaacagt ggaacgaaca     180

aacatcccca ggatctgctc aaaagggaaa aggacagttg acctcggtca atgtggactc     240

ctggggacaa tcactggacc acctcaatgt gaccaattcc tagaattttc agccgattta     300

attattgaga ggcgagaagg aagtgatgtc tgttatcctg ggaaattcgt gaatgaagaa     360

gctctgaggc aaattctcag agaatcaggc ggaattgaca aggaagcaat gggattcaca     420

tacagtggaa taagaactaa tggagcaacc agtgcatgta ggagatcagg atcttcattc     480

tatgcagaaa tgaaatggct cctgtcaaac acagataatg ctgcattccc gcagatgact     540

aagtcatata aaaatacaag aaaaagccca gctctaatag tatgggggat ccatcattcc     600

gtatcaactg cagagcaaac caagctatat gggagtggaa acaaactggt gacagttggg     660

agttctaatt atcaacaatc ttttgtaccg agtccaggag cgagaccaca agttaatggt     720

atatctggaa gaattgactt tcattggcta atgctaaatc ccaatgatac agtcactttc     780

agtttcaatg gggctttcat agctccagac cgtgcaagct tcctgagagg aaaatctatg     840

ggaatccaga gtggagtaca ggttgatgcc aattgtgaag gggactgcta tcatagtgga     900

gggacaataa taagtaactt gccatttcag aacatagata gcagggcagt tggaaaatgt     960

ccgagatatg ttaagcaaag gagtctgctg ctagcaacag ggatgaagaa tgttcctgag    1020

attccaaagg gaagaggcct atttggtgct atagcgggtt tcattgaaaa tggatgggaa    1080

ggcctaattg atggttggta tggtttcaga caccagaatg cacagggaga gggaactgct    1140

gcagattaca aaagcactca atcggcaatt gatcaaataa caggaaaatt aaaccggctt    1200

atagaaaaaa ccaaccaaca atttgagttg atcgacaatg aattcaatga ggtagagaag    1260

caaatcggta atgtgataaa ttggaccaga gattctataa cagaagtgtg gtcatacaat    1320

gctgaactct tggtagcaat ggagaaccag catacaattg atctggctga ttcagaaatg    1380

gacaaactgt acgaacgagt gaaaagacag ctgagagaga atgctgaaga agatggcact    1440
```

```
ggttgctttg aaatatttca caagtgtgat gatgactgta tggccagtat tagaaataac   1500

acctatgatc acagcaaata cagggaagag gcaatgcaaa atagaataca gattgaccca   1560

gtcaaactaa gcagcggcta ccaaatactg tcaatttatt caacagtggc gagttcccta   1620

gcactggcaa tcatgatggc tggtctatct ttatggatgt gctccaatgg atcgttacaa   1680

tgcagaattt gcatttaa                                                 1698


<210> SEQ ID NO 42
<211> LENGTH: 565
<212> TYPE: PRT
<213> ORGANISM: Artificial Sequence
<220> FEATURE:
<223> OTHER INFORMATION: Amino acid sequence of PDISP/H7 Hangzhou+H5
      Indonesia TMCT

<400> SEQUENCE: 42

Met Ala Lys Asn Val Ala Ile Phe Gly Leu Leu Phe Ser Leu Leu Val
1               5                   10                  15

Leu Val Pro Ser Gln Ile Phe Ala Asp Lys Ile Cys Leu Gly His His
            20                  25                  30

Ala Val Ser Asn Gly Thr Lys Val Asn Thr Leu Thr Glu Arg Gly Val
        35                  40                  45

Glu Val Val Asn Ala Thr Glu Thr Val Glu Arg Thr Asn Ile Pro Arg
    50                  55                  60

Ile Cys Ser Lys Gly Lys Arg Thr Val Asp Leu Gly Gln Cys Gly Leu
65                  70                  75                  80

Leu Gly Thr Ile Thr Gly Pro Pro Gln Cys Asp Gln Phe Leu Glu Phe
                85                  90                  95

Ser Ala Asp Leu Ile Ile Glu Arg Arg Glu Gly Ser Asp Val Cys Tyr
            100                 105                 110

Pro Gly Lys Phe Val Asn Glu Glu Ala Leu Arg Gln Ile Leu Arg Glu
        115                 120                 125

Ser Gly Gly Ile Asp Lys Glu Ala Met Gly Phe Thr Tyr Ser Gly Ile
    130                 135                 140

Arg Thr Asn Gly Ala Thr Ser Ala Cys Arg Arg Ser Gly Ser Ser Phe
145                 150                 155                 160

Tyr Ala Glu Met Lys Trp Leu Leu Ser Asn Thr Asp Asn Ala Ala Phe
                165                 170                 175

Pro Gln Met Thr Lys Ser Tyr Lys Asn Thr Arg Lys Ser Pro Ala Leu
            180                 185                 190

Ile Val Trp Gly Ile His His Ser Val Ser Thr Ala Glu Gln Thr Lys
        195                 200                 205

Leu Tyr Gly Ser Gly Asn Lys Leu Val Thr Val Gly Ser Ser Asn Tyr
    210                 215                 220

Gln Gln Ser Phe Val Pro Ser Pro Gly Ala Arg Pro Gln Val Asn Gly
225                 230                 235                 240

Ile Ser Gly Arg Ile Asp Phe His Trp Leu Met Leu Asn Pro Asn Asp
                245                 250                 255

Thr Val Thr Phe Ser Phe Asn Gly Ala Phe Ile Ala Pro Asp Arg Ala
            260                 265                 270

Ser Phe Leu Arg Gly Lys Ser Met Gly Ile Gln Ser Gly Val Gln Val
        275                 280                 285

Asp Ala Asn Cys Glu Gly Asp Cys Tyr His Ser Gly Gly Thr Ile Ile
    290                 295                 300
```

-continued

```
Ser Asn Leu Pro Phe Gln Asn Ile Asp Ser Arg Ala Val Gly Lys Cys
305                 310                 315                 320

Pro Arg Tyr Val Lys Gln Arg Ser Leu Leu Leu Ala Thr Gly Met Lys
                325                 330                 335

Asn Val Pro Glu Ile Pro Lys Gly Arg Gly Leu Phe Gly Ala Ile Ala
            340                 345                 350

Gly Phe Ile Glu Asn Gly Trp Glu Gly Leu Ile Asp Gly Trp Tyr Gly
        355                 360                 365

Phe Arg His Gln Asn Ala Gln Gly Glu Gly Thr Ala Ala Asp Tyr Lys
    370                 375                 380

Ser Thr Gln Ser Ala Ile Asp Gln Ile Thr Gly Lys Leu Asn Arg Leu
385                 390                 395                 400

Ile Glu Lys Thr Asn Gln Gln Phe Glu Leu Ile Asp Asn Glu Phe Asn
                405                 410                 415

Glu Val Glu Lys Gln Ile Gly Asn Val Ile Asn Trp Thr Arg Asp Ser
            420                 425                 430

Ile Thr Glu Val Trp Ser Tyr Asn Ala Glu Leu Leu Val Ala Met Glu
        435                 440                 445

Asn Gln His Thr Ile Asp Leu Ala Asp Ser Glu Met Asp Lys Leu Tyr
    450                 455                 460

Glu Arg Val Lys Arg Gln Leu Arg Glu Asn Ala Glu Glu Asp Gly Thr
465                 470                 475                 480

Gly Cys Phe Glu Ile Phe His Lys Cys Asp Asp Asp Cys Met Ala Ser
                485                 490                 495

Ile Arg Asn Asn Thr Tyr Asp His Ser Lys Tyr Arg Glu Glu Ala Met
            500                 505                 510

Gln Asn Arg Ile Gln Ile Asp Pro Val Lys Leu Ser Ser Gly Tyr Gln
        515                 520                 525

Ile Leu Ser Ile Tyr Ser Thr Val Ala Ser Ser Leu Ala Leu Ala Ile
    530                 535                 540

Met Met Ala Gly Leu Ser Leu Trp Met Cys Ser Asn Gly Ser Leu Gln
545                 550                 555                 560

Cys Arg Ile Cys Ile
                565
```

<210> SEQ ID NO 43
<211> LENGTH: 1734
<212> TYPE: DNA
<213> ORGANISM: Artificial Sequence
<220> FEATURE:
<223> OTHER INFORMATION: Nucleotide sequence of PDISP/HA B Brisbane (PrL-).

<400> SEQUENCE: 43

```
atggcgaaaa acgttgcgat tttcggctta ttgttttctc ttcttgtgtt ggttccttct     60

cagatcttcg ccgatcgaat ctgcactgga ataacatcgt caaactcacc acatgtcgtc    120

aaaactgcta ctcaagggga ggtcaatgtg actggtgtaa taccactgac aacaacaccc    180

accaaatctc attttgcaaa tctcaaagga acagaaacca gggggaaact atgcccaaaa    240

tgcctcaact gcacagatct ggacgtagcc ttgggcagac caaaatgcac ggggaaaata    300

ccctcggcaa gagtttcaat actccatgaa gtcagacctg ttacatctgg gtgctttcct    360

ataatgcacg acagaacaaa aattagacag ctgcctaacc ttctccgagg atacgaacat    420

atcaggttat caacccataa cgttatcaat gcagaaaatg caccaggagg accctacaaa    480

attggaacct cagggtcttg ccctaacatt accaatggaa acggattttt cgcaacaatg    540
```

```
gcttgggccg tcccaaaaaa cgacaaaaac aaaacagcaa caaatccatt aacaatagaa    600

gtaccataca tttgtacaga aggagaagac caaattaccg tttgggggtt ccactctgac    660

aacgagaccc aaatggcaaa gctctatggg gactcaaagc cccagaagtt cacctcatct    720

gccaacggag tgaccacaca ttacgtttca cagattggtg gcttcccaaa tcaaacagaa    780

gacggaggac taccacaaag tggtagaatt gttgttgatt acatggtgca aaaatctggg    840

aaaacaggaa caattaccta tcaaaggggt attttattgc ctcaaaaggt gtggtgcgca    900

agtggcagga gcaaggtaat aaaaggatcc ttgcctttaa ttggagaagc agattgcctc    960

cacgaaaaat acggtggatt aaacaaaagc aagccttact acacagggga acatgcaaag   1020

gccataggaa attgcccaat atgggtgaaa acacccttga agctggccaa tggaaccaaa   1080

tatagacctc ctggtggagg atgggaagga atgattgcag gttggcacgg atacacatcc   1140

catggggcac atggagtagc ggtggcagca gaccttaaga gcactcaaga ggccataaac   1200

aagataacaa aaaatctcaa ctctttgagt gagctggaag taaagaatct tcaaagacta   1260

agcggtgcca tggatgaact ccacaacgaa atactagaac tagatgagaa agtggatgat   1320

ctcagagctg atacaataag ctcacaaata gaactcgcag tcctgctttc caatgaagga   1380

ataataaaca gtgaagatga acatctcttg gcgcttgaaa gaaagctgaa gaaaatgctg   1440

ggcccctctg ctgtagagat agggaatgga tgctttgaaa ccaaacacaa gtgcaaccag   1500

acctgtctcg acagaatagc tgctggtacc tttgatgcag gagaattttc tctccccacc   1560

tttgattcac tgaatattac tgctgcatct ttaaatgacg atggattgga taatcatact   1620

atactgcttt actactcaac tgctgcctcc agtttggctg taacactgat gatagctatc   1680

tttgttgttt atatggtctc cagagacaat gtttcttgct ccatctgtct ataa         1734
```

```
<210> SEQ ID NO 44
<211> LENGTH: 577
<212> TYPE: PRT
<213> ORGANISM: Artificial Sequence
<220> FEATURE:
<223> OTHER INFORMATION: Amino acid sequence of PDISP/HA B Brisbane
      (PrL-).

<400> SEQUENCE: 44

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140
```

-continued

```
Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400

Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
        515                 520                 525

Ala Ser Leu Asn Asp Asp Gly Leu Asp Asn His Thr Ile Leu Leu Tyr
    530                 535                 540

Tyr Ser Thr Ala Ala Ser Ser Leu Ala Val Thr Leu Met Ile Ala Ile
545                 550                 555                 560

Phe Val Val Tyr Met Val Ser Arg Asp Asn Val Ser Cys Ser Ile Cys
```

-continued 565 570 575

Leu

<210> SEQ ID NO 45
<211> LENGTH: 1734
<212> TYPE: DNA
<213> ORGANISM: Artificial Sequence
<220> FEATURE:
<223> OTHER INFORMATION: Nucleotide sequence of PDISP/HA B Brisbane (PrL-)+H1 California TMCT

<400> SEQUENCE: 45

```
atggcgaaaa acgttgcgat tttcggctta ttgttttctc ttcttgtgtt ggttccttct      60
cagatcttcg ccgatcgaat ctgcactgga ataacatcgt caaactcacc acatgtcgtc     120
aaaactgcta ctcaagggga ggtcaatgtg actggtgtaa taccactgac aacaacaccc     180
accaaatctc attttgcaaa tctcaaagga acagaaacca gggggaaact atgcccaaaa     240
tgcctcaact gcacagatct ggacgtagcc ttgggcagac caaaatgcac ggggaaaata     300
ccctcggcaa gagtttcaat actccatgaa gtcagacctg ttacatctgg gtgctttcct     360
ataatgcacg acagaacaaa aattagacag ctgcctaacc ttctccgagg atacgaacat     420
atcaggttat caacccataa cgttatcaat gcagaaaatg caccaggagg accctacaaa     480
attggaacct cagggtcttg ccctaacatt accaatggaa acggattttt cgcaacaatg     540
gcttgggccg tcccaaaaaa cgacaaaaac aaaacagcaa caaatccatt aacaatagaa     600
gtaccataca tttgtacaga aggagaagac caaattaccg tttgggggtt ccactctgac     660
aacgagaccc aaatggcaaa gctctatggg gactcaaagc cccagaagtt cacctcatct     720
gccaacggag tgaccacaca ttacgtttca cagattggtg gcttcccaaa tcaaacagaa     780
gacggaggac taccacaaag tggtagaatt gttgttgatt acatggtgca aaaatctggg     840
aaaacaggaa caattaccta tcaaaggggt attttattgc ctcaaaaggt gtggtgcgca     900
agtggcagga gcaaggtaat aaaaggatcc ttgcctttaa ttggagaagc agattgcctc     960
cacgaaaaat acggtggatt aaacaaaagc aagccttact acacagggga acatgcaaag    1020
gccataggaa attgcccaat atgggtgaaa acacccttga agctggccaa tggaaccaaa    1080
tatagacctc ctggtggagg atgggaagga atgattgcag gttggcacgg atacacatcc    1140
catggggcac atggagtagc ggtggcagca gaccttaaga gcactcaaga ggccataaac    1200
aagataacaa aaaatctcaa ctctttgagt gagctggaag taaagaatct tcaaagacta    1260
agcggtgcca tggatgaact ccacaacgaa atactagaac tagatgagaa agtggatgat    1320
ctcagagctg atacaataag ctcacaaata gaactcgcag tcctgctttc caatgaagga    1380
ataataaaca gtgaagatga acatctcttg gcgcttgaaa gaaagctgaa gaaaatgctg    1440
ggcccctctg ctgtagagat agggaatgga tgctttgaaa ccaaacacaa gtgcaaccag    1500
acctgtctcg acagaatagc tgctggtacc tttgatgcag gagaattttc tctccccacc    1560
tttgattcac tgaatattac tgctgcatct ttaaatgacg atggattgga taattaccag    1620
attttggcga tctattcaac tgtcgccagt tcattggtac tggtagtctc cctgggggca    1680
atcagtttct ggatgtgctc taatgggtct ctacagtgta gaatatgtat ttaa          1734
```

<210> SEQ ID NO 46
<211> LENGTH: 577
<212> TYPE: PRT
<213> ORGANISM: Artificial Sequence
<220> FEATURE:

<223> OTHER INFORMATION: Amino acid sequence of PDISP/HA B Brisbane
(PrL-)+H1 California TMCT

<400> SEQUENCE: 46

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser His
    50                  55                  60

Phe Ala Asn Leu Lys Gly Thr Glu Thr Arg Gly Lys Leu Cys Pro Lys
65                  70                  75                  80

Cys Leu Asn Cys Thr Asp Leu Asp Val Ala Leu Gly Arg Pro Lys Cys
                85                  90                  95

Thr Gly Lys Ile Pro Ser Ala Arg Val Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu His Ile Arg Leu Ser
    130                 135                 140

Thr His Asn Val Ile Asn Ala Glu Asn Ala Pro Gly Gly Pro Tyr Lys
145                 150                 155                 160

Ile Gly Thr Ser Gly Ser Cys Pro Asn Ile Thr Asn Gly Asn Gly Phe
                165                 170                 175

Phe Ala Thr Met Ala Trp Ala Val Pro Lys Asn Asp Lys Asn Lys Thr
            180                 185                 190

Ala Thr Asn Pro Leu Thr Ile Glu Val Pro Tyr Ile Cys Thr Glu Gly
        195                 200                 205

Glu Asp Gln Ile Thr Val Trp Gly Phe His Ser Asp Asn Glu Thr Gln
    210                 215                 220

Met Ala Lys Leu Tyr Gly Asp Ser Lys Pro Gln Lys Phe Thr Ser Ser
225                 230                 235                 240

Ala Asn Gly Val Thr Thr His Tyr Val Ser Gln Ile Gly Gly Phe Pro
                245                 250                 255

Asn Gln Thr Glu Asp Gly Gly Leu Pro Gln Ser Gly Arg Ile Val Val
            260                 265                 270

Asp Tyr Met Val Gln Lys Ser Gly Lys Thr Gly Thr Ile Thr Tyr Gln
        275                 280                 285

Arg Gly Ile Leu Leu Pro Gln Lys Val Trp Cys Ala Ser Gly Arg Ser
    290                 295                 300

Lys Val Ile Lys Gly Ser Leu Pro Leu Ile Gly Glu Ala Asp Cys Leu
305                 310                 315                 320

His Glu Lys Tyr Gly Gly Leu Asn Lys Ser Lys Pro Tyr Tyr Thr Gly
                325                 330                 335

Glu His Ala Lys Ala Ile Gly Asn Cys Pro Ile Trp Val Lys Thr Pro
            340                 345                 350

Leu Lys Leu Ala Asn Gly Thr Lys Tyr Arg Pro Pro Gly Gly Gly Trp
        355                 360                 365

Glu Gly Met Ile Ala Gly Trp His Gly Tyr Thr Ser His Gly Ala His
    370                 375                 380

Gly Val Ala Val Ala Ala Asp Leu Lys Ser Thr Gln Glu Ala Ile Asn
385                 390                 395                 400
```

```
Lys Ile Thr Lys Asn Leu Asn Ser Leu Ser Glu Leu Glu Val Lys Asn
                405                 410                 415

Leu Gln Arg Leu Ser Gly Ala Met Asp Glu Leu His Asn Glu Ile Leu
            420                 425                 430

Glu Leu Asp Glu Lys Val Asp Asp Leu Arg Ala Asp Thr Ile Ser Ser
        435                 440                 445

Gln Ile Glu Leu Ala Val Leu Leu Ser Asn Glu Gly Ile Ile Asn Ser
    450                 455                 460

Glu Asp Glu His Leu Leu Ala Leu Glu Arg Lys Leu Lys Lys Met Leu
465                 470                 475                 480

Gly Pro Ser Ala Val Glu Ile Gly Asn Gly Cys Phe Glu Thr Lys His
                485                 490                 495

Lys Cys Asn Gln Thr Cys Leu Asp Arg Ile Ala Ala Gly Thr Phe Asp
            500                 505                 510

Ala Gly Glu Phe Ser Leu Pro Thr Phe Asp Ser Leu Asn Ile Thr Ala
        515                 520                 525

Ala Ser Leu Asn Asp Asp Gly Leu Asp Asn Tyr Gln Ile Leu Ala Ile
    530                 535                 540

Tyr Ser Thr Val Ala Ser Ser Leu Val Leu Val Val Ser Leu Gly Ala
545                 550                 555                 560

Ile Ser Phe Trp Met Cys Ser Asn Gly Ser Leu Gln Cys Arg Ile Cys
                565                 570                 575

Ile


<210> SEQ ID NO 47
<211> LENGTH: 1731
<212> TYPE: DNA
<213> ORGANISM: Artificial Sequence
<220> FEATURE:
<223> OTHER INFORMATION: Nucleotide sequence of PDISP/HA B
      Massachussetts (PrL-).

<400> SEQUENCE: 47

atggcgaaaa acgttgcgat tttcggctta ttgttttctc ttcttgtgtt ggttccttct      60

cagatcttcg ccgatcgaat ctgcactggg ataacatctt caaactcacc tcatgtggtc     120

aaaacagcta ctcaagggga ggtcaatgtg actggtgtga taccactaac aacaacacca     180

acaaaatctt attttgcaaa tctcaaagga acaaagacca gagggaaact atgcccagac     240

tgtctcaact gtacagatct ggatgtggcc ctgggcaggc caatgtgtgt gggaactaca     300

ccttctgcga aagcttcaat acttcacgaa gtcagacctg ttacatccgg gtgcttccct     360

ataatgcacg acagaacaaa aatcaggcaa ctagccaatc ttctcagagg atatgaaaat     420

atcaggttat caacccaaaa cgttatcgat gcagaaaagg caccaggagg accctacaga     480

cttggaacct caggatcttg ccctaacgct accagtaaaa gcggattttt cgcaacaatg     540

gcttgggctg tcccaaagga caacaacaaa aatgcaacga acccattaac agtagaagta     600

ccatacattt gtgcagaagg ggaagaccaa attactgttt gggggttcca ttcagataac     660

aaaacccaaa tgaagaacct ctatggagac tcaaatcctc aaaagttcac ctcatctgct     720

aatggagtaa ccacacatta tgtttctcag attggcggct tcccagatca aacagaagac     780

ggaggactac cacaaagcgg cagaattgtc gttgattaca tgatgcaaaa acctgggaaa     840

acaggaacaa ttgtctatca aagaggtgtt ttgttgcctc aaaaggtgtg gtgcgcgagt     900

ggcaggagca aagtaataaa agggtccttg cctttaattg gtgaagcaga ttgccttcat     960
```

-continued

```
gaaaaatacg gtggattaaa caaaagcaag ccttactaca caggagaaca tgcaaaagcc   1020

ataggaaatt gcccaatatg ggtgaaaaca cctttgaagc ttgccaatgg aaccaaatat   1080

agacctcctg gtggaggatg ggaaggaatg attgcaggtt ggcacggata cacatctcac   1140

ggagcacatg gagtggcagt tgctgcagac cttaagagca cacaagaagc tataaacaag   1200

ataacaaaaa atctcaactc tttgagtgag ctagaagtaa agaatcttca aaggctaagt   1260

ggtgccatgg atgaactcca caacgaaata ctcgagctgg atgagaaagt ggatgacctc   1320

agagctgaca ctataagttc acaaatagaa cttgcagtct tgctttccaa cgaaggaata   1380

ataaacagtg aagacgagca tctattggca cttgagagaa aactaaagaa aatgctgggt   1440

ccctctgctg tagacatagg aaatggatgc ttcgaaacca aacacaaatg caaccagacc   1500

tgcttagaca ggatagctgc tggcaccttt aatgcaggag agttttctct ccccactttt   1560

gattcattga acattactgc tgcatcttta aatgatgatg gattggataa ccatactata   1620

ctgctctatt actcaactgc tgcttctagt ttggctgtaa cattgatgct agctattttt   1680

attgtttata tggtctccag agacaacgtt tcatgctcca tctgtctata a            1731
```

```
<210> SEQ ID NO 48
<211> LENGTH: 576
<212> TYPE: PRT
<213> ORGANISM: Artificial Sequence
<220> FEATURE:
<223> OTHER INFORMATION: Amino acid sequence of PDISP/HA B
      Massachussetts (PrL-).

<400> SEQUENCE: 48

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Lys Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Ala Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Ala Glu Gly Glu
        195                 200                 205

Asp Gln Ile Thr Val Trp Gly Phe His Ser Asp Asn Lys Thr Gln Met
    210                 215                 220
```

-continued

```
Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Gly Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365

Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn His Thr Ile Leu Leu Tyr Tyr
    530                 535                 540

Ser Thr Ala Ala Ser Ser Leu Ala Val Thr Leu Met Leu Ala Ile Phe
545                 550                 555                 560

Ile Val Tyr Met Val Ser Arg Asp Asn Val Ser Cys Ser Ile Cys Leu
                565                 570                 575
```

```
<210> SEQ ID NO 49
<211> LENGTH: 1731
<212> TYPE: DNA
<213> ORGANISM: Artificial Sequence
<220> FEATURE:
<223> OTHER INFORMATION: Nucleotide sequence of PDISP/HA B
      Massachussetts (PrL-)+H1 California TMCT

<400> SEQUENCE: 49

atggcgaaaa acgttgcgat tttcggctta ttgttttctc ttcttgtgtt ggttccttct      60
```

```
cagatcttcg ccgatcgaat ctgcactggg ataacatctt caaactcacc tcatgtggtc    120

aaaacagcta ctcaagggga ggtcaatgtg actggtgtga taccactaac aacaacacca    180

acaaaatctt attttgcaaa tctcaaagga acaaagacca gagggaaact atgcccagac    240

tgtctcaact gtacagatct ggatgtggcc ctgggcaggc caatgtgtgt gggaactaca    300

ccttctgcga aagcttcaat acttcacgaa gtcagacctg ttacatccgg gtgcttccct    360

ataatgcacg acagaacaaa aatcaggcaa ctagccaatc ttctcagagg atatgaaaat    420

atcaggttat caacccaaaa cgttatcgat gcagaaaagg caccaggagg accctacaga    480

cttggaacct caggatcttg ccctaacgct accagtaaaa gcggattttt cgcaacaatg    540

gcttgggctg tcccaaagga caacaacaaa aatgcaacga acccattaac agtagaagta    600

ccatacattt gtgcagaagg ggaagaccaa attactgttt gggggttcca ttcagataac    660

aaaacccaaa tgaagaacct ctatggagac tcaaatcctc aaaagttcac ctcatctgct    720

aatggagtaa ccacacatta tgtttctcag attggcggct tcccagatca aacagaagac    780

ggaggactac cacaaagcgg cagaattgtc gttgattaca tgatgcaaaa acctgggaaa    840

acaggaacaa ttgtctatca aagaggtgtt ttgttgcctc aaaaggtgtg gtgcgcgagt    900

ggcaggagca aagtaataaa agggtccttg cctttaattg gtgaagcaga ttgccttcat    960

gaaaaatacg gtggattaaa caaaagcaag ccttactaca caggagaaca tgcaaaagcc   1020

ataggaaatt gcccaatatg ggtgaaaaca cctttgaagc ttgccaatgg aaccaaatat   1080

agacctcctg gtggaggatg ggaaggaatg attgcaggtt ggcacggata cacatctcac   1140

ggagcacatg gagtggcagt tgctgcagac cttaagagca cacaagaagc tataaacaag   1200

ataacaaaaa atctcaactc tttgagtgag ctagaagtaa agaatcttca aaggctaagt   1260

ggtgccatgg atgaactcca caacgaaata ctcgagctgg atgagaaagt ggatgacctc   1320

agagctgaca ctataagttc acaaatagaa cttgcagtct tgctttccaa cgaaggaata   1380

ataaacagtg aagacgagca tctattggca cttgagagaa aactaaagaa aatgctgggt   1440

ccctctgctg tagacatagg aaatggatgc ttcgaaacca aacacaaatg caaccagacc   1500

tgcttagaca ggatagctgc tggcaccttt aatgcaggag agttttctct ccccactttt   1560

gattcattga acattactgc tgcatcttta aatgatgatg gattggataa ctaccagatt   1620

ttggcgatct attcaactgt cgccagttca ttggtactgg tagtctccct gggggcaatc   1680

agtttctgga tgtgctctaa tgggtctcta cagtgtagaa tatgtattta a            1731
```

<210> SEQ ID NO 50
<211> LENGTH: 576
<212> TYPE: PRT
<213> ORGANISM: Artificial Sequence
<220> FEATURE:
<223> OTHER INFORMATION: Amino acid sequence of PDISP/HA B Massachussetts (PrL-)+H1 California TMCT

<400> SEQUENCE: 50

```
Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60
```

-continued

```
Phe Ala Asn Leu Lys Gly Thr Lys Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Arg
            100                 105                 110

Pro Val Thr Ser Gly Cys Phe Pro Ile Met His Asp Arg Thr Lys Ile
        115                 120                 125

Arg Gln Leu Ala Asn Leu Leu Arg Gly Tyr Glu Asn Ile Arg Leu Ser
    130                 135                 140

Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Ala Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Gly Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Gly Gly Gly Trp Glu
        355                 360                 365

Gly Met Ile Ala Gly Trp His Gly Tyr Thr Ser His Gly Ala His Gly
    370                 375                 380

Val Ala Val Ala Ala Asp Leu Lys Ser Thr Gln Glu Ala Ile Asn Lys
385                 390                 395                 400

Ile Thr Lys Asn Leu Asn Ser Leu Ser Glu Leu Glu Val Lys Asn Leu
                405                 410                 415

Gln Arg Leu Ser Gly Ala Met Asp Glu Leu His Asn Glu Ile Leu Glu
            420                 425                 430

Leu Asp Glu Lys Val Asp Asp Leu Arg Ala Asp Thr Ile Ser Ser Gln
        435                 440                 445

Ile Glu Leu Ala Val Leu Leu Ser Asn Glu Gly Ile Ile Asn Ser Glu
    450                 455                 460

Asp Glu His Leu Leu Ala Leu Glu Arg Lys Leu Lys Lys Met Leu Gly
465                 470                 475                 480

Pro Ser Ala Val Asp Ile Gly Asn Gly Cys Phe Glu Thr Lys His Lys
```

-continued

```
                485                 490                 495

Cys Asn Gln Thr Cys Leu Asp Arg Ile Ala Ala Gly Thr Phe Asn Ala
            500                 505                 510

Gly Glu Phe Ser Leu Pro Thr Phe Asp Ser Leu Asn Ile Thr Ala Ala
        515                 520                 525

Ser Leu Asn Asp Asp Gly Leu Asp Asn Tyr Gln Ile Leu Ala Ile Tyr
    530                 535                 540

Ser Thr Val Ala Ser Ser Leu Val Leu Val Val Ser Leu Gly Ala Ile
545                 550                 555                 560

Ser Phe Trp Met Cys Ser Asn Gly Ser Leu Gln Cys Arg Ile Cys Ile
                565                 570                 575


<210> SEQ ID NO 51
<211> LENGTH: 1704
<212> TYPE: DNA
<213> ORGANISM: Artificial Sequence
<220> FEATURE:
<223> OTHER INFORMATION: Nucleotide sequence of HA B Wisconsin (PrL-).

<400> SEQUENCE: 51

atgaaggcaa taattgtact actcatggta gtaacatcca atgcagatcg aatctgcact      60

gggataacat cttcaaactc acctcatgtg gtcaaaacag ctactcaagg ggaggtcaat     120

gtgactggcg tgataccact gacaacaaca ccaacaaaat cttattttgc aaatctcaaa     180

ggaacaagga ccagagggaa actatgcccg gactgtctca actgtacaga tctggatgtg     240

gccttgggca ggccaatgtg tgtggggacc acaccttctg ctaaagcttc aatactccac     300

gaggtcagac ctgttacatc cgggtgcttt cctataatgc acgacagaac aaaaatcagg     360

caactaccca atcttctcag aggatatgaa aatatcaggt tatcaaccca aaacgttatc     420

gatgcagaaa aagcaccagg aggaccctac agacttggaa cctcaggatc ttgccctaac     480

gctaccagta aaatcggatt ttttgcaaca atggcttggg ctgtcccaaa ggacaactac     540

aaaaatgcaa cgaacccact aacagtagaa gtaccataca tttgtacaga aggggaagac     600

caaattactg tttgggggtt ccattcagat aacaaaaccc aaatgaagag cctctatgga     660

gactcaaatc ctcaaaagtt cacctcatct gctaatggag taaccacaca ttatgtttct     720

cagattggcg acttcccaga tcaaacagaa gacggaggac taccacaaag cggcagaatt     780

gttgttgatt acatgatgca aaaacctggg aaaacaggaa caattgtcta tcaaagaggt     840

gttttgttgc ctcaaaaggt gtggtgcgcg agtggcagga gcaaagtaat aaaagggtca     900

ttgcctttaa ttggtgaagc agattgcctt catgaaaaat acggtggatt aaacaaaagc     960

aagccttact acacaggaga acatgcaaaa gccataggaa attgcccaat atgggtaaaa    1020

acacctttga agcttgccaa tggaaccaaa tatagacctc ctggtggagg atgggaagga    1080

atgattgcag gttggcacgg atacacatct cacggagcac atggagtggc agtggcggca    1140

gaccttaaga gtacacaaga agctataaat aagataacaa aaaatctcaa ttctttgagt    1200

gagctagaag taaagaacct tcaaagacta agtggtgcca tggatgaact ccacaacgaa    1260

atactcgagc tggatgagaa agtggatgat ctcagagctg acactataag ctcacaaata    1320

gaacttgcag tcttgctttc caacgaagga ataataaaca gtgaagacga gcatctattg    1380

gcacttgaga gaaaactaaa gaaaatgctg ggtccctctg ctgtagacat aggaaacgga    1440

tgcttcgaaa ccaaacacaa atgcaaccag acctgcttag acaggatagc tgctggcacc    1500

tttaatgcag gagaattttc tctccccact tttgattcat tgaacattac tgctgcatct    1560
```

```
ttaaatgatg atggattgga taaccatact atactgctct attactcaac tgctgcttct   1620

agtttggctg taacattaat gctagctatt tttattgttt atatggtctc cagagacaac   1680

gtttcatgct ccatctgtct ataa                                          1704


<210> SEQ ID NO 52
<211> LENGTH: 567
<212> TYPE: PRT
<213> ORGANISM: Artificial Sequence
<220> FEATURE:
<223> OTHER INFORMATION: Amino acid sequence of HA B Wisconsin (PrL-).

<400> SEQUENCE: 52

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335
```

```
Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

His Thr Ile Leu Leu Tyr Tyr Ser Thr Ala Ala Ser Ser Leu Ala Val
    530                 535                 540

Thr Leu Met Leu Ala Ile Phe Ile Val Tyr Met Val Ser Arg Asp Asn
545                 550                 555                 560

Val Ser Cys Ser Ile Cys Leu
                565


<210> SEQ ID NO 53
<211> LENGTH: 1704
<212> TYPE: DNA
<213> ORGANISM: Artificial Sequence
<220> FEATURE:
<223> OTHER INFORMATION: Nucleotide sequence of HA B Wisconsin (PrL-)+H1
      California TMCT

<400> SEQUENCE: 53

atgaaggcaa taattgtact actcatggta gtaacatcca atgcagatcg aatctgcact      60

gggataacat cttcaaactc acctcatgtg gtcaaaacag ctactcaagg ggaggtcaat     120

gtgactggcg tgataccact gacaacaaca ccaacaaaat cttattttgc aaatctcaaa     180

ggaacaagga ccagagggaa actatgcccg gactgtctca actgtacaga tctggatgtg     240

gccttgggca ggccaatgtg tgtggggacc acaccttctg ctaaagcttc aatactccac     300

gaggtcagac ctgttacatc cgggtgcttt cctataatgc acgacagaac aaaaatcagg     360

caactaccca atcttctcag aggatatgaa aatatcaggt tatcaaccca aaacgttatc     420

gatgcagaaa aagcaccagg aggaccctac agacttggaa cctcaggatc ttgccctaac     480

gctaccagta aaatcggatt ttttgcaaca atggcttggg ctgtcccaaa ggacaactac     540

aaaaatgcaa cgaacccact aacagtagaa gtaccataca tttgtacaga aggggaagac     600

caaattactg tttgggggtt ccattcagat aacaaaaccc aaatgaagag cctctatgga     660

gactcaaatc ctcaaaagtt cacctcatct gctaatggag taaccacaca ttatgtttct     720
```

cagattggcg acttcccaga tcaaacagaa gacggaggac taccacaaag cggcagaatt 780
gttgttgatt acatgatgca aaaacctggg aaaacaggaa caattgtcta tcaaagaggt 840
gttttgttgc ctcaaaaggt gtggtgcgcg agtggcagga gcaaagtaat aaaagggtca 900
ttgcctttaa ttggtgaagc agattgcctt catgaaaaat acggtggatt aaacaaaagc 960
aagccttact acacaggaga acatgcaaaa gccataggaa attgcccaat atgggtaaaa 1020
acacctttga agcttgccaa tggaaccaaa tatagacctc ctggtggagg atgggaagga 1080
atgattgcag gttggcacgg atacacatct cacggagcac atggagtggc agtggcggca 1140
gaccttaaga gtacacaaga agctataaat aagataacaa aaaatctcaa ttctttgagt 1200
gagctagaag taaagaacct tcaaagacta agtggtgcca tggatgaact ccacaacgaa 1260
atactcgagc tggatgagaa agtggatgat ctcagagctg acactataag ctcacaaata 1320
gaacttgcag tcttgctttc caacgaagga ataataaaca gtgaagacga gcatctattg 1380
gcacttgaga gaaaactaaa gaaaatgctg ggtccctctg ctgtagacat aggaaacgga 1440
tgcttcgaaa ccaaacacaa atgcaaccag acctgcttag acaggatagc tgctggcacc 1500
tttaatgcag gagaattttc tctccccact tttgattcat tgaacattac tgctgcatct 1560
ttaaatgatg atggattgga taactaccag atttggcga tctattcaac tgtcgccagt 1620
tcattggtac tggtagtctc cctgggggca atcagtttct ggatgtgctc taatgggtct 1680
ctacagtgta gaatatgtat ttaa 1704

<210> SEQ ID NO 54
<211> LENGTH: 567
<212> TYPE: PRT
<213> ORGANISM: Artificial Sequence
<220> FEATURE:
<223> OTHER INFORMATION: Amino acid sequence of HA B Wisconsin (PrL-)+H1 California TMC

<400> SEQUENCE: 54

Met Lys Ala Ile Ile Val Leu Leu Met Val Val Thr Ser Asn Ala Asp
1 5 10 15

Arg Ile Cys Thr Gly Ile Thr Ser Ser Asn Ser Pro His Val Val Lys
20 25 30

Thr Ala Thr Gln Gly Glu Val Asn Val Thr Gly Val Ile Pro Leu Thr
35 40 45

Thr Thr Pro Thr Lys Ser Tyr Phe Ala Asn Leu Lys Gly Thr Arg Thr
50 55 60

Arg Gly Lys Leu Cys Pro Asp Cys Leu Asn Cys Thr Asp Leu Asp Val
65 70 75 80

Ala Leu Gly Arg Pro Met Cys Val Gly Thr Thr Pro Ser Ala Lys Ala
85 90 95

Ser Ile Leu His Glu Val Arg Pro Val Thr Ser Gly Cys Phe Pro Ile
100 105 110

Met His Asp Arg Thr Lys Ile Arg Gln Leu Pro Asn Leu Leu Arg Gly
115 120 125

Tyr Glu Asn Ile Arg Leu Ser Thr Gln Asn Val Ile Asp Ala Glu Lys
130 135 140

Ala Pro Gly Gly Pro Tyr Arg Leu Gly Thr Ser Gly Ser Cys Pro Asn
145 150 155 160

Ala Thr Ser Lys Ile Gly Phe Phe Ala Thr Met Ala Trp Ala Val Pro
165 170 175

-continued

```
Lys Asp Asn Tyr Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Gly Gly Gly Trp Glu Gly Met Ile Ala Gly Trp His Gly Tyr
        355                 360                 365

Thr Ser His Gly Ala His Gly Val Ala Val Ala Ala Asp Leu Lys Ser
    370                 375                 380

Thr Gln Glu Ala Ile Asn Lys Ile Thr Lys Asn Leu Asn Ser Leu Ser
385                 390                 395                 400

Glu Leu Glu Val Lys Asn Leu Gln Arg Leu Ser Gly Ala Met Asp Glu
                405                 410                 415

Leu His Asn Glu Ile Leu Glu Leu Asp Glu Lys Val Asp Asp Leu Arg
            420                 425                 430

Ala Asp Thr Ile Ser Ser Gln Ile Glu Leu Ala Val Leu Leu Ser Asn
        435                 440                 445

Glu Gly Ile Ile Asn Ser Glu Asp Glu His Leu Leu Ala Leu Glu Arg
    450                 455                 460

Lys Leu Lys Lys Met Leu Gly Pro Ser Ala Val Asp Ile Gly Asn Gly
465                 470                 475                 480

Cys Phe Glu Thr Lys His Lys Cys Asn Gln Thr Cys Leu Asp Arg Ile
                485                 490                 495

Ala Ala Gly Thr Phe Asn Ala Gly Glu Phe Ser Leu Pro Thr Phe Asp
            500                 505                 510

Ser Leu Asn Ile Thr Ala Ala Ser Leu Asn Asp Asp Gly Leu Asp Asn
        515                 520                 525

Tyr Gln Ile Leu Ala Ile Tyr Ser Thr Val Ala Ser Ser Leu Val Leu
    530                 535                 540

Val Val Ser Leu Gly Ala Ile Ser Phe Trp Met Cys Ser Asn Gly Ser
545                 550                 555                 560

Leu Gln Cys Arg Ile Cys Ile
                565
```

<210> SEQ ID NO 55
<211> LENGTH: 514
<212> TYPE: DNA

<213> ORGANISM: Artificial Sequence
<220> FEATURE:
<223> OTHER INFORMATION: Segment of native CPMV RNA 2 genome,
nucleotides 1-514

<400> SEQUENCE: 55

```
tattaaaatc ttaataggtt ttgataaaag cgaacgtggg gaaacccgaa ccaaaccttc     60

ttctaaactc tctctcatct ctcttaaagc aaacttctct cttgtctttc ttgcatgagc    120

gatcttcaac gttgtcagat cgtgcttcgg caccagtaca atgttttctt tcactgaagc    180

gaaatcaaag atctctttgt ggacacgtag tgcggcgcca ttaaataacg tgtacttgtc    240

ctattcttgt cggtgtggtc ttgggaaaag aaagcttgct ggaggctgct gttcagcccc    300

atacattact tgttacgatt ctgctgactt tcggcgggtg caatatctct acttctgctt    360

gacgaggtat tgttgcctgt acttctttct tcttcttctt gctgattggt tctataagaa    420

atctagtatt ttctttgaaa cagagttttc ccgtggtttt cgaacttgga gaaagattgt    480

taagcttctg tatattctgc ccaaatttga aatg                                514
```

<210> SEQ ID NO 56
<211> LENGTH: 511
<212> TYPE: DNA
<213> ORGANISM: Artificial Sequence
<220> FEATURE:
<223> OTHER INFORMATION: CPMV RNA2 genome, nucleotides 1-514, with
modifications at 115 and 162

<400> SEQUENCE: 56

```
tattaaaatc ttaataggtt ttgataaaag cgaacgtggg gaaacccgaa ccaaaccttc     60

ttctaaactc tctctcatct ctcttaaagc aaacttctct cttgtctttc ttgcgtgagc    120

gatcttcaac gttgtcagat cgtgcttcgg caccagtaca acgttttctt tcactgaagc    180

gaaatcaaag atctctttgt ggacacgtag tgcggcgcca ttaaataacg tgtacttgtc    240

ctattcttgt cggtgtggtc ttgggaaaag aaagcttgct ggaggctgct gttcagcccc    300

atacattact tgttacgatt ctgctgactt tcggcgggtg caatatctct acttctgctt    360

gacgaggtat tgttgcctgt acttctttct tcttcttctt gctgattggt tctataagaa    420

atctagtatt ttctttgaaa cagagttttc ccgtggtttt cgaacttgga gaaagattgt    480

taagcttctg tatattctgc ccaaatttga a                                   511
```

<210> SEQ ID NO 57
<211> LENGTH: 69
<212> TYPE: DNA
<213> ORGANISM: Artificial Sequence
<220> FEATURE:
<223> OTHER INFORMATION: Patatin signal peptide (nucleotide sequence)

<400> SEQUENCE: 57

```
atggcaacta ctaaaacttt tttaatttta ttttttatga tattagcaac tactagttca     60

acatgtgct                                                             69
```

<210> SEQ ID NO 58
<211> LENGTH: 23
<212> TYPE: PRT
<213> ORGANISM: Artificial Sequence
<220> FEATURE:
<223> OTHER INFORMATION: Patatin signal peptide (amino acid sequence)

<400> SEQUENCE: 58

Met Ala Thr Thr Lys Thr Phe Leu Ile Leu Phe Phe Met Ile Leu Ala

-continued 1 5 10 15

Thr Thr Ser Ser Thr Cys Ala
20

<210> SEQ ID NO 59
<211> LENGTH: 29
<212> TYPE: PRT
<213> ORGANISM: Artificial Sequence
<220> FEATURE:
<223> OTHER INFORMATION: HA transmembrane domain consensus amino acid sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 59

Ile Leu Xaa Ile Tyr Tyr Ser Thr Val Ala Ile Ser Ser Leu Xaa Leu
1 5 10 15

Xaa Xaa Met Leu Ala Gly Xaa Ser Xaa Trp Met Cys Ser
20 25